(12) United States Patent
Turzi

(10) Patent No.: US 9,517,255 B2
(45) Date of Patent: Dec. 13, 2016

(54) PROCESS, TUBE AND DEVICE FOR THE PREPARATION OF WOUND HEALANT COMPOSITION

(71) Applicant: Antoine Turzi, Mollens (CH)

(72) Inventor: Antoine Turzi, Mollens (CH)

( * ) Notice: Subject to any disclaimer, the term of this patent is extended or adjusted under 35 U.S.C. 154(b) by 0 days.

(21) Appl. No.: 14/596,268

(22) Filed: Jan. 14, 2015

(65) Prior Publication Data

US 2015/0125436 A1   May 7, 2015

Related U.S. Application Data

(62) Division of application No. 13/634,020, filed as application No. PCT/IB2011/000684 on Mar. 11, 2011, now Pat. No. 8,945,537.

(30) Foreign Application Priority Data

Mar. 11, 2010 (GB) .................................. 1004072.3

(51) Int. Cl.

| | |
|---|---|
| *A61K 38/48* | (2006.01) |
| *A61K 31/728* | (2006.01) |
| *A61K 35/14* | (2015.01) |
| *A61K 35/15* | (2015.01) |
| *A61K 35/16* | (2015.01) |
| *A61K 35/17* | (2015.01) |
| *A61K 35/18* | (2015.01) |
| *A61K 35/19* | (2015.01) |
| *A61K 38/36* | (2006.01) |
| *A61L 26/00* | (2006.01) |
| *A61M 1/02* | (2006.01) |
| *A61Q 19/08* | (2006.01) |
| *A61K 8/98* | (2006.01) |

(52) U.S. Cl.
CPC ........... *A61K 38/4833* (2013.01); *A61K 8/981* (2013.01); *A61K 31/728* (2013.01); *A61K 35/14* (2013.01); *A61K 35/15* (2013.01); *A61K 35/16* (2013.01); *A61K 35/17* (2013.01); *A61K 35/18* (2013.01); *A61K 35/19* (2013.01); *A61K 38/363* (2013.01); *A61L 26/0057* (2013.01); *A61L 26/0066* (2013.01); *A61M 1/0209* (2013.01); *A61M 1/029* (2013.01); *A61Q 19/08* (2013.01); *A61L 2300/30* (2013.01); *A61L 2300/412* (2013.01); *A61M 2202/0425* (2013.01); *C12Y 304/21005* (2013.01)

(58) Field of Classification Search
CPC .................................................. A61K 31/728
See application file for complete search history.

(56) References Cited

U.S. PATENT DOCUMENTS

| | | | |
|---|---|---|---|
| 7,094,464 B2 * | 8/2006 | Mao ..................... | G01N 33/521 422/504 |
| 2004/0151709 A1 | 8/2004 | Barrueta et al. | |

FOREIGN PATENT DOCUMENTS

| | | |
|---|---|---|
| CH | 696 752 | 11/2007 |
| WO | WO 99/66923 | 12/1999 |
| WO | WO 2008/022651 | 2/2008 |
| WO | WO 2008/023026 | 2/2008 |

OTHER PUBLICATIONS

Chen et al Bioconjugate Chem. 1997, 8:730-734.*
Carr et al. Arthritis and Rheumatism, 1980, 23(12):1371-1375.*
Written Opinion in International Application No. PCT/IB2011/000684, Jan. 30, 2012, pp. 1-12.
Mason, M. et al. "Attachment of hyaluronic acid to polypropylene, polystyrene, and polytetrafluoroethylene" *Biomaterials*, 2000, pp. 31-36, vol. 21.
Okabe, K. et al. "Injectable soft-tissue augmentation by tissue engineering and regenerative medicine with human mesenchymal stromal cells, platelet-rich plasma and hyaluronic acid scaffolds" *Cytotherapy*, 2009, pp. 307-316, vol. 11, No. 3.

* cited by examiner

*Primary Examiner* — Bin Shen
(74) *Attorney, Agent, or Firm* — Saliwanchik, Lloyd & Eisenschenk

(57) ABSTRACT

The present invention is related to the field of tissue regeneration. It concerns more particularly new processes, tubes and devices for thrombin, platelet concentrate and wound healant preparations, alone or in combination with cell extracts, cell compositions and uses thereof.

25 Claims, 16 Drawing Sheets
(1 of 16 Drawing Sheet(s) Filed in Color)

Figure 1A
Figure 1B
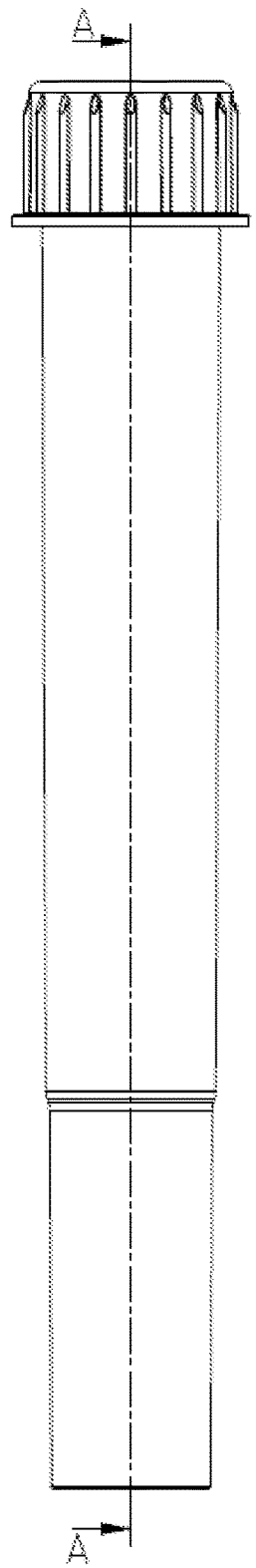
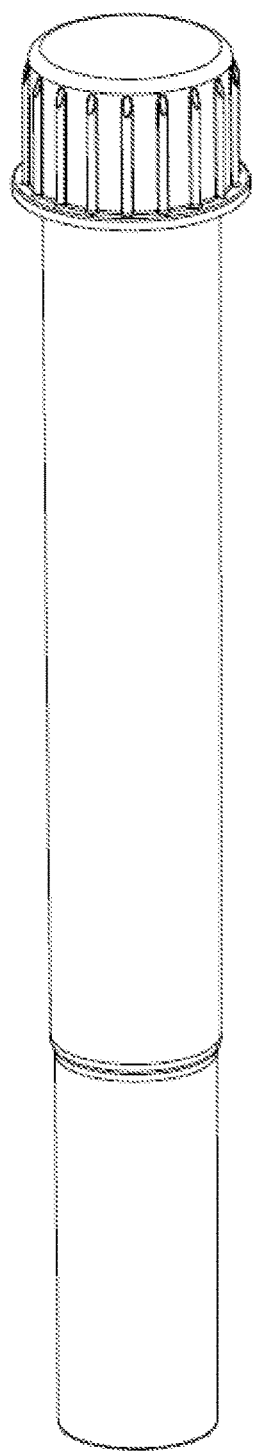

E

Figure 5A
Figure 5B
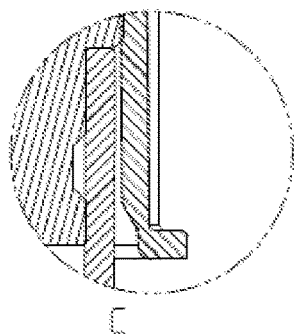
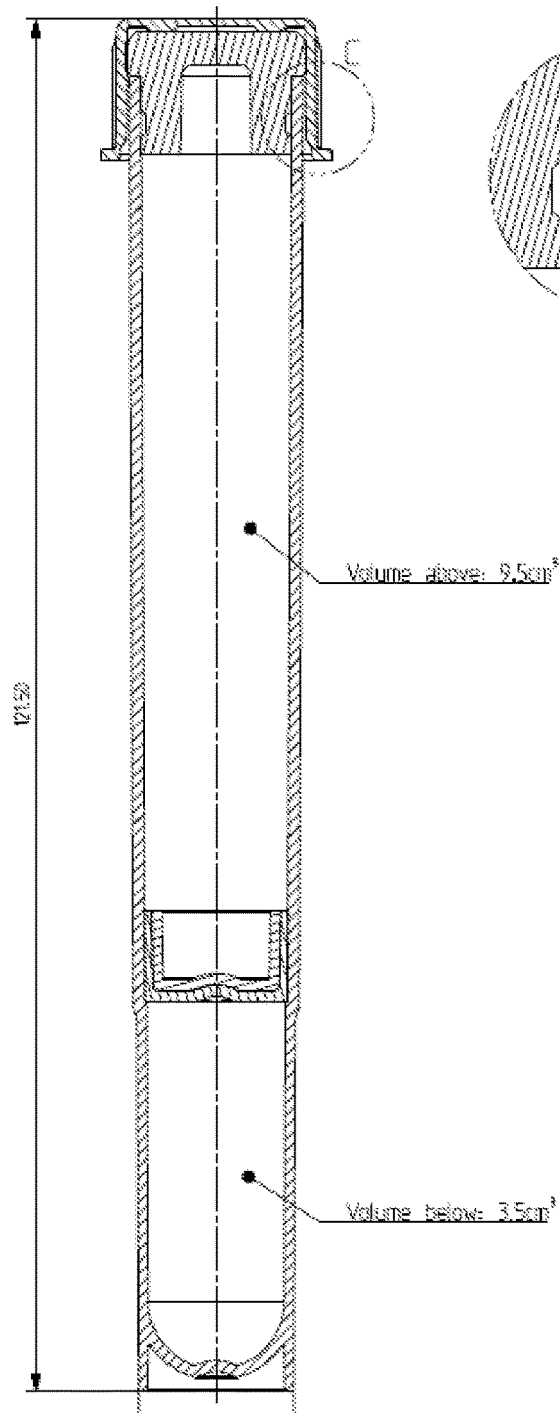

PROCESS, TUBE AND DEVICE FOR THE PREPARATION OF WOUND HEALANT COMPOSITION

CROSS-REFERENCE TO RELATED APPLICATIONS

This application is a divisional of U.S. application Ser. No. 13/634,020, filed Nov. 13, 2012, U.S. Pat. No. 8,945, 537, which is the U.S. national stage application of International Patent Application No. PCT/IB2011/000684, filed Mar. 11, 2011, the disclosures of which are hereby incorporated by reference in their entirety, including all figures, tables and amino acid or nucleic acid sequences.

FIELD OF THE INVENTION

The present invention is related to the field of tissue regeneration. It concerns more particularly new processes, tubes and devices for thrombin, platelet concentrate and wound healant preparations, compositions and uses thereof.

BACKGROUND OF THE INVENTION

The importance of biological autologous materials in the healing process has been well documented. Most importantly, two biological autologous materials have been shown to be directly implicated in the formation of the structure of blood clots, which provide a haemostatic barrier whose role is to ensure hemostasis and seal the wound: (1) fibrin, which derives from the separation of plasma fibrinogen into two strands through the action of thrombin, and (2) the activated membranes of platelets. The wound healing process is generally presented as the succession of a coagulation phase, an inflammatory process and a regeneration process. The coagulation phase (blood clotting or clot formation) is a complex process whereby a damaged blood vessel wall is covered by a fibrin clot to stop hemorrhage and the repair of the damaged vessel is initiated by the release in large quantities of cytokines and growth factors from platelet alpha granules. The formation of blood clots (formed in physiological conditions by fibrin, platelets and red blood cells, among other blood components) is a natural phenomenon that results from tissue trauma and its role in the wound healing process, as well as in the union of bone fractures, is well-known.

Blood coagulation is the result of the complex interaction of a number of protein clotting factors through a cascade. In general, damage to the vascular endothelium exposes subendothelial structures, which attract platelets and induce them to aggregate reversibly. The protein thrombin, formed during activation of the coagulation pathway generates insoluble cross-linked fibrils of the protein fibrin and causes the platelets to aggregate irreversibly. The resulting platelet-fibrin clot is an effective barrier against loss of blood from the vascular system and also serves as a scaffold for subsequent repair of the lining of the blood vessel.

The inflammation process, which follows the formation of a blood clot, is stimulated by numerous vasoactive mediators and chemotactic factors (specific signals in the form of proteins) released by white blood cells and platelets. These signals attract macrophages that "clean" the site from bacteria and foreign particles as well as red blood cells before the migration of new cells. The tissue regeneration phase involves the chemoattraction and the mitosis of the undifferentiated cells in the scaffold (or growth matrix) formed by the blood clot. The new cells which multiply under the stimulation of platelet growth factors will replace damaged or destroyed cells injured by macrophages. Growth factors and numerous plasma proteins, also called signaling molecules, which promote cell migration and division within blood clots, play a crucial role in the wound healing process.

Bioadhesive sealants and fibrin glues represent a relatively new technological advance that duplicates the biological process of the final stage of blood coagulation. Clinical reports document the utility of fibrin glue in a variety of surgical fields, such as, cardiovascular, thoracic, transplantation, head and neck, oral, gastrointestinal, orthopedic, neurosurgical, and plastic surgery. At the time of surgery, the two primary components comprising the fibrin glue, fibrinogen and thrombin, are mixed together to form a clot. The clot adheres to the necessary tissues, bone, or nerve within seconds, but is then slowly reabsorbed by the body in approximately 10 days by fibrinolysis. Important features of fibrin glue is its ability to: (1) achieve haemostasis at vascular anastomoses particularly in areas which are difficult to approach with sutures or where suture placement presents excessive risk; (2) control bleeding from needle holes or arterial tears which cannot be controlled by suturing alone; and (3) obtain haemostasis in heparinized patients or those with coagulopathy. See, Borst, H. G., et al., *J. Thorac. Cardiovasc. Surg.,* 84:548-553 (1982); Walterbusch, G. J, et al., *Thorac Cardiovasc. Surg.,* 30:234-235 (1982); and Wolner, F. J, et al., *Thorac. Cardiovasc. Surg.,* 30:236-237 (1982).

Theoretically, it is possible to amplify the effects of these first phases in the wound-healing cascade by discarding the red blood cells and increasing the concentration of growth factors.

Blood clotting amplification can be defined as the formation of an "enriched clot (EC)". ECs are obtained through the use of platelet concentrates and have been described in Platelets and Megacaryocytes 2004, vol 1 & 2, as "Structure and signals", Ed. Gibbins and Mahaut-Smith, Humana Press, New Jersey. Platelet-rich plasma (PRP) can be defined as an autologous concentrate of platelets in a small volume of plasma; it has been developed as an autologous biomaterial and has proven to be useful in the healing and regeneration of tissues (Marx et al., 2004, J. Oral Maxillofac. Surg., 62, 489-496). PRP not only consists in a platelet concentrate but also contains growth factors (such as platelet-derived growth factor: PDGF, vascular endothelial growth factor: VEGF, transforming growth factor: TGF and epidermal growth factor: EGF, etc.) that are actively secreted by platelets and are known to have a fundamental role in wound healing initiation process.

For example, PDGF is known to initiate connective tissue healing, including bone regeneration and repair. PDGF also increases mitogenesis (healing cells), angiogenesis (endothelial mitosis into functioning capillaries) and macrophage activation. VEGF released by the leukocytes is also known to have potent angiogenic, mitogenic and vascular permeability-enhancing activities on endothelial cells. TGF-[beta] promotes cell mitosis and differentiation for connective tissue and bone, acts on mesenchymal stem cells, preosteoblasts and fibroblasts and inhibits osteoclast formation. EGF is known to induce epithelial development and promote angiogenesis. Platelet concentrates are generally used in dental implantology and bone surgery, notably in the USA. Various techniques of preparation of PRP by centrifugation processes have been developed. However, due to the sensitivity of the platelet cells and the variability of the efficiency of the methods of separation of the platelets from the red blood cells, a great variability exists among the methods used for the preparation of platelet concentrates. The automated settings from Biomet PCCS & GPS (Marx et al., 2004, above), present the drawback of being a complex process with prohibitive costs for the process of a large blood sample. In those systems, there is also an important loss of valuable biologic tissue from the patients, therefore there is the need for the development of a reliable process collecting the plasma cells with high yields, ease of use and cost effectiveness.

In addition, the obtaining of platelet concentrates still needs the use of relatively complex kits and costly dedicated machinery and the equally costly involvement of specialized technicians. This drawback makes the current known methods of preparation of PRP not adapted to a point-of-care use.

Further, the preparation of cells in view of cellular or tissue regeneration for use in transplantation, post-operative regeneration or for aesthetic purpose is faced to the long-term conservation problem of cells and tissues. Tissue or cell cryoconservation is generally used for the long-term maintaining of tissues or cells, notably platelets, but this technique has shown serious drawbacks and problems such as crystal formation, osmotic problems, aggregation, inhibition of protein synthesis ability, stress protein expression in response to thermal stress. Therefore, tissue or cell cryoconservation is known to alter the cell viability and stability (Agence française de sécurité sanitaire, 2003; Arnaud et al., 1999, Cryobiology, 38, 192-199; Tablin et al., 2001, Cryobiology, 43(2), 114-23). Some of the cryoconservation side effects may be limited by the use of anti-freezing agents such as DMSO or glycerol or other cryopreservatives (U.S. Pat. No. 5,891,617, Oh et al., Cornea, 26, 840-846) but the concentration of these agents has to be adapted to limit their toxicity and side effects.

Therefore, there is a need for new or alternative method of preparation of cells and tissues suited for use extemporaneously while preserving their integrity, notably in terms of growth factors, secretion ability and viability.

SUMMARY OF THE INVENTION

The invention relates to the field of tissue regeneration. It concerns more particularly new processes, tubes and devices for thrombin, platelet concentrate and wound healant preparations, compositions and uses thereof. The invention also relates to new cell formulations, new platelet-rich plasma (PRP) formulations, methods of preparation of new cell formulations or PRP formulations, use of such cell or PRP preparations, optionally admixed with a cell extract, such as an autologous extract of keratinocytes, bone marrow cells, fibroblasts, periosteum or corneal cells, melanocytes and Langerhans cells; fat cells; fat tissue; muscle cells such as myoblasts and satellite cells; osteoblasts; chondrocytes; umbilical cord cells; mesenchymal stem cells (MSCs); pre-adipocytes; pre-endothelial cells; Schwann cells; or Achilles tendon cells.

In one aspect, the invention provides a method for preparing a completely autologous and extemporaneous wound healant or tissue healant composition. All of the blood components for the autologous wound healant or tissue healant composition are derived from a single patient to whom the autologous wound healant or tissue healant composition will be applied (same patient).

In one aspect, the invention provides a process or method for the preparation of thrombin serum, comprising the steps of:

a) Collecting whole blood in a tube containing a thixotropic gel, b) Centrifuging the tube until liberation of thrombin serum, and c) Collecting the thrombin serum.

In another aspect, the invention provides a process or method for the preparation of a wound healant composition or tissue healant composition, comprising the steps of:

a) Collecting whole blood preferably in a tube containing hyaluronic acid, a thixotropic gel and/or an anticoagulant preferably sodium citrate, b) Centrifuging the tube preferably until migration of red blood cells under the thixotropic gel and preferably until migration of hyaluronic acid above the enriched plasma, c) Optionally mixing the hyaluronic acid and the enriched plasma, preferably by inverting the tube, and d) Collecting the supernatant containing hyaluronic acid and the enriched plasma.

In another aspect, the invention provides a tube for collecting and separating a fluid sample comprising:

i) two distinct parts differing in size and diameter, ii) a filter separating the two parts, and iii) optionally a thixotropic gel and an anticoagulant.

In a preferred embodiment of the invention, the tube consists of the features as illustrated in FIGS. 1 to 14.

In another aspect, the invention relates to a blood bag system or blood collection tubes device comprising multiple bags or tubes useful for the collection, storage, use and delivery of blood components.

In a preferred aspect, the invention provides a blood bag system or blood collection tubes device according to FIG. 15.

In another aspect, the invention provides a blood bag system or blood collection tubes device comprising a single entry conduit connected to a multiple conduit adapter with adapter conduits connected to at least two bags or tubes, wherein each adapter conduit of the multiple conduit adapter is connected to one single bag or tube.

The blood collection tubes are preferably evacuated, sealed and filled with thixotropic gel and anticoagulant.

DESCRIPTION OF THE FIGURES

The patent or application file contains at least one drawing executed in color. Copies of this patent or patent application publication, with color drawing(s), will be provided by the Office upon request and payment of the necessary fee.

The accompanying drawings, which are incorporated herein and form a part of the specification illustrate preferred embodiments of the present invention, and together with the description, serve to explain the principles of the invention.

FIGS. 1A and 1B are schematic representations of a tube according to the invention.

FIG. 5A is a schematic representation of the interior of a tube according to the invention.

FIG. 5B is a schematic representation of the cap and tube junction.

FIG. 8 also represents the four symmetrical series of 3 ranges of openings of the external layer or lower layer according to the invention.

FIG. 9 also represents the four symmetrical series of 2 ranges of openings of the internal layer or upper layer according to the invention.

DETAILED DESCRIPTION OF THE INVENTION

Figure 2:
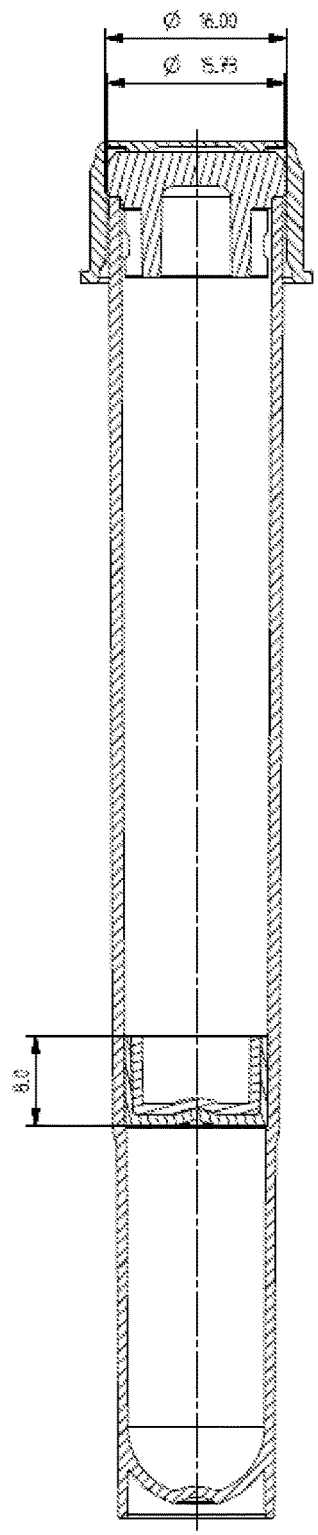
FIGS. 2 and 3 are schematic representations of the interior of a tube according to the invention.

The following paragraphs provide definitions of the terms according to the invention and are intended to apply uniformly throughout the specification and claims unless an otherwise expressly set out definition provides a broader definition.

The expression "thixotropic" means a gel that becomes more fluid as a result of agitation or pressure, i.e., a gel which viscosity is decreasing as a result of agitation or pressure. The term viscosity refers to those characteristics of the specified material(s) determining the degree of gelation, such as for example the firmness or hardness of the material, the degree to which the material resists flowing like a fluid. A thixotropic gel according to the invention comprising a polyester gel or a mixture thereof which is water insoluble and chemically inert to blood constituents which can be used in accordance with the invention. Typical thixotropic gels are used in blood cell separation for diagnostics and proteomics purposes. A thixotropic gel is also herein referred to as a "cell selector gel". Other gels may be used in the present invention.

The expression "point-of-care" means all services provided to patients at the bedside.

The expression "phlebotomy accessories" or "venipuncture accessories" means accessories that allow the puncture of a vein with a needle for the purpose of drawing blood.

Alternative expressions for "wound healant" or "wound sealant" or "tissue healant" or "tissue sealant" or "wound healing composition" or "tissue healing composition" are "bioadhesive sealant" or "fibrin glue".

The expression "wound healant" or "wound sealant" or "tissue healant" or "tissue sealant" or "wound healing composition" or "tissue healing composition" or "bioadhesive sealant" or "fibrin glue" means an agent or a composition that is able to promote and/or increase the speed and/or quality of cicatrisation of a wound. Wound healants or sealants are able to promote tissue regeneration. The expression "wound" means any damaged tissue, for example following trauma or surgery. Wounds in mammals include for example bed sores, ulcers, lacerations and burns, graft sites (graft donor and acceptor sites), fistulas, periodontal tissue damages, diabetic non-healing wounds, consequences of traumas or any surgery act. In its general sense the expression is intended to also encompass skin damages where the skin surface presents some depression without necessarily a cut on its surface such as age-related tissue damages (e.g., wrinkles) and scars such as for example acne (especially after dermabrasion treatment) or rubella scars. The expression "PRP" means a platelet-rich plasma, preferably of mammal origin or human origin, more preferably autologous, prepared by the process of the invention in order to pellet and remove erythrocytes and concentrate the plasma in leucocytes, thrombocytes and adhesion proteins as compared to native whole blood. The expression "autologous" or "autogenic" or "autogenous" means an in-vivo method wherein a single donor's blood, tissue and/or cell is used and wherein the blood, tissue and/or cell extracted from this donor is intended for use on the same donor. As opposed, "allogeneic" methods are using blood, tissue and/or cell from one or more third parties for use on a donor ("homologous" or "heterologous"). An autologous product avoids some of the common problems associated with the use of biological materials from third parties, such as for example screening to assure that the donor was biologically or immunologically compatible with the patient and potential contamination with hepatitis, HIV, prion, Creutzfeldt-Jakob disease and the like. The expression "coagulation activator" means an agent, for example an enzyme, that is able to trigger or activate coagulation of plasma and platelet aggregation. A coagulation activator comprises a thrombin activator and/or a fibrinogen activator and/or thrombin and/or an autologous thrombin and/or an autologous thrombin serum and/or calcium chloride and/or calcium gluconate. Coagulation may be combined in order to change the stiffness of compositions.

The expression "thrombin activator" means an agent that is able to activate thrombin and to trigger coagulation. Typical thrombin activators are certain co factors such as sodium or calcium. In practicing this invention, thrombin activation preferably occurs in the presence of calcium ions. Calcium ions are generally added to the platelet concentrate as a salt solution to provide a final concentration generally of or about 0.1 mg/mL of platelet concentrate. Suitable calcium salts include, without limitation, $CaCO_3$, $CaSO_4$ or $CaCl_2$. A preferred calcium salt for use in the invention is calcium gluconate (CaGL). CaGL is available as calcium gel injection, USP 10% (Regen Lab, Switzerland). The expression "fibrinogen activator" means an agent that is able to activate the conversion of fibrinogen into fibrin and triggers the formation of the clot. Typical fibrinogen activators are thrombin or batroxobin. The term thrombin may include calcified thrombin, in particular, from or about 100 to about 10 units of thrombin per 1 mL of 10% of aqueous calcium gluconate solution; it may include calcified bovine thrombin, allogeneic thrombin or recombinant human thrombin, preferably autologous thrombin. A fibrinogen activator can be an enriched thrombin composition such as thrombin compositions as described in U.S. Pat. No. 6,472,162 or an autologous thrombin serum according to the invention. The expression "therapeutically effective amount" means the amount or amounts of the constituent elements or combination thereof necessary to enhance wound healing such as, for example, the reduction in the volume or surface area of a wound, the increase in the amount of granulation tissue or other biological material facilitating collagen lay down, vascular in growth, fibroblast proliferation or overall healing. All of the versions of the invention described herein are assumed to have the therapeutically effective amount(s) of constituent substances, or combinations thereof. By the expression "pharmaceutically acceptable carrier" is intended pharmaceutically acceptable additional ingredients such as stabilizers, antimicrobial agents, buffers, adjuvants, anaesthetics, corticosteroids and the like. By the expression "cosmetically acceptable carrier" is intended cosmetically acceptable additional ingredients such as stabilizers, buffers, colouring agents, flavouring agents, adjuvants, and the like.

The expression "Cyclic Olefin Copolymer" (COC) or "Cyclic Olefin Polymer" (COP) means an amorphous polymer, Ethylene Copolymer; COC; COP; Cyclo Olefinecopolymer; Cyclic Olefin Polymer; Ethylene-norbornene Copolymer. COPs use a single type of monomer whereas COCs use different types of monomers. The invention encompasses cyclic olefin copolymers based on different types of cyclic monomers and polymerization methods. The Cyclic olefin copolymers or polymers of the present invention may be produced by chain copolymerization of cyclic monomers such as 8,9,10-trinorborn-2-ene (norbornene) or 1,2,3,4,4a,5,8,8a-octahydro-1,4:5,8-dimethanonaphthalene with ethene, Ticona's TOPAS, Mitsui Chemical's APEL, or by ring-opening metathesis polymerization of various cyclic monomers followed by hydrogenation (for example Japan Synthetic Rubber's ARTON, Zeon Chemical's Zeonex and Zeonor).

The expression "hyaluronic acid" (also called hyaluronan or hyaluronate) means an anionic, nonsulfated glycosaminoglycan distributed widely throughout connective, epithelial, and neural tissues. It is unique among glycosaminoglycans in that it is nonsulfated, forms in the plasma membrane instead of the Golgi, and can be very large, with its molecular weight often reaching the million. One of the chief components of the extracellular matrix, hyaluronan contributes significantly to cell proliferation and migration.

The expression "chitosan" means a linear polysaccharide composed of randomly distributed β-(1-4)-linked D-glucosamine (deacetylated unit) and N-acetyl-D-glucosamine (acetylated unit). Chitosan is produced commercially by deacetylation of chitin, which is the structural element in the exoskeleton of crustaceans (crabs, shrimp, etc.) and cell walls of fungi. The degree of deacetylation (% DD) can be determined by NMR spectroscopy, and the % DD in commercial chitosans is in the range 60-100%. On average, the molecular weight of commercially produced chitosan is between 3800 to 20,000 daltons. A common method for the synthesis of chitosan is the deacetylation of chitin using sodium hydroxide in excess as a reagent and water as a solvent. This reaction pathway, when allowed to go to completion (complete deacetylation) yields up to 98% product. The amino group in chitosan has a pKa value of ~6.5, which leads to a protonation in acidic to neutral solution with a charge density dependent on pH and the % DA-value. This makes chitosan water soluble and a bioadhesive which readily binds to negatively charged surfaces such as mucosal membranes. Chitosan enhances the transport of polar drugs across epithelial surfaces, and is biocompatible and biodegradable.

In one aspect, the invention provides a process or method for the preparation of thrombin serum, comprising the steps of:
a) Collecting whole blood preferably in a tube preferably containing a thixotropic gel,
b) Centrifuging the tube until liberation of thrombin serum, and
c) Collecting the thrombin serum.

The act of drawing blood initiates clotting reactions, and unless something is done to stop the process, a clot will naturally form.

Preferably, the thixotropic gel is located near the bottom of the tube. During centrifugation, the red blood cells will migrate under the gel. Meanwhile, polymerization of fibrinogen occurs with the formation of a clot on the gel. Under sufficient centrifuge force and/or sufficient centrifugation time, this clot will further precipitate forming a fibrin mesh which will liberate a liquid supernatant called serum comprising enriched activated thrombin. Thrombin is an enzyme stimulating coagulation.

Advantageously, a thrombin serum according to the invention can be obtained in a few steps only by simply centrifuging a tube containing whole blood and a thixotropic gel during sufficient centrifugation time. Advantageously, the method for the preparation of thrombin serum according to the invention provides a ready to use thrombin serum.

The thrombin serum is herein also referred to as thrombin enriched preparation, thrombin enriched serum, enriched activated thrombin serum, enriched activated thrombin preparation, thrombin-rich activated serum, thrombin-rich activated preparation.

In another aspect, the invention provides a process or method for the preparation of thrombin serum, comprising the steps of:
a) Collecting whole blood preferably in a tube preferably containing a thixotropic gel,
b) Centrifuging the tube until red blood cells migrate under the thixotropic gel and preferably until formation of a fibrin mesh on the thixotropic gel, and
c) Collecting the supernatant or thrombin serum.

In one preferred embodiment of the invention, the centrifugation step is performed at a force of about 1500 g during approximately 30 minutes. In a further embodiment, the centrifugation step is performed at force between about 1000 g and up to about 2000 g for a time selected from about 20 min up to about 40 min, preferably at 1500 g for a time selected from about 25 min up to about 35 min, preferably at 1500 g for about 30 min.

Preferably, the centrifugation step is performed for a sufficient length of time until liberation of thrombin serum.

Advantageously, the methods of the present invention allow conservation of the liquid serum, the thrombin remaining soluble.

Standard methods consist in triturating the clot until liberation of thrombin serum. Advantageously, this step is not needed in the preparation of a thrombin serum according to the present invention. This alternative thrombin serum may also be used as a thrombin enriched preparation in the context of the invention.

Advantageously, no coagulation agent is used and, coagulation occurs spontaneously. This has the advantages of saving costs and simplifying the process. As no citrate is present in the tube, advantageously no coagulation agent (also referred to as restoring agent) is necessary to initiate coagulation. Advantageously, no ethanol solution and/or calcium chloride is required.

Advantageously, the process or method for the preparation of thrombin serum herein described is simple to perform, necessitating a reduced amount of time of human presence as no clot trituration is required, representing an economic advantage over old methods of preparation.

An alternative autologous thrombin serum to be used as a thrombin enriched preparation in the context of the invention is prepared by an old process which comprises the addition to a patient's whole blood sample (e.g., 10 mL)

collected in a tube, a 95% v. ethanol solution (e.g., 1 mL) and calcium chloride 10% (e.g., 1 mL). The mixture is then allowed to precipitate for about 30 min at room temperature. After 30 min, almost 80% of the anti-thrombin (among other proteins like fibrinogen) is precipitated; then the tube is centrifuged at or about 1500 g for about 8 to 10 min and the autologous thrombin serum is ready for use in combination with a platelet-rich concentrate.

Preferably, the invention provides a process or method for the preparation of autologous thrombin serum. Preferably, all the aspects and/or embodiments of the present invention are for autologous use. Accordingly, this invention provides a method for preparing a completely autologous thrombin serum wherein the donor and receiver is the same person or animal.

In one embodiment of the invention, the tube for the preparation of thrombin serum is made of glass, preferably a glass separator tube containing a polyester-based thixotropic gel.

In a most preferred embodiment, the method for the preparation of the thrombin serum uses a tube according to the invention wherein no citrate is added.

In another aspect, the invention provides a process or method for the preparation of a wound or tissue healing composition, comprising the steps of:
a) Collecting whole blood preferably in a tube preferably containing a thixotropic gel,
b) Centrifuging the tube preferably until liberation of thrombin serum,
c) Collecting the supernatant or thrombin serum, and
d) Admixing the thrombin serum with a PRP composition or an isolated platelet concentrate composition.

In another aspect, the invention provides a process or method for the preparation of a wound or tissue healing composition, a cell composition and/or a cell preparation comprising the steps of:
a) Collecting whole blood preferably in a tube preferably containing a thixotropic gel,
b) Centrifuging the tube preferably until liberation of thrombin serum,
c) Collecting the thrombin serum,
d) Admixing the thrombin serum with a PRP composition or an isolated platelet concentrate composition, and
e) Admixing the resulting composition of step d) with a cell extract, cell composition, TCP, chitosan, hyaluronic acid, cream, cream mask, fat cells, fat tissue, bone marrow concentrate, lubricin, cd-gelatin, botulinum toxin and/or stem cells.

In one embodiment, the whole blood is collected into at least one tube. The tube may herein be referred to as a separator tube. Preferably, all the methods and/or processes of the present invention may use one or more tubes according to the invention.

In one embodiment, all the methods and/or processes of the present invention may use the whole blood collected in a blood bag system or blood collection tubes device according to the invention or a device or kit comprising such a blood bag system or blood collection tubes device.

An "empty" tube refers herein to a tube wherein no substances, no compositions or else have been inserted and/or added into the tube.

Any process or method of the present invention may be prepared using at least one tube according to the invention.

In another aspect, the invention provides a process or method for the preparation of a wound healant composition or tissue healant composition, comprising the steps of:
a) Collecting whole blood in a tube,
b) Centrifuging the tube, and
c) Collecting the clot.

Advantageously, no coagulation agent is used for the preparation of the wound healant composition or tissue healant composition. Advantageously, the wound healant composition or tissue healant composition represents a ready to use composition. Such composition may be directly applied on diabetic ulcers.

Preferably, the process or method for the preparation of a wound healant composition or tissue healant composition is for use in dentistry and/or orthopedics. In another aspect, the invention provides a wound healant composition or tissue healant composition comprising a clot for use in dentistry, orthopedics, arthritis, pseudo-arthritis or else. In one embodiment, the wound healant composition or tissue healant composition comprising the clot is applied in a dental cavity, on a diabetic ulcer, perforating ulcer, diabetic perforating ulcer, or else. Method of treatment and use of the healant composition or tissue healant composition comprising a clot is also encompassed by the invention.

In one embodiment, the wound healant composition or tissue healant composition may be combined with tricalcium phosphate (TCP) or with any bone substitute preferably before the formation of the clot.

The wound healant composition comprising TCP may preferably be prepared in a vial.

In one embodiment, the wound healant composition or tissue healant composition may be combined with hyaluronic acid (HA) preferably before the formation of the clot.

In another aspect, the present invention provides a method or process for the preparation of a platelet concentrate composition or platelet-rich plasma composition, comprising the steps of:
a) Centrifuging whole blood in a tube according to the invention preferably comprising sodium citrate and/or a thixotropic gel, and
b) Collecting the platelet-rich plasma.

The centrifugation step will eliminate the Red Blood Cells (RBCs) from the plasma. The top phase is a platelet rich plasma (PRP), and the bottom phase is anticoagulated whole blood minus the platelet rich plasma.

Preferably, the centrifugation step is performed at a force of or about 1500 g up to about 2000 g. Preferably, the centrifugation step is performed for a sufficient length of time to form a barrier between the plasma containing the platelets, the lymphocytes and the monocytes and the gel containing the erythrocytes.

Preferably, the separation step b) is made by collecting the supernatant from the top of said barrier. In one embodiment, the enriched platelet rich plasma is separated from the full plasma by removing half of the supernatant containing the platelet poor plasma. Preferably, the enriched plasma is enriched in leucocytes, thrombocytes and adhesion proteins (for example, fibronectin (soluble protein) or vitronectin (protein secreted by platelets)) as compared to native whole blood.

In one embodiment, the tube used for the preparation of platelet rich plasma is selected from:
i) a glass separator tube containing a polyester-based thixotropic gel and a buffered sodium citrate solution at 0.10 M,
ii) a polyethylene terephthalate separator tube containing a highly thixotropic gel formed by a polymer mixture and an anhydrous sodium citrate at 3.5 mg/mL,
iii) a Cyclic Olefin Copolymer (COC) or Cyclic Olefin Polymer (COP) separator tube containing a polyester-based thixotropic gel and a buffered sodium citrate solution at 0.10 M, or iv) a Cyclic Olefin Copolymer (COC) or Cyclic Olefin Polymer (COP) filter separator tube containing a buffered sodium citrate solution at 0.10 M or an anhydrous sodium citrate at 3.5 mg/mL.

In a most preferred embodiment, the method for the preparation of a platelet concentrate uses a tube according to the invention with the addition of citrate (for example a buffered sodium citrate solution at 0.10 M or an anhydrous sodium citrate at 3.5 mg/mL).

In another aspect, the present invention provides a method or process for the preparation of a wound healant or tissue healant composition, comprising the steps of:
 a) Centrifuging whole blood in a tube according to the invention preferably comprising sodium citrate and/or a thixotropic gel,
 b) Collecting the platelet-rich plasma, and
 c) Admixing the platelet-rich plasma with a cell extract, cell composition, TCP, chitosan, hyaluronic acid, cream, cream mask, fat cells, fat tissue, bone marrow concentrate, lubricin, cd-gelatin, botulinum toxin and/or stem cells.

In another aspect, the present invention provides a wound healant or tissue healant composition comprising:
 a) a platelet-rich plasma or plasma concentrate according to the invention and
 b) TCP, chitosan, hyaluronic acid, cream, cream mask, fat cells, fat tissue, bone marrow concentrate, lubricin, cd-gelatin, botulinum toxin and/or stem cells.

In another aspect, the present invention provides a wound healant or tissue healant composition comprising:
 a) a thrombin serum according to the invention,
 b) a platelet-rich plasma or plasma concentrate preferably according to the invention, and
 c) TCP, chitosan, hyaluronic acid, cream, cream mask, fat cells, fat tissue, bone marrow concentrate, lubricin, cd-gelatin, botulinum toxin and/or stem cells.

The formation of a clot is a multi-step process or cascade and several of these steps require the presence of calcium ions. By removing the calcium ions present in whole blood, as is the effect when the blood is collected in citrate, the blood can be prevented from clotting. A calcium chelating agent is a chemical that reacts with the calcium, present in blood, in such a fashion that the calcium can no longer function in blood coagulation. The most common chelating agent is a salt of citric acid (citrate), since it has the fewest side effects on the components of the clotting system. By collecting blood into a medium containing a calcium chelating agent such as citrate, sample collection and further preparations of the citrated sample can be performed over a time period of up to several hours. Preferred calcium chelating agent is sodium citrate.

While a 3.5 mg/ml sodium citrate collection medium is that which is frequently used to collect and preserve blood, the person skilled in this art will recognize that the ratio of sodium citrate to whole blood could be in a different range.

In another aspect, the present invention provides an isolated platelet concentrate composition comprising:
 a) plasma;
 b) platelets at a concentration of at least $300 \times 10^9$ cells/L;
 c) white blood cells at a concentration of at least $7 \times 10^9$ cells/L;
 d) fibrinogen at a concentration of at least 3 mg/L;
and wherein the erythrocyte concentration is less than $0.6 \times 10^{12}$ cells/L.

A platelet rich plasma composition is also referred to herein as plasma concentrate composition.

In one embodiment, a platelet concentrate composition or platelet rich plasma composition according to the invention may be combined with tricalcium phosphate (TCP) and/or any one substitute for use as volume corrector (TCP at 10-30 microns), in dentistry, orthopedics (TCP at 50 microns).

In another aspect, the present invention provides a method or process for the preparation of a wound healant composition or tissue healant composition, comprising the steps of:
 a) Centrifuging whole blood in a tube comprising hyaluronic acid,
 b) Optionally separating the enriched platelet rich plasma and hyaluronic acid from the full plasma, and
 c) Optionally mixing the enriched platelet rich plasma and hyaluronic acid.

Figure 16:
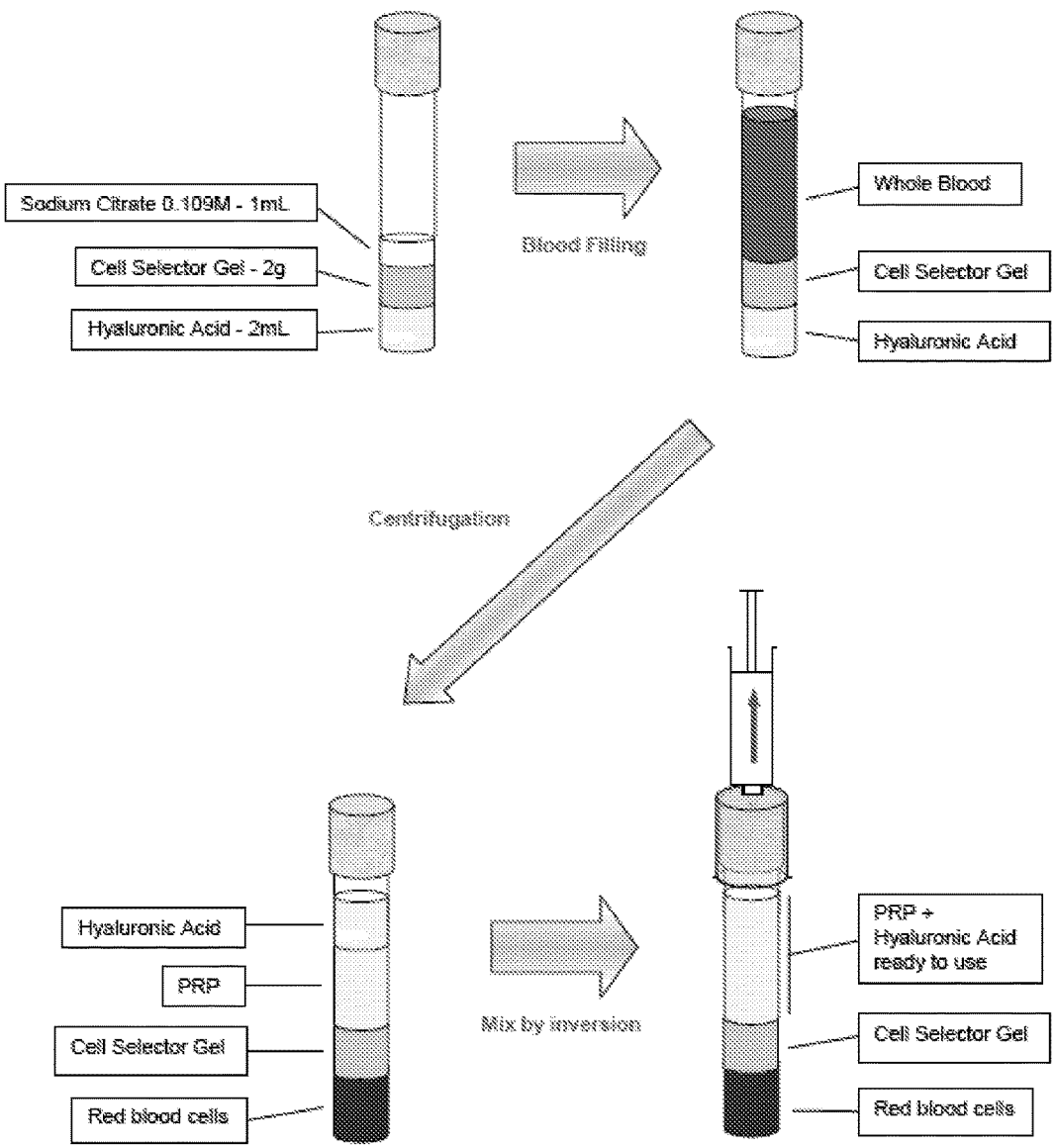
FIG. 16 is a schematic representation of the method for preparing a wound or tissue healing composition comprising PRP and hyaluronic acid.

Preferably, the tube comprises hyaluronic acid, preferably at the bottom of the tube, followed by a thixotropic gel and then an anticoagulant, preferably sodium citrate (FIG. 16).

Preferably, the separation step b) is made by collecting the supernatant containing the enriched platelet rich plasma and hyaluronic acid from the top of said barrier. In one embodiment, the enriched platelet rich plasma and hyaluronic acid is separated from the full plasma by removing half of the supernatant containing the platelet poor plasma. Preferably, the enriched plasma is enriched in leucocytes, thrombocytes and adhesion proteins (for example, fibronectin (soluble protein) or vitronectin (protein secreted by platelets)) as compared to native whole blood.

In another aspect, the invention provides a process or method for the preparation of a wound healant composition or tissue healant composition, comprising the steps of:
 a) Collecting whole blood preferably in a tube containing hyaluronic acid, a thixotropic gel and/or an anticoagulant preferably sodium citrate,
 b) Centrifuging the tube preferably until migration of red blood cells under the thixotropic gel and preferably until migration of hyaluronic acid above the enriched plasma,
 c) Optionally mixing the hyaluronic acid and the enriched plasma, preferably by inverting the tube,
 d) Collecting the supernatant containing hyaluronic acid and the enriched plasma, and
 e) Optionally further mixing said hyaluronic acid and said enriched plasma.

In another aspect, the invention provides a process or method for the preparation of a wound healant composition or tissue healant composition, comprising the steps of:
 a) Collecting whole blood preferably in a tube containing hyaluronic acid, a thixotropic gel and/or an anticoagulant preferably sodium citrate,
 b) Centrifuging the tube preferably until formation of a hyaluronic acid layer as first layer from the top of the tube followed by a second layer consisting of enriched plasma or PRP,
 c) Optionally mixing the hyaluronic acid and the enriched plasma, preferably by inverting the tube,
 d) Collecting the supernatant containing hyaluronic acid and the enriched plasma, and
 e) Optionally further mixing said hyaluronic acid and said enriched plasma.

The centrifugation step will eliminate the Red Blood Cells (RBCs) from the plasma. After centrifugation, the top phase is hyaluronic acid with underneath a platelet rich plasma (PRP), followed by the thixotropic gel and the bottom phase is anticoagulated whole blood containing the red blood cells minus the platelet rich plasma (FIG. 16). During centrifugation, hyaluronic acid migrates above plasma (FIG. 16).

Preferably, the tube contains about 1 ml to about 2 ml of hyaluronic acid, about 2 g of cell selector or thixotropic gel and about 1 ml of sodium citrate at 0.109M.

A schematic representation of the method for the preparation of a wound healant composition comprising hyaluronic acid and PRP is provided in FIG. 16.

Preferably, the enriched platelet rich plasma and hyaluronic acid are mixed by simple inversion of the tube.

Advantageously, when mixing the enriched platelet rich plasma and hyaluronic acid, the hyaluronic acid expands itself inflated by plasma and cells.

Advantageously, the wound healant composition or tissue healant composition obtained is a ready to use composition. Advantageously, the wound healant composition or tissue healant composition obtained is a viscous gel or biological glue suitable for injection, and for example may be used as mechanical support or filler.

Advantageously, the method or process for the preparation of a wound healant composition, tissue healant composition or viscous gel is economical, simple and rapid.

Preferably, the centrifugation step is performed for a sufficient length of time till migration of red blood cells under the thixotropic gel and preferably until migration of hyaluronic acid above the enriched plasma.

In one preferred embodiment of the invention, the centrifugation step is performed at a force of about 1500 g during approximately 5 minutes. In a further embodiment, the centrifugation step is performed at force between about 1000 g and up to about 2000 g for a time selected from about 3 min up to about 7 min, preferably at 1500 g for a time selected from about 3 min up to about 7 min.

In another aspect, the invention provides a tube comprising hyaluronic acid and an anticoagulant. In another aspect of the invention, the invention provides a tube comprising hyaluronic acid, an anticoagulant and whole blood. Preferably, the anticoagulant is sodium citrate.

In another aspect, the invention provides a tube comprising hyaluronic acid and a cell selector gel. In another aspect, the invention provides a tube comprising hyaluronic acid, a cell selector gel and whole blood. Preferably, the cell selector gel is a thixotropic gel.

In another aspect, the invention provides a tube comprising hyaluronic acid, an anticoagulant and a cell selector gel. In another aspect, the invention provides a tube comprising hyaluronic acid, an anticoagulant, a cell selector gel and whole blood. Preferably, the anticoagulant is sodium citrate. Preferably, the cell selector gel is a thixotropic gel. Preferably, hyaluronic acid is located at the bottom of the tube, followed by a thixotropic gel and above an anticoagulant, preferably sodium citrate (FIG. 16).

In another aspect, the invention provides a tube comprising hyaluronic acid and PRP. In another aspect, the invention provides a tube comprising hyaluronic acid, PRP and a cell selector gel. In another aspect, the invention provides a tube comprising hyaluronic acid, PRP and an anticoagulant. In another aspect, the invention provides a tube comprising hyaluronic acid, PRP, an anticoagulant and a cell selector gel. Preferably, the anticoagulant is sodium citrate. Preferably, the cell selector gel is a thixotropic gel.

Preferably, a tube according to the invention is used in a method or process according to the invention.

In another aspect, the invention provides a composition comprising hyaluronic acid and PRP. In another aspect, the invention provides a composition comprising hyaluronic acid and PRP, wherein the composition is obtained by a method for the preparation of a wound healant composition or tissue healant composition according to the invention.

In another aspect, the invention provides a kit or medical device comprising a tube according to the invention.

In further embodiments, the invention provides a tube, which may be used for the preparation of a wound healant composition or tissue healant composition, selected from:

i) a glass separator tube containing a polyester-based thixotropic gel, a buffered sodium citrate solution at 0.10 M and hyaluronic acid, ii) a polyethylene terephthalate separator tube containing a highly thixotropic gel formed by a polymer mixture, an anhydrous sodium citrate at 3.5 mg/m and hyaluronic acid, iii) a Cyclic Olefin Copolymer (COC) or Cyclic Olefin Polymer (COP) separator tube containing a polyester-based thixotropic gel, a buffered sodium citrate solution at 0.10 M and hyaluronic acid, or iv) a Cyclic Olefin Copolymer (COC) or Cyclic Olefin Polymer (COP) filter separator tube containing hyaluronic acid and a buffered sodium citrate solution at 0.10 M or an anhydrous sodium citrate at 3.5 mg/mL.

In further preferred embodiments, the invention provides a tube according to the invention, which may be used for the preparation of a wound healant composition or tissue healant composition, further comprising citrate and hyaluronic acid (for example hyaluronic acid and a buffered sodium citrate solution at 0.10 M or an anhydrous sodium citrate at 3.5 mg/mL).

Preferably, no phthalates are used for human use.

Alternatively, hirudin, benzylsulfonyl-d-Arg-Pro-4-am idinobenzylam ide (BAPA), heparin, citrate, acid citrate dextrose (ACD), citrate-theophylline-adenosine-dipyridamole (CTAD) or potassium-ethylenediaminetetra-acid (EDTA) may be used as anticoagulants.

In another aspect, the present invention provides a wound healant composition or tissue healant composition comprising:

a) plasma;

b) platelets at a concentration of at least $300 \times 10^9$ cells/L;

c) white blood cells at a concentration of at least $7 \times 10^9$ cells/L;

d) fibrinogen at a concentration of at least 3 mg/L;

e) about 1 ml to about 2 ml of hyaluronic acid;

and wherein the erythrocyte concentration is less than $0.6 \times 10^{12}$ cells/L.

In one embodiment, a wound healant composition or tissue healant composition according to the invention may be combined with tricalcium phosphate (TCP) and/or any one substitute for use as volume corrector (TCP at 10-30 microns), in dentistry, orthopedics (TCP at 50 microns).

In one embodiment, a wound healant composition, a tissue healant composition, a haemostatic agent, a platelet concentrate composition, or a platelet rich plasma composition according to the invention may be combined in the blood collection tube with hyaluronic acid.

In another aspect, the invention provides a process or method for the preparation of a haemostatic agent, a wound healant composition or tissue healant composition, comprising the step of mixing a thrombin serum or thrombin serum according to the invention with a platelet rich plasma composition, wound healant composition or tissue healant composition according to the invention.

In another aspect, the present invention provides a process or method for the preparation of a wound healant composition, tissue healant composition or haemostatic agent comprising:

a) Providing a platelet concentrate or platelet concentrate of the invention, b) Admixing the platelet concentrate with a coagulation activator, thrombin serum or thrombin serum according to the invention, and c) Optionally admixing a cell extract, such as extract of keratinocytes, bone marrow, fibroblasts, periosteum or corneal cells, melanocytes and Langerhans cells; fat cells; muscle cells such as myoblasts and satellite cells; osteoblasts; chondrocytes; blood progenitor cells, umbilical cord cells; mesenchymal stem cells (MSCs), preadipocytes, pre-endothelial cells, Schwann cells or Achilles tendon cells.

Preferably, an autologous platelet concentrate, an autologous thrombin and/or an autologous cell extract is/are used. More preferably, an autologous platelet concentrate and an autologous thrombin and an autologous cell extract are used. Preferably, tubes according to the invention are used.

In another aspect, the present invention provides a process or method for the preparation of a wound healant composition or tissue healant composition or haemostatic agent comprising:

a) Admixing a platelet concentrate with an autologous thrombin serum according to any aspects of the invention, and b) Optionally admixing at least one autologous cell extract, such as extract of keratinocytes, bone marrow, fibroblasts, periosteum or corneal cells, melanocytes and Langerhans cells; fat cells; muscle cells such as myoblasts and satellite cells; osteoblasts; chondrocytes; umbilical cord cells; mesenchymal stem cells (MSCs), preadipocytes, pre-endothelial cells, Schwann cells or Achilles tendon cells.

In another aspect, the present invention provides a process or method for the preparation of a wound healant composition or tissue healant composition or haemostatic agent comprising:

a) Admixing an autologous platelet concentrate with a thrombin serum, wherein the autologous platelet concentrate and/or the thrombin serum are prepared using tubes according to the invention, and b) Optionally admixing at least one autologous cell extract, such as extract of keratinocytes, bone marrow, fibroblasts, periosteum or corneal cells, melanocytes and Langerhans cells; fat cells; muscle cells such as myoblasts and satellite cells; osteoblasts; chondrocytes; umbilical cord cells; mesenchymal stem cells (MSCs), preadipocytes, pre-endothelial cells, Schwann cells or Achilles tendon cells.

In another aspect, the present invention provides a process or method for the preparation of a wound healant composition or tissue healant composition or haemostatic agent comprising:

a) Providing a platelet concentrate, preferably an autologous platelet concentrate according to the invention, b) Admixing the platelet concentrate with a thrombin serum, preferably an autologous thrombin according to the invention, and c) Optionally admixing at least one cell extract, preferably an autologous cell extract, such as extract of keratinocytes, bone marrow, fibroblasts, periosteum or corneal cells, melanocytes and Langerhans cells; fat cells; muscle cells such as myoblasts and satellite cells; osteoblasts; chondrocytes; umbilical cord cells; mesenchymal stem cells (MSCs), preadipocytes, pre-endothelial cells, Schwann cells or Achilles tendon cells.

Preferably, the invention provides a method or process for the preparation of an autologous wound healant composition or tissue healant composition or haemostatic agent. An autologous wound healant composition or tissue healant composition or haemostatic agent herein means a composition wherein either the platelet concentrate or thrombin serum is autologous.

In a most preferred aspect, the invention provides a method or process for the preparation of a completely autologous wound healant composition or tissue healant composition or haemostatic agent. A completely autologous wound healant composition or tissue healant composition or haemostatic agent herein means a composition wherein both the platelet concentrate or thrombin serum are autologous. In this preferred aspect of the invention, all of the blood components for the wound healant composition or tissue healant composition or haemostatic agent are derived from the same patient or animal to whom the wound healant composition or tissue healant composition or haemostatic agent will be applied.

In another aspect, the invention provides a method or process for the preparation of a completely autologous wound healant composition or tissue healant composition or haemostatic agent in combination with at least one autologous cell extract. In this aspect, the platelet concentrate, the thrombin serum and the cell extract(s) are all autologous and are therefore all derived from the same patient or animal.

In another aspect, the present invention provides a process or method for the preparation of an autologous wound healant composition or autologous tissue healant composition or autologous haemostatic agent comprising:

a) Mixing an autologous platelet concentrate, preferably an autologous platelet concentrate according to the invention, with an autologous thrombin serum, preferably an autologous thrombin according to the invention, and b) Optionally admixing at least one cell extract, such as extract of keratinocytes, bone marrow, fibroblasts, periosteum or corneal cells, melanocytes and Langerhans cells; fat cells; muscle cells such as myoblasts and satellite cells; osteoblasts; chondrocytes; umbilical cord cells; mesenchymal stem cells (MSCs), preadipocytes, pre-endothelial cells, Schwann cells or Achilles tendon cells, wherein the autologous platelet concentrate and the autologous thrombin are both derived from the same patient or same animal.

In another aspect, the present invention provides a process or method for the preparation of an autologous wound healant composition or autologous tissue healant composition or autologous haemostatic agent comprising:

a) Mixing an autologous platelet concentrate, preferably an autologous platelet concentrate according to the invention, with an autologous thrombin serum, preferably an autologous thrombin according to the invention, and b) Optionally admixing at least one autologous cell extract, such as extract of keratinocytes, bone marrow, fibroblasts, periosteum or corneal cells, melanocytes and Langerhans cells; fat cells; muscle cells such as myoblasts and satellite cells; osteoblasts; chondrocytes; umbilical cord cells; mesenchymal stem cells (MSCs), preadipocytes, pre-endothelial cells, Schwann cells or Achilles tendon cells, wherein the autologous platelet concentrate, the autologous thrombin and the autologous cell extract are all derived from the same patient or same animal.

The platelet rich plasma, autologous platelet rich plasma, thrombin serum, autologous thrombin serum, wound healant composition or tissue healant composition or haemostatic agent of the present invention may be combined with one or more cell extracts. In one embodiment, the cell extract is selected from keratinocytes, bone marrow, fibroblasts, periosteum or corneal cells, melanocytes and Langerhans cells; fat cells; muscle cells such as myoblasts and satellite cells; osteoblasts; chondrocytes; umbilical cord cells; mesenchymal stem cells (MSCs), preadipocytes, pre-endothelial cells, Schwann cells or Achilles tendon cells.

A wound healant composition or tissue healant composition or haemostatic agent of the present invention will stimulate cellular regeneration, acting as a biological glue in order to promote tissue adhesion.

In one embodiment, instead of thrombin serum, an alternative coagulation activator may be used such as calcium chloride, preferably calcium gluconate.

In one embodiment, multiple coagulation activators may be used in combination, preferably thrombin serum with calcium gluconate.

Preferably, the coagulation activator or thrombin serum is admixed with the platelet concentrate in a vol. ratio (platelet concentrate:coagulation activator) of about 10:1 up to about 10:3.

In a preferred embodiment of the invention, the liquid serum is collected in a 1:1 proportion, 3:1 proportion or a 10:1 proportion to the platelet rich plasma. The specific proportion used will alter the haemostatic agent stiffness. In a 3:1 proportion, a strong haemostatic agent is obtained. With a 10:1 proportion, a softer agent is obtained.

In one embodiment, the PRP or plasma concentrate alone or in combination with a cell extract, as well as preparations or compositions of the present invention may be combined or integrated with a soak acellular matrix to be applied directly on a wound, or may be cultivated in laboratory before application. A colagene matrix or synthetic matrix may be used, for example the Integra matrix.

Another embodiment contemplates mixing human recombinant thromboplastin directly with a platelet rich plasma to form a wound healant composition or tissue healant composition or haemostatic agent. Alternatively, human recombinant thromboplastin is utilized to generate thrombin in a small aliquot of plasma and then the resulting thrombin is combined with the platelet rich plasma to form a wound healant composition or tissue healant composition or haemostatic agent.

In one embodiment, the tubes used may have either wettable surfaces (such as, silica, diatomaceous earth, kaolin, etc.) or non-wettable surfaces (such as plastic, siliconized glass, etc.). Since surfaces play a role in activating blood coagulation, the surface of the separator tube chosen is dependent on whether clot formation is desired quickly or slowly. Chemical activators, such as kaolin, can also be used to speed up the clotting time; however, their subsequent removal would also be necessary.

Advantageously, the preparation of platelet rich plasma, platelet concentrate, thrombin serum, wound healant composition or tissue healant composition or haemostatic agent of the present invention do not necessitate the presence of ethanol and/or calcium. By using autologous thrombin according to the invention, the present invention doesn't necessitate restoring the clot-forming process. As such, no agent (or restoration agent) such as calcium chloride or calcium gluconate is required to reverse the effects of the anticoagulation agent (in restoring the coagulation activity of citrated blood).

Although calcium chloride is the well-known calcium salt for use as restoration agent, any calcium salt which functions in a similar manner to calcium chloride may be considered as restoration agent. Similarly, although many blood coagulation reactions are currently believed to require calcium ions as cofactors, any substance that is known or subsequently found to be functionally equivalent to calcium in facilitating these coagulation reactions may be considered as restoration agent, either individually or in combination with calcium. If the anticoagulation agent used was heparin, then heparinase would be used as restoration agent to reverse the effect of the anticoagulation agent.

Advantageously, the invention provides a platelet rich plasma, platelet concentrate, thrombin serum, wound healant composition or tissue healant composition or haemostatic agent wherein the risks associated with the use of bovine and recombinant human thrombin are eliminated.

Advantageously, a higher concentration of PRP, growth factors, leukocytes, fibrinogen and/or other proteins is obtained with the methods of the invention. Advantageously, a 2 fold concentration of PRP, growth factors, leukocytes, fibrinogen and/or other proteins is obtained in comparison with normal hematological levels.

Advantageously, the methods of the present invention confer an optimum cellular productivity for cellular expansion.

Advantageously, the methods of the present invention permit manipulation of the blood in an entirely closed circuit during the entire process, from blood collection, manipulation until application or injection to the patient. All the devices and kits are therefore adapted for an entirely closed circuit manipulation in order to avoid direct contact of the blood with air.

Advantageously, the methods of the present invention reduce oxidative stress and reduce manipulation time ex-vivo.

Advantageously, the methods of the present invention permit the formation of a solid autologous suturable membrane composed of aggregated platelets and activated polymerized fibrinogen.

The preparations of the present invention (for example bone marrow cell preparation) may be used alone or then admixed to the platelet concentrate according to the invention or centrifuged again with calcium gluconate to form a suturable membrane and applied or injected with an applicator to the injured site of the patients.

A bone marrow cell preparation according to the invention is useful for the treatment of bone defect or cartilage defect. The bone cell preparation may be used alone or in combination with a plasma concentrate according to the invention. A cartilage membrane may be used as well with calcium gluconate.

In one preferred embodiment of the invention, the centrifugation step (e.g., for the suturable membrane) is performed at a force of about 3000 g during 15 to 25 minutes. In one embodiment, the centrifugation step is performed at a force between about 2500 g and up to about 3500 g for a time selected from about 10 min up to about 30 min.

In one embodiment of the invention, the whole blood is collected from a human being or animal. A preferred embodiment of the invention is to collect the whole blood from a human being.

In another aspect, the present invention provides a wound or tissue healant composition or haemostatic agent prepared according to the invention comprising:

a) plasma;
b) platelets at a concentration of at least $300 \times 10^9$ cells/L;
c) white blood cells at a concentration of at least $7 \times 10^9$ cells/L;
d) fibrinogen at a concentration of at least 3 mg/L;
e) coagulation activator, autologous thrombin serum or autologous thrombin serum according to the invention,
f) optionally an autologous cell extract, such as an extract of keratinocytes, bone marrow cells, osteoblasts; chondrocytes, fibroblasts, periosteum or corneal cells, melanocytes and Langerhans cells; fat cells; muscle cells such as myoblasts and satellite cells; umbilical cord cells; mesenchymal stem cells (MSCs), preadipocytes, pre-endothelial cells, Schwann cells, tendon cells or pancreas islet cells; and wherein the erythrocyte concentration is less than $0.6 \times 10^{12}$ cells/L.

In another aspect, the present invention provides a wound or tissue healant composition or haemostatic agent comprising:
 a) plasma;
 b) platelets at a concentration of at least $300 \times 10^9$ cells/L;
 c) white blood cells at a concentration of at least $7 \times 10^9$ cells/L;
 d) fibrinogen at a concentration of at least 3 mg/L;
 e) autologous thrombin serum according to the invention;
 f) optionally an autologous cell extract, such as an extract of keratinocytes, bone marrow cells, osteoblasts; chondrocytes, fibroblasts, periosteum or corneal cells, melanocytes and Langerhans cells; fat cells; muscle cells such as myoblasts and satellite cells; umbilical cord cells; mesenchymal stem cells (MSCs), preadipocytes, pre-endothelial cells, Schwann cells, tendon cells or pancreas islet cells; and wherein the erythrocyte concentration is less than $0.6 \times 10^{12}$ cells/L.

Preferably, the coagulation activator or autologous thrombin serum is in a vol. ratio (platelet concentrate:coagulation activator) of about 10:1 to about 10:3.

Advantageously, the plasma of the present invention represents an ideal cell culture medium over known ones. Advantageously, the plasma of the present invention represents an ideal medium for the transport of cells. Accordingly, the plasma of the present invention contains all the cells and growth factors for an optimum cell growth and survival. Accordingly, the plasma of the present invention represents a very suitable medium for the implantation of cells to a patient, for example as an atopic application like surgical wounds, for anti-age injections, intra-articular injections, intra-muscular injections, or for pancreas regeneration (pancreatic islets).

In another aspect, the present invention provides a device for the preparation of a platelet concentrate composition or platelet rich plasma composition or haemostatic agent or wound or tissue healant composition or autologous thrombin serum according to the invention.

In another aspect, the present invention provides a device comprising at least one tube according to the invention.

Preferably, the device has an inlet for introducing said whole blood, is held in a vacuum intended to aspirate the whole blood sample, is sterile, has a usable vacuum of or about 8 to about 10 mL and is suitable for undergoing centrifugation.

In another aspect, the present invention provides a use of a platelet concentrate composition or platelet rich plasma composition or haemostatic agent or wound or tissue healant composition or thrombin serum according to the invention for the manufacture of a medicament for healing of wounds or for promoting bone or periodontum growth and/or bone and/or tissue regeneration.

In another aspect, the present invention provides a use of platelet concentrate composition or platelet rich plasma composition or haemostatic agent or wound or tissue healant composition or thrombin serum according to the invention for the manufacture of a cosmetic preparation for use as anti-aging agent or skin repairing agent such as a scar repairing agent, a wrinkle filling and/or repairing agent.

In another aspect, the invention provides a platelet concentrate composition or platelet rich plasma composition or haemostatic agent or wound healant composition or tissue healant composition or thrombin serum according to the invention for use as cosmetic preparation, esthetic preparation, aging management, volume corrector, wrinkle feeling, brown spot reduction and/or hair stimulator. In one embodiment, the platelet concentrate composition or platelet rich plasma composition or haemostatic agent or wound healant composition or tissue healant composition according to the invention is applied on and/or around the eyes, lips, eyelids, face, neck, chest, scalp, hair, hands and all the rest of the body and/or male and female genitalia.

In another aspect, the invention provides a platelet concentrate composition or platelet rich plasma composition or haemostatic agent or wound healant composition or tissue healant composition or thrombin serum according to the invention for use in ligament and/or cartilage reconstitution. Advantageously, ligament and/or cartilage reconstitution time using a composition of the present invention is divided by a factor 2 or 3 in comparison with known methods.

In one embodiment, the cosmetic preparation and/or esthetic preparation is combined with a cosmetic agent, cosmetic cream or cosmetic mask.

In another aspect, the present invention provides a pharmaceutical composition comprising a platelet concentrate composition or platelet rich plasma composition or haemostatic agent or wound or tissue healant composition or thrombin serum according to the invention and a pharmaceutically acceptable carrier.

In another aspect, the present invention provides a cosmetic composition comprising a platelet concentrate composition or platelet rich plasma composition or haemostatic agent or wound or tissue healant composition or thrombin serum according to the invention and a cosmetically acceptable carrier.

In another aspect, the present invention provides an implantable device for use in tissue regeneration therapy comprising:
 a) a permeable core comprising a platelet concentrate composition or platelet rich plasma composition or haemostatic agent or wound healant composition according to the invention optionally in combination with hyaluronic acid, and
 b) optionally an external jacket surrounding said core, said jacket comprising a biocompatible material, preferably bioresorbable, preferably hyaluronic acid.

In another aspect, the invention provides a kit comprising at least one tube according to the invention.

In another aspect, the invention provides a kit comprising a tube for the preparation of a platelet concentrate according to the invention and/or a tube for the preparation of thrombin serum according to the invention.

In another aspect, the invention provides a kit comprising at least one tube for the preparation of a platelet concentrate composition or platelet rich plasma composition or haemostatic agent or wound or tissue healant composition or thrombin serum according to the invention.

In one embodiment, the kit further comprises one or more tubes for the preparation of a platelet concentrate composition or platelet rich plasma composition or haemostatic agent or wound or tissue healant composition or thrombin serum according to the invention.

In one embodiment, the kit further comprises phlebotomy accessories for the preparation of the wound or tissue healant and an applicator device (e.g., a double syringe) for the simultaneous dispensation onto the wound of the platelet concentrate composition or platelet rich plasma composition or haemostatic agent or wound or tissue healant composition or thrombin serum according to the invention. In one embodiment, the kit is adapted for tissue regeneration.

In another aspect, the invention provides a method for promoting wound healing or tissue healing and/or sealing and/or tissue and/or bone regeneration in a wound or tissue of a human or animal comprising:

a) Providing a wound healant or tissue healant composition or haemostatic agent according to the invention, and b) Applying a therapeutically effective amount of the wound or tissue healant or haemostatic agent to a wound, a damaged tissue or a damaged bone.

In another aspect, the invention provides a method of treatment comprising:

a) Providing a wound healant or tissue healant composition or haemostatic agent according to the invention, and b) Applying a therapeutically effective amount of the wound or tissue healant or haemostatic agent to a wound, a damaged tissue or a damaged bone.

In another aspect, the invention provides a method for inducing periodontal regeneration in a wound or a periodontal defect of a mammal with periodontal disease or other condition requiring periodontal regeneration comprising:

a) Providing a wound or tissue healant or haemostatic agent according to the invention, b) Applying a therapeutically effective amount of the wound or tissue healant composition or haemostatic agent to the wound or tissue or the periodontal defect or cavity, c) Optionally inserting a periodontal barrier, and d) Closing the wound or tissue.

Preferably, the barrier is positioned between the gingival tissue and the wound or tissue treated according to steps a) and b). In one embodiment, the barrier is selected from a membrane, a biodegradable polymer and/or a biocompatible porous material.

The membrane may be obtained by combining PRP and calcium gluconate 10% in a proportion of 30 to 70 or 50 to 50 respectively. Centrifugation is performed during approximately 30 minutes.

In another aspect, the invention provides a method for promoting skin regeneration in a scar or a wrinkle from human or animal comprising:

a) Providing a wound or tissue healant composition or haemostatic agent according to the invention, and b) Filling the skin scar or wrinkle line with the said wound or tissue healant composition or haemostatic agent.

In another aspect, the present invention provides a process for the preparation of a cell composition, comprising the steps of:

a) Centrifuging whole blood in a tube according to the invention, b) Optionally separating the enriched platelet rich plasma from the full plasma, c) Re-suspending the enriched plasma, and d) Providing a cell extract such as an extract of dermal cells such as keratinocytes, fibroblasts, melanocytes and Langerhans cells; fat cells; bone marrow cells; muscle cells such as myoblasts and satellite cells; osteoblasts; chondrocytes; periosteal filter cells; corneal cells; umbilical cord cells; mesenchymal stem cells (MSCs), preadipocytes, pre-endothelial cells, Schwann cells, tendon cells or pancreas islet cells, and e) Admixing the platelet concentrate obtained under step c) with the cell extract obtained in d).

Preferably, the centrifugation step is performed at a force of or about 1500 g up to about 2000 g. Preferably, the centrifugation step is performed for a sufficient length of time to form a barrier between the plasma containing the platelets, the lymphocytes and the monocytes and the pellet containing the erythrocytes.

Preferably, the separation step b) is made by collecting the supernatant from the top of said barrier. In one embodiment, the enriched platelet rich plasma is separated from the full plasma by removing half of the supernatant containing the platelet poor plasma. Preferably, the enriched plasma is enriched in leucocytes, thrombocytes and adhesion proteins (for example, fibronectin) as compared to native whole blood.

In another aspect, the present invention provides a process for the preparation of a wound or tissue healing composition, comprising the steps of:

a) Centrifuging whole blood in a tube or in a separator tube according to the invention, b) Optionally separating the enriched platelet rich plasma from the full plasma, c) Re-suspending the enriched plasma, and d) Admixing the platelet concentrate obtained under step c) with a coagulation activator, thrombin serum, autologous thrombin serum or autologous thrombin serum according to the invention, e) Providing a cell extract such as an extract of dermal cells such as keratinocytes, fibroblasts, melanocytes and Langerhans cells; fat cells; bone marrow cells; muscle cells such as myoblasts and satellite cells; osteoblasts; chondrocytes; periosteal filter cells; corneal cells; umbilical cord cells; mesenchymal stem cells (MSCs), preadipocytes, pre-endothelial cells, Schwann cells, tendon cells or pancreas islet cells; and f) Admixing the platelet concentrate admixture obtained under step d) with the cell extract obtained in e).

Preferably, the centrifugation step is performed at a force of or about 1500 g up to about 2000 g. Preferably, the centrifugation step is performed for a sufficient length of time to form a barrier between the plasma containing the platelets, the lymphocytes and the monocytes and the pellet containing the erythrocytes.

Preferably, the separation step b) is made by collecting the supernatant from the top of said barrier. In one embodiment, the enriched platelet rich plasma is separated from the full plasma by removing half of the supernatant containing the platelet poor plasma. Preferably, the enriched plasma is enriched in leucocytes, thrombocytes and adhesion proteins (for example, fibronectin) as compared to native whole blood.

Preferably, the coagulation activator or autologous thrombin serum is in a vol. ratio (platelet concentrate:coagulation activator) of about 10:1 to about 10:3.

In another aspect, the present invention provides an isolated cell composition prepared according to the invention comprising:

a) plasma, b) platelets at a concentration of at least $300 \times 10^9$ cells/L, c) white blood cells at a concentration of at least $7 \times 10^9$ cells/L, d) fibrinogen at a concentration of at least 3 mg/L, and e) a cell extract, such as an extract of dermal cells such as keratinocytes, fibroblasts, melanocytes and Langherans cells; fat cells; bone marrow cells; muscle cells such as myoblasts and satellite cells; osteoblasts; chondrocytes; periosteal filter cells; corneal cells; umbilical cord cells; mesenchymal stem cells (MSCs), preadipocytes, pre-endothelial cells, Schwann cells, tendon cells or pancreas islet cells.

Preferably, the cells are at a concentration of about $10^5$ to about $10^6$ cells/ml of plasma or enriched plasma and the erythrocyte concentration is less than $0.6 \times 10^{12}$ cells/L.

In another aspect, the present invention provides an isolated cell composition prepared according to the invention comprising:

a) plasma, b) platelets at a concentration of at least $300 \times 10^9$ cells/L, c) white blood cells at a concentration of at least $7 \times 10^9$ cells/L, d) fibrinogen at a concentration of at least 3 mg/L, e) a coagulation activator, thrombin serum, autologous thrombin serum or autologous thrombin serum according to the invention, and f) a cell extract, such as an extract of dermal cells such as keratinocytes, fibroblasts, melanocytes and Langerhans cells; fat cells; bone marrow cells; muscle cells such as myoblasts and satellite cells; osteoblasts; chondrocytes; periosteal filter cells; corneal cells; umbilical cord cells; mesenchymal stem cells (MSCs), preadipocytes, pre-endothelial cells, Schwann cells, tendon cells or pancreas islet cells.

Preferably, the coagulation activator or autologous thrombin serum is in a vol. ratio (platelet concentrate:coagulation activator) of about 10:1 to about 10:3.

Preferably, the cells are at a concentration of about $10^5$ to about $10^6$ cells/ml of plasma or enriched plasma and the erythrocyte concentration is less than $0.6 \times 10^{12}$ cells/L.

In another aspect, the invention provides a wound or tissue healing composition or haemostatic agent comprising an isolated cell composition according to the invention.

In another aspect, the invention provides a method for promoting wound or tissue healing and/or sealing and/or regeneration of a tissue and/or a cartilage and/or a bone and/or a nerve in a human or an animal comprising:

a) Providing a wound or tissue healing composition, a haemostatic agent or a cell composition according to the invention, and b) Applying a therapeutically effective amount of the wound or tissue healing composition, haemostatic agent or cell composition to a wound, a damaged tissue or a damaged cartilage or a damaged bone.

In another aspect, the invention provides a method for increasing adipose tissue volume in a mammal with a dermal fat graft or other condition requiring adipose tissue regeneration comprising:

a) Providing a fat cell composition according to the invention, b) Applying a therapeutically or cosmetically effective amount of the fat cell composition in combination with PRP or plasma concentrate according to the invention to the dermal fat graft or the adipose tissue requiring adipose tissue regeneration, and c) Optionally inserting a surgical flap or implant, wherein the surgical flap or implant is positioned in the site requiring regeneration or volumetric amplification and the said surgical flap or implant comprises a combination of a fat cell preparation according to the invention and PRP, plasma concentrate or enriched plasma material.

In another aspect, the invention provides a method for inducing myocardial regeneration in a mammal with myocardial deficiency or other condition requiring myocardial tissue regeneration comprising:

a) Providing a muscle cell or a bone marrow cell composition according to the invention, and b) Applying a therapeutically effective amount of the muscle cell composition in combination with PRP or plasma concentrate according to the invention to the myocardial tissue requiring regeneration.

In another aspect, the invention provides a method for inducing corneal regeneration in a mammal with corneal deficiency or other condition requiring corneal regeneration comprising:

a) Providing a corneal cell composition according to the invention, and b) Applying a therapeutically effective amount of the corneal cell composition in combination with PRP or plasma concentrate according to the invention to the corneal tissue requiring regeneration.

In another aspect, the invention provides a method for inducing articular or cartilage regeneration in a mammal with articular or cartilage deficiency or other condition requiring articular or cartilage tissue regeneration comprising:

a) Providing a chondrocyte cell or bone marrow cell composition according to the invention, b) Applying a therapeutically effective amount of the chondrocyte cell composition in combination with PRP or plasma concentrate according to the invention to the articular or cartilage tissue requiring regeneration, and c) Optionally inserting a surgical flap or implant, wherein the surgical flap or implant is positioned in the defect of the cartilage or under a periosteal patch, and the surgical flap or implant comprises a combination of a chondrocyte or bone marrow cell composition according to the invention and PRP, plasma concentrate or enriched plasma material.

In another aspect, the invention provides a method for promoting skin regeneration in a scar, a wrinkle or a fat deficiency from human or lower animal comprising:

a) Providing a wound or tissue healing composition, a haemostatic agent or a cell composition in combination with PRP or plasma concentrate according to the invention, and b) Filling the skin scar, wrinkle line or fat deficiency with the wound or tissue healing composition, a haemostatic agent or a cell composition in combination with PRP or plasma concentrate according to the invention.

In another aspect, the invention provides a method for inducing peripheral nerve regeneration in a mammal with peripheral nerve damage, nerve suture or spinal cord injury or other condition requiring peripheral nerve regeneration comprising:

a) Providing a Schwann cell composition in combination with PRP or plasma concentrate according to the invention, and b) Applying a therapeutically effective amount of the Schwann cell composition in combination with PRP or plasma concentrate to the peripheral nerve requiring regeneration.

In another aspect, the invention provides a method for inducing bone regeneration in a mammal with bone damage, bone deficiency or other condition requiring bone regeneration comprising:

a) Providing a bone marrow cell or osteoblast cell composition in combination with PRP or plasma concentrate according to the invention, and b) Applying a therapeutically effective amount of the bone marrow cell or osteoblast cell composition in combination with PRP or plasma concentrate according to the invention to the bone requiring regeneration.

In another aspect, the invention provides a method for the treatment of type I diabetes, insulin-dependent diabetes or hyperglycaemia in a mammal comprising:

a) Providing a pancreas islet cell composition in combination with PRP or plasma concentrate according to the invention, and b) Applying a therapeutically effective amount of the pancreas islet cell composition in combination with PRP or plasma concentrate according to the invention to the patient, for example by injection.

In another aspect, the invention provides a method for the treatment of urinary incontinence in a mammal or other condition requiring bladder regeneration comprising:

a) Providing a myoblast cell composition in combination with PRP or plasma concentrate according to the invention, and b) Applying a therapeutically effective amount of the myoblast cell composition in combination with PRP or plasma concentrate according to the invention to the bladder neck requiring regeneration.

In another aspect, the invention provides a method for the treatment of anal incontinence in a mammal or other condition requiring anal muscle regeneration comprising:

a) Providing a myoblast cell composition in combination with PRP or plasma concentrate according to the invention, and b) Applying a therapeutically effective amount of the myoblast cell composition in combination with PRP or plasma concentrate according to the invention to the para-anal area requiring regeneration.

In another aspect, the invention provides a method for the treatment of reflux oesophagitis or gastro-oesophageal reflux disorders in a mammal or other condition requiring oesophageal sphincter regeneration comprising:

a) Providing a myoblast cell composition in combination with PRP or plasma concentrate according to the invention, and b) Applying a therapeutically effective amount of the myoblast cell composition in combination with PRP or plasma concentrate according to the invention to the oesophageal sphincter requiring regeneration.

In another aspect, the present invention provides a use of a wound or tissue healing composition, a haemostatic agent, a cell composition or a cell preparation according to the invention for the manufacture of a medicament for healing of wounds or tissues, mesotherapy, intramuscular, or for promoting bone or periodontum growth and/or bone and/or tissue regeneration such as skin, cartilage, muscle, tendon, adipose tissue, cornea, peripheral nerves, spine or bone regeneration.

In another aspect, the present invention provides a use of a wound or tissue healing composition, a haemostatic agent, a cell composition or a cell preparation according to the invention for the manufacture of a cosmetic preparation for use as anti-aging agent or skin repairing agent such as scar repairing agent, lipoatrophy repairing agent or wrinkle filling and/or repairing agent.

In another aspect, the present invention provides a pharmaceutical composition comprising a wound or tissue healing composition, a haemostatic agent, a cell composition or a cell preparation according to the invention and a pharmaceutically acceptable carrier.

In another aspect, the present invention provides a cosmetic composition comprising a wound or tissue healing composition, a haemostatic agent, a cell composition or a cell preparation according to the invention and a cosmetically acceptable carrier.

In another aspect, the present invention provides an implantable device for use in tissue regeneration therapy comprising:

a) a permeable core comprising a wound or tissue healing composition, a haemostatic agent, a cell composition or a cell preparation of the invention optionally in combination with hyaluronic acid, and b) an external jacket surrounding said core, said jacket comprising a biocompatible material, preferably bioresorbable, preferably hyaluronic acid.

In one embodiment, the compositions, wound or tissue healant compositions, cell extracts, cell compositions, plasma concentrate and thrombin preparations of the invention use allogeneic substances, compositions, blood or cells.

The uses, methods and compositions according to the invention are useful in the regeneration and/or rejuvenation of tissues, bones and/or cartilages. The uses, methods and compositions according to the invention are particularly useful in the treatment of diabetic neuropathic ulcers or decubitus sores; bone and cartilage damages such as deep joint cartilage or chondral damages such as surgical repair of torn tendons; arthritis in joint caused by traumas or by aging; rotator cuff disorders; non-healing wounds such as vasculitis induced wounds, for example in lower equine limb; periodontal diseases; implant surgery; cardiovascular, thoracic, transplantation, head and neck, oral, gastrointestinal, orthopedic, neurosurgical, and plastic surgery; mesotherapy and/or mesotherapy injections; cardiac muscle damages such as in chronic cardiac failure, heart failure, ischemic and non-ischemic disorders, cardiomyopathy; gastro-oesophageal reflux disease; anal or urinary incontinence; facial surgery such as facial surgery induced alopecia (alopecia due to hair follicle loss in the side burn areas), hair loss, alopecia, face-lift surgery (rhytidectomy), rhinoplasty, dermal fat grafts (in the treatment of facial augmentation, congenital hemiatrophy of the face such as congenital cartilage nose atrophy and lipoatrophy such as in HIV/AIDS suffering patients, genital dysfunction, erosion and arthroscopy); wound healing complications such as after eyelid blepharoplasty; corneal disorders such as corneal opacity such as those caused by chemical burns, affliction by Stevens-Johnson syndrome and corneal ulcers; scarring of the cornea; dry eye syndrome; haematological diseases such as Thalassaemia; peripheral nerve damage, nerve suture and spinal cord injury; bone defects or disorders such as bone graft or bone fracture, skin damages or disorders such as acne (especially after dermabrasion treatment), burns, rubella or small pox scars, vitiligo, lipoatrophy, Kaposi's sarcoma, skin keloids or Dupuytren's palmar fibromatosis.

The uses, methods and compositions according to the invention are useful in tissue healing, including bone regeneration and repair, mitogenesis, angiogenesis and/or macrophage activation.

Additional advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

The compositions, uses and methods according to the invention are particularly useful in haemostasis, in the regeneration, revitalization, hydration and/or stimulation of tissue, as biological glue, bioadhesive sealant or biological filler.

Advantageously, the strong biological glue of the present invention has a higher mechanical strength than other known ones, notably for all invasive surgical interventions. Such biological glues of the present invention have an increased capacity to cure damaged tissue by containing appropriate cells, platelets, leukocytes, growth factors and other factors reducing/preventing eventual infections.

The compositions, uses and methods according to the invention are particularly useful in wound care, surgery, injections for orthopedic and injections for esthetic, cosmetic or volume corrections.

In another aspect, the uses, methods and compositions according to the invention are useful in the regeneration and/or rejuvenation of skin tissues, particularly in promoting and/or initiating skin regeneration such as reducing skin wrinkles, deep wrinkles, acne (especially after dermabrasion treatment), burns, rubella or small pox scars, vitiligo and lipoatrophy (e.g., anti-aging compositions and skin regeneration compositions), amelioration of nasolabial lines and treatment of skin damages or disorders such as skin burns, Kaposi's sarcoma, skin keloids or Dupuytren's palmar fibromatosis, in the reduction of pain associated with skin and tissue regeneration, for hemorrhoidal cushion, erectile dysfunction, caverna, cavernosal fibrosis, Peyronie's disease, vagina and/or labia.

The compositions, uses and methods according to the invention are particularly useful in wound or tissue healing, regeneration treatments or sports medicine for the knee, elbow, (torn) muscles, spine, spinal disc, tendon, ligament, the treatment of traumatic or surgical wounds such as the fitting and/or holding and/or sealing of native or prosthetic grafts (especially skin, bone grafts and/or dental prostheses or implants or the like, including also the graft donor site); treatment of arthritis, gonarthritis, tendinitis, rotator cuff, treatment of vasculitis; ulcers such as diabetic neuropathic ulcers or decubitus sores; radiodermatitis (e.g., after irradiation on an epidermoidal skin carcinoma) and closing fistulas (such as for cyclists).

Further, the compositions, uses and methods according to the invention are particularly useful in the treatment of cardiac disorders, cardiac regeneration such as in the treatment of heart failure, chronic cardiac failure, ischemic and non-ischemic cardiac failure and cardiomyopathy.

Further, the compositions, uses and methods according to the invention are particularly useful in the treatment of urinary and/or anal incontinence.

Further, the compositions, uses and methods according to the invention are particularly useful in the treatment of reflux oesophagitis and/or gastro-oesophageal reflux disorder.

Further, the compositions, uses and methods according to the invention are particularly useful in the treatment of skin damages such as in skins damaged by radiation (radiodermatitis or sun damaged skin), aged skins or burned skins and/or in the amelioration of facial wrinkles, rhytids, acne (especially after dermabrasion treatment), burns, rubella or small pox scars, vitiligo, lipoatrophy or lipodystrophy, Kaposi's sarcoma, skin keloids or Dupuytren's palmar fibromatosis and/or in skin rejuvenation treatments.

Further, the compositions, uses and methods according to the invention are particularly useful in the treatment of lipoatrophy such as in HIV/AIDS patients and in other congenital hemiatrophy of the face such as congenital cartilage nose atrophy. Further, the compositions, uses and methods according to the invention are particularly useful in the treatment of bone, cartilage and articular disorders such as chondral damage, arthritis, cartilage and/or bone injury such as deep cartilage damage and/or erosion and/or arthroscopy, tendon torn and rotator cuff in shoulder.

Further, the compositions, uses and methods according to the invention are particularly useful in the treatment of hematological diseases such as Thalassaemia.

Further, the compositions, uses and methods according to the invention are particularly useful in the treatment of corneal disorders such as dry eye syndrome; corneal opacity such as those caused by chemical burns, affliction by Stevens-Johnson syndrome; scarring of the cornea and corneal ulcers.

Further, the compositions, uses and methods according to the invention are particularly useful in the treatment of peripheral nerve damage, nerve suture and spinal cord injury.

Further, the compositions, uses and methods according to the invention are particularly useful in the treatment of type I diabetes, insulin-dependent diabetes and/or hyperglycaemia.

Further, the compositions, uses and methods according to the invention are particularly useful in the treatment of bone defects or disorders such as bone graft or bone fracture.

The use of the resulting composition of the invention can be further modified before application and according to the therapeutic objective.

Compositions of the invention can be used together with bone filling materials, especially resorbable filling materials such as hydroxyapatite (calcium phosphate ceramic used as a biomaterial) or demineralised bone, or used as a mixture with bone extracts in a process for the regrowth of bone for example in craniofacial and orthopaedic procedures.

Depending on the use or disease, compositions of the invention can be used together with hyaluronic acid 10%, hyaluronic acid 20%, hyaluronic acid 30%, hyaluronic acid 40%, and/or hyaluronic acid 50%.

Compositions of the invention may be used as a wound sealant in plastic surgery including burn grafting and other free skin graft applications, for example in oncology for favouring tissue regeneration, including speeding (neo)vascularization. The compositions according to the invention are particularly useful in wound healing treatments at the skin graft donor site. The removal of a skin graft on a healthy skin creates a new wound at the donor's site which normally heals spontaneously between 12 to 14 days. However, this cicatrisation is extremely demanding for the body, especially if the donor site is broad or the person is less resistant (e.g., burn victims, people suffering from multiple traumas, people treated with corticoids, children or elderly) and the energetic losses are even increased by the loss in minerals, trace elements and proteins induced by the fluid losses from the new wound. In addition, important pain during the first 8 days is often present on the graft donor's site. Pain reduction treatments are often used such as the use of analgesics (e.g., morphine) and/or hydrocellular wound dressings, however pain remains present, especially during the dressing change that occurs imperatively within 48 hours up to 1 week after the graft removal. In addition, the hydrocellular wound dressings have the drawbacks not only to be rather expensive but also by maintaining humidity on the wound, to prevent its drying, to increase the wound deepness, to favour the outbreak of bacterial infections and to lead to non-esthetic scars. Therefore, a stimulation of the skin graft donor site healing is very desirable.

Compositions of the invention are particularly adapted to chronic wounds that may lack sufficient blood circulation to facilitate the wound healing cascade.

The compositions and methods according to the invention may be also used in the treatment of periodontal disease where a loss and/or a damage of the periodontal tissues is observed, such a treatment comprising for example placing at the periodontal site or cavity in a human or a lower animal in need of periodontal tissue regeneration a composition according to the invention.

The compositions according to this invention are effective in eliminating or greatly reducing post-operative bleeding and extravasation or loss of serous or other fluid in these applications, in reducing the infection risk caused by most bacteria and/or enhances connective tissue formation compared to natural healing (i.e., no exogenous agents added) or to healing obtained through the use of other platelet concentrates prepared with known methods. The compositions according to the invention are particularly useful in the preparation of pharmaceuticals for promoting and/or initiating wound healing and/or tissue regeneration or for the preparation of cosmetic compositions for skin regeneration such as reducing skin wrinkles, acne (especially after dermabrasion treatment), rubella or small pox scars, vitiligo and lipoatrophy (e.g., anti-aging compositions and skin regeneration compositions).

The compositions of the present invention may be administered locally or injected in the wound or in or near to the grafted organ or injected subcutaneously. Local administration may be by injection at the site of injury or defect or by insertion or attachment of a solid carrier at the site, or by admixture with a cream or emulsion, or by inclusion in a tissue or paper or hydrogel carrier, or by direct, topical application of the composition of the invention such as in the form of eye drops. Preferably, the compositions are readily syringable compositions. The mode of administration, the dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

The compositions of the present invention may be administered in combination with a co-agent useful in the treatment of tissue regeneration such as a healing agent, a wrinkle filler, an anti-aging agent such as an anti-aging vitamin complex, an antibacterial agent, antibiotic agent, a corticosteroid agent, an antalgic and analgesic agent, or an anesthetic agent like adrenaline, etc. The invention comprises compositions combined with a co-agent useful in the treatment of tissue regeneration for simultaneous, separate or sequential use in tissue regeneration therapy such as wound healing, bone and periodontum growth repair.

The compositions of the invention, the device and procedures for the preparation of autologous platelet concentrates or cell compositions of the invention are particularly useful for therapeutic use, particularly as autogenous biological glue in a haemostatic system intended to accelerate the physiological process of tissue regeneration, for example in dental implantology, skin and bone surgery, cartilage and tendon surgery, corneal and peripheral nerve regeneration and cardiac surgery. The compositions of the invention, the device and procedures for the preparation of autologous platelet concentrates and cell composition of the invention are particularly useful for cosmetic use, particularly as autogenous rejuvenation material intended to be used for example as wrinkle, scar or fat deficiency filler, alone or in combination with at least one anti-aging agent.

The platelet concentrate of the invention may be combined with an autologous cell extract preparation such as for example keratinocytes, bone marrow cells, osteoblasts, chondrocytes, fibroblasts, periosteum, melanocytes and Langerhans cells; fat cells; bone marrow cells; muscle cells such as myoblasts and satellite cells; periosteal filter cells; mesenchymal stem cells (MSCs), preadipocytes, pre-endothelial cells, corneal cells; umbilical cord cells; tendon cells or pancreatic islet cells. Keratinocytes can be harvested through a method described by Reinwald and Green, 1975, Cell, 6(3):331-43. Other mentioned cells can be harvested through methods described in "Culture de cellules animales; méthologies-applications", 2003, Ed. Barlovatz-Meimom and Adolphe, INSERM editions, Paris. Alternatively, cell extracts are derived from a cell bank or a cell culture or harvested as described in the Examples below.

The platelet concentrate and cell compositions of the invention have proven to be really beneficial in the acceleration and/or promotion of the healing process of wounds, even chronic unhealing wounds, leading to successful closures where weeks of conventional therapies had failed and achieving a decrease in infection risks, an improvement in patient's recovery and comfort, a reduction of medical care costs and a better esthetic final result.

The compositions of the invention can of course be also prepared from plasma derived from several identified donors. The invention is not limited to autologous biological materials, such as collection of concentrated platelets from the wounded's own biological material. The invention encompasses the use of biological materials obtained from one or more third parties, who need not be of the same species as the patient whose wound is being treated with the wound healant composition described herein unless bioincompatibility would result from the use of such third party biological materials. In one embodiment, the invention provides a process for the preparation of a platelet concentrate composition or a cell composition as described herein.

In another embodiment, the present invention provides a device for the preparation of a platelet concentrate composition from whole blood as described herein.

In a further embodiment, the invention provides a process for the preparation of a thrombin serum and/or platelet concentrate composition wherein the centrifugation step is performed at about 1500 g and up to about 1700 g for a time selected from about 3 min up to about 15 min, preferentially at 1500 g for about 8 min.

In another further embodiment, the invention provides a process for the preparation of a platelet concentrate composition wherein the tube has an inlet for introducing said whole blood, is held in a vacuum intended to aspirate the whole blood sample, is sterile, has a usable vacuum of 8 to 10 mL and is suitable for undergoing centrifugation.

In another further embodiment, the invention provides a process for the preparation of a platelet concentrate composition wherein the tube is a polyethylene terephthalate tube containing a highly thixotropic gel formed by a polymer mixture and an anhydrous sodium citrate at 3.5 mg/mL.

In another embodiment, the present invention provides an isolated platelet concentrate composition obtainable from the process according to the invention.

In another embodiment, the invention provides an isolated platelet concentrate composition obtained by a process according to the invention comprising:
 a) plasma,
 b) platelets at a concentration of at least $300 \times 10^9$ cells/L, preferably of at least $350 \times 10^9$ cells/L, more preferably of at least $400 \times 10^9$ cells/L,
 c) white blood cells at a concentration of at least $7 \times 10^9$ cells/L, preferably of at least $8 \times 10^9$ cells/L, and
 d) fibrinogen at a concentration of at least 3 mg/L.

Preferably, the erythrocyte concentration is less than $0.4 \times 10^{12}$ cells/L or $0.5 \times 10^{12}$ cells/L.

In another embodiment, the present invention provides a wound or tissue healant composition comprising:
 a) plasma,
 b) platelets at a concentration of at least $300 \times 10^9$ cells/L, preferably of at least $350 \times 10^9$ cells/L, more preferably of at least $400 \times 10^9$ cells/L,
 c) white blood cells at a concentration of at least $7 \times 10^9$ cells/L, preferably of at least $8 \times 10^9$ cells/L,
 d) fibrinogen at a concentration of at least 3 mg/L, e) a thrombin serum according to the invention, and f) optionally an autologous cell extract, such as extract of keratinocytes, bone marrow cells, fibroblasts, periosteum, melanocytes and Langerhans cells; fat cells; bone marrow cells; muscle cells such as myoblasts and satellite cells; osteoblasts; chondrocytes; mesenchymal stem cells (MSCs), preadipocytes, pre-endothelial cells, periosteal filter cells; corneal cells; umbilical cord cells; tendon cells or pancreatic islet cells.

Preferably, the coagulation activator or thrombin serum is in a vol. ratio (platelet concentrate:coagulation activator) of about 10:1 to about 10:3.

Preferably, the cells are at a concentration of about $10^5$ to about $10^6$ cells/ml of plasma or enriched plasma and the erythrocyte concentration is less than $0.4 \times 10^{12}$ cells/L or $0.5 \times 10^{12}$ cells/L.

In another embodiment, the invention provides a process for the preparation of a wound or tissue healant composition as described herein.

In another further embodiment, the invention provides a process for the preparation of a wound or tissue healant composition wherein the coagulation activator which is admixed is calcium gluconate or 10% calcium chloride.

In another further embodiment, the invention provides a process for the preparation of a wound or tissue healant composition wherein the coagulation activator which is admixed with a platelet concentrate (PRP) is a thrombin enriched preparation, which may further be combined with calcium gluconate or calcium chloride. A method for preparing thrombin for use in a biological glue is described in U.S. Pat. No. 6,472,162 by the addition of 8 to 20% ETOH to a volume of plasma and this preparation may be used as a thrombin enriched preparation in the context of the invention. Alternatively, an autologous thrombin serum (ATS) can be used as thrombin enriched preparation in the context of the invention. An alternative autologous thrombin serum according to the invention is obtained by a process comprising (i) the addition to a patient's whole blood sample (e.g., 8 mL) collected in a separator tube of the invention, a 10% of final volume of calcium chloride 10% (e.g., 1 mL) and a 10% of the final volume of a preparation of 95% v. ethanol solution (e.g., 1 mL) and (ii) precipitation for about 30 min at room temperature. After 30 min, a centrifugation at or about 1500 g for about 8 to 10 min is performed. In a further preferred embodiment, the thrombin enriched preparation and preferably the autologous thrombin serum according to the invention is admixed with a platelet concentrate (PRP) directly on the wound.

In another further embodiment, the invention provides a process for the preparation of a wound or tissue healant composition according to the invention further comprising a step b') wherein the activated platelet-rich preparation composition (obtained by the admixing of the platelet concentrate with the coagulation activator or autologous thrombin serum) obtained in step b) may be partially dehydrated by the contact of a wound dressing covered by a soft hydrophobic layer to avoid contamination with micro-strings from the dressing in order to obtain a semi-solid gel that can be manipulated by appropriate instruments, for example to fill a cavity or tissue deficiency, or as a growth matrix ("scaffold") while waiting for the reconstitution of the autogenous extracellular matrix. The obtained wound or tissue healant is particularly useful in a method for inducing periodontal regeneration in a wound, a tissue or a periodontal defect or a cavity.

In another further embodiment, the platelet concentrate, wound or tissue healant composition, or cell compositions according to the invention may be combined with a hydrogel like the Albugel (EP1543846) preparation of 100% Albumin or any other hydrogel resulting from the reticulation of Albumin and other chemical compound like polyethylene glycol or any other ingredient, using a paper based highly hydrophilic carrier to leave in contact with the skin until the platelet rich plasma is absorbed.

The tensile strength of the wound or tissue healant compositions of the present invention can be affected by the addition of calcium ions. Consequently, if a stronger wound or tissue healant composition is desired more calcium ions may be added at the time the serum is mixed with the platelet concentrate. Alternatively, calcium ions may be introduced directly into the platelet concentrate, and the wound or tissue healant compositions, respectively, will form.

As discussed in further detail below, the time period necessary for the formation of the wound or tissue healant compositions of the present invention is dependent on the quantity of serum added. A 1:4, 1:2 and 3:4 ratio of serum to platelet concentrate results in the formation of the wound or tissue healant compositions in approximately 90, 55 and 30 seconds, respectively. Furthermore, thrombin is preferably used within five hours of preparation, preferably within two hours and ideally immediately. As thrombin is active at room temperature still after 10 days, thrombin may be used at a later stage. Alternatively, the serum can be chilled or frozen indefinitely, preferably used before 1 month of storage.

The wound or tissue healant compositions of this invention may be used for sealing a surgical wound by applying to the wound a suitable amount platelet concentrate once it has begun to gel. Moreover, due to the fact that the wound or tissue healant compositions of the present invention may be prepared solely from blood components derived from the patient that is to receive the wound or tissue healant compositions there is a zero probability of introducing a new blood transmitted disease to the patient.

The methods of the present invention may be further modified so that the formed wound or tissue healant composition functions not only as a haemostatic agent, but also as an adjunct to wound healing and as a matrix for delivery of drugs and proteins with other biologic activities. For example, it is well known that fibrin glue has a great affinity to bind bone fragments, which is useful in bone reconstruction, as in plastic surgery or the repair of major bone breaks. Consequently, in keeping with the autologous nature of the wound or tissue healant composition of the present invention, autologous bone from a patient can be ground or made into powder or the like, and mixed into the platelet concentrate of the present invention. Serum comprising thrombin is then mixed in with the platelet concentrate and bone fragments in an amount sufficient to allow the resulting gel to be applied to the desired locale where it congeals.

In instances where the desired wound or tissue healant composition of the present invention is to further function as a delivery device of drugs and proteins with other biologic activities the method of the present invention may be modified as follows. Prior to adding the serum comprising thrombin to the platelet concentrate, a wide variety of drugs or proteins with other biologic activities may be added to the platelet concentrate. Examples of the agents to be added to the platelet concentrate prior to the addition of the serum include, but are not limited to, analgesic compounds, antibacterial compounds, including bactericidal and bacteriostatic compounds, antibiotics (e.g., adriamycin, erythromycin, gentimycin, penicillin, tobramycin), antifungal compounds, anti-inflammatories, antiparasitic compounds, antiviral compounds, enzymes, enzyme inhibitors, glycoproteins, growth factors, recombined (e.g., lymphokines, cytokines), hormones, steroids, glucocorticosteroids, immunomodulators, immunoglobulins, minerals, neuroleptics, proteins, peptides, lipoproteins, tumoricidal compounds, tumorstatic compounds, toxins and vitamins (e.g., Vitamin A, Vitamin E, Vitamin B, Vitamin C, Vitamin D, or derivatives thereof). It is also envisioned that selected fragments, portions, derivatives, or analogues of some or all of the above may be used.

A number of different medical apparatuses and testing methods exist for measuring and determining coagulation and coagulation-related activities of blood. These apparatuses and methods can be used to assist in determining the optimal formulation of activator, that is, thrombin, platelet concentrate and plasma necessary to form the wound or tissue healant compositions of the present invention. Some of the more successful techniques of evaluating blood clotting and coagulation are the plunger techniques illustrated by U.S. Pat. No. 4,599,219 to Cooper et al., U.S. Pat. No. 4,752,449 to Jackson et al., and U.S. Pat. No. 5,174,961 to Smith, all of which are incorporated herein by reference.

The plasma concentrate, PRP, compositions of the present invention can be admixed with either tricalcium phosphate (TCP), hyaluronic acid (HA), chitosan, cream, cream mask, cell extracts, fat cells, lubricin, cd-gelatin and/or botulinum toxin.

In one embodiment, a plasma concentrate or PRP composition of the present invention can be admixed with tricalcium phosphate (TCP), hyaluronic acid (HA), chitosan, cream, cream mask, cell extracts, fat cells, lubricin, cd-gelatin and/or botulinum toxin.

In one embodiment, a plasma concentrate or PRP composition, preferably of the present invention, can be admixed with tricalcium phosphate (TCP), hyaluronic acid (HA), chitosan, cream, cream mask, cell extracts, fat cells, lubricin, cd-gelatin and/or botulinum toxin.

In one embodiment, a plasma concentrate or PRP composition, preferably of the present invention, can be admixed with thrombin, preferably a thrombin serum of the present invention, and further admixed with tricalcium phosphate (TCP), hyaluronic acid (HA), chitosan, cream, cream mask, cell extracts, fat cells, lubricin, cd-gelatin and/or botulinum toxin.

In one embodiment, a plasma concentrate or PRP composition, preferably of the present invention, can be admixed with thrombin, preferably a thrombin serum of the present invention, and further admixed with a cell extract and tricalcium phosphate (TCP), hyaluronic acid (HA), chitosan, cream, cream mask, other cell extracts, fat cells, lubricin, cd-gelatin and/or botulinum toxin.

Automated apparatuses employing the plunger technique for measuring and detecting coagulation and coagulation-related activities generally comprise a plunger sensor cartridge or cartridges and a microprocessor controlled apparatus into which the cartridge is inserted. The apparatus acts upon the cartridge and the blood sample placed therein to induce and detect the coagulation-related event. The cartridge includes a plurality of test cells, each of which is defined by a tube-like member having an upper reaction chamber where a plunger assembly is located and where the analytical test is carried out, and a reagent chamber which contains a reagent or reagents. For an activated clotting time (ACT) test, for example, the reagents include an activation reagent to activate coagulation of the blood. A plug member seals the bottom of a reagent chamber. When the test commences, the contents of the reagent chamber are forced into the reaction chamber to be mixed with the sample of fluid, usually human blood or its components. An actuator, which is a part of the apparatus, lifts the plunger assembly and lowers it, thereby reciprocating the plunger assembly through the pool of fluid in the reaction chamber. The plunger assembly descends by the force of gravity, resisted by a property of the fluid in the reaction chamber, such as its viscosity. When the property of the sample changes in a predetermined manner as a result of the onset or occurrence of a coagulation-related activity, the descent rate of the plunger assembly therethrough is changed. Upon a sufficient change in the descent rate, the coagulation-related activity is detected and indicated by the apparatus.

The wound or tissue healing compositions, haemostatic agents, cell compositions, isolated cell compositions, cell preparations or cell extracts described herein may be combined with a platelet concentrate (PRP).

In another further embodiment, the invention provides a process for the preparation of a wound or tissue healing composition, a haemostatic agent, a cell composition or a cell preparation wherein the cell extract is an extract of keratinocytes.

In another further embodiment, the invention provides a process for the preparation of a wound or tissue healing composition, a haemostatic agent, a cell composition or a cell preparation wherein the cell extract is an autologous extract of keratinocytes.

In another further embodiment, the invention provides a process for the preparation of a wound or tissue healing composition, a haemostatic agent, a cell composition or a cell preparation wherein the cell extract is an extract of skeletal muscle cells such as muscle progenitor cells or satellite stem cells.

In another further embodiment, the invention provides a process for the preparation of a wound or tissue healing composition, a haemostatic agent, a cell composition or a cell preparation wherein the cell extract is an extract of fibroblasts.

In another further embodiment, the invention provides a process for the preparation of a wound or tissue healing composition, a haemostatic agent, a cell composition or a cell preparation wherein the cell extract is an extract of adipocytes, preadipocytes, pre-endothelial cells, or mesenchymal stem cells.

In another further embodiment, the invention provides a process for the preparation of a wound or tissue healing composition, a haemostatic agent, a cell composition or a cell preparation wherein the cell extract is an extract of chondrocytes.

In another further embodiment, the invention provides a process for the preparation of a wound or tissue healing composition, a haemostatic agent, a cell composition or a cell preparation wherein the cell extract is an extract of stem cells such as umbilical cord stem cells.

In another further embodiment, the invention provides a process for the preparation of a wound or tissue healing composition, a haemostatic agent, a cell composition or a cell preparation wherein the cell extract is an extract of tendon cells.

In another further embodiment, the invention provides a process for the preparation of a wound or tissue healing composition, a haemostatic agent, a cell composition or a cell preparation wherein the cell extract is an extract of periosteal filter or gingival cells.

In another further embodiment, the invention provides a process for the preparation of a wound or tissue healing composition, a haemostatic agent, a cell composition or a cell preparation wherein the cell extract is an extract of corneal cells.

In another further embodiment, the invention provides a process for the preparation of a wound or tissue healing composition, a haemostatic agent, a cell composition or a cell preparation wherein the cell extract is an extract of bone marrow cells.

In another further embodiment, the invention provides a process for the preparation of a wound or tissue healing composition, a haemostatic agent, a cell composition or a cell preparation wherein the cell extract is an extract of osteoblast cells.

In another further embodiment, the invention provides a process for the preparation of a wound or tissue healing composition, a haemostatic agent, a cell composition or a cell preparation wherein the cell extract is an extract of Schwann cells.

In another further embodiment, the invention provides a process for the preparation of a wound or tissue healing composition, a haemostatic agent, a cell composition or a cell preparation wherein the cell extract is an extract of pancreas islet cells.

In another further embodiment, the isolated platelet concentrate composition, the wound or tissue healant composition, the thrombin enriched serum, the cell extract, the wound or tissue healing composition, the haemostatic agent, the cell composition and/or the cell preparation of the invention is/are autologous.

In a further aspect, the present invention provides a kit adapted for tissue regeneration according to the invention wherein the kit further comprises separate vials containing calcium gluconate, albumin, chitosan, cream, lubricin, TCP, ETOH and/or CaCl2, syringe holders, clumper and/or a tip applicator with a dual exit. The use of autologous thrombin serum according to the invention has the advantage that additives like ETOH and CaCl2 are not required for the preparation of a wound healant or PRP preparation.

In another embodiment, the invention provides a process for the preparation of a cell composition according to the invention wherein the cell extract provided under step d) or e) is obtained by a process comprising the steps of:

(A) Providing the said cells in a platelet concentrate according to the invention, (B) Optionally culturing the cells, and (C) Re-suspending the cultured cells obtained under step (B) into a platelet concentrate according to the invention.

In a further embodiment, the invention provides a process for the preparation of a cell composition according to the invention wherein the cell expansion under step (A) is performed in a platelet concentrate according to the invention such as the final concentration in platelets is comprised between about 5% and about 40% of the volume of the culture medium.

In another further embodiment, the invention provides a process for the preparation of a cell composition according to the invention wherein the cell culture step (B) comprises at least one step of plating the cells, for example on a cell culture surface such as a Petri dish or a culture flask.

In another further embodiment, the invention provides a process for the preparation of a cell composition according to the invention comprising at least one further step of harvesting the cells after the cell culture step (B).

In another further embodiment, the invention provides a process for the preparation of a cell composition according to the invention wherein the cell culture step (B) is performed at 37° C.

In another further embodiment, the invention provides a process for the preparation of a cell composition according to the invention wherein the cell culture step (B) is performed under a gas flow comprising oxygen or air and carbon dioxide. Typically the gas flow comprises 95% of oxygen or air and 5% carbon dioxide.

In another further embodiment, the invention provides a process for the preparation of a cell composition according to the invention wherein the cell culture step (B) lasts for about 3 up to about 4 weeks.

In another further embodiment, the invention provides a process for the preparation of a cell composition according to the invention wherein during the cell culture step (B), the cell culture medium is regularly changed during incubation, typically every about 3 days.

In another further embodiment, the invention provides a process for the preparation of a cell composition according to the invention wherein the cell culture step (B) comprises at least one exposure step of the cells to visible light, typically at about 633 nm, during about 10 minutes. In another aspect, the exposure step to visible light is repeated once a week during cell incubation.

In another further embodiment, the invention provides a process for the preparation of a cell composition according to the invention wherein the cell composition is a keratinocyte or fibroblast cell composition and the cell culture step (B) comprises at least one exposure step of the cells to visible light, typically at about 633 nm, during about 10 minutes. In another aspect, the exposure step to visible light is repeated once a week during cell incubation.

In another further embodiment, the invention provides a process for the preparation of a cell composition according to the invention wherein the cell culture step (B) comprises at least one step of addition of diluted platelet concentrate according to the invention such as the final concentration in platelets comprised between about 5% and about 40% of the volume of the culture medium.

In another further embodiment, the invention provides a process for the preparation of a cell composition according to the invention wherein the cell composition is a keratinocyte or fibroblast cell composition and the cell culture step (B) comprises at least one step of addition of diluted platelet concentrate according to the invention such as the final concentration in platelets comprised between bout 5% and about 40% of the volume of the culture medium.

In another embodiment, the present invention provides an isolated cell composition obtainable from a process according to the invention.

In another embodiment, the present invention provides an isolated cell composition, wherein the isolated cell composition is a fat cell composition such as an adipocyte cell composition.

In another embodiment, the present invention provides an isolated cell composition, wherein the isolated cell composition is a muscle cell composition such as a myoblast cell or a satellite stem cell composition.

In another embodiment, the present invention provides an isolated cell composition, wherein the isolated cell composition is a corneal cell composition.

In another embodiment, the present invention provides an isolated cell composition, wherein the isolated cell composition is a cartilage cell composition, such as a chondrocyte cell composition.

In another embodiment, the present invention provides an isolated cell composition, wherein the isolated cell composition is a skin cell composition, such as a fibroblast cell or keratinocyte cell composition.

In another embodiment, the present invention provides an isolated cell composition, wherein the isolated cell composition is a periosteal filter or gengival cell composition.

In another embodiment, the present invention provides an isolated cell composition, wherein the isolated cell composition is a tendon cell composition.

In another embodiment, the present invention provides an isolated cell composition, wherein the isolated cell composition is a stem cell composition, such as an umbilical cord stem cell composition.

In another embodiment, the present invention provides an isolated cell composition, wherein the isolated cell composition is a bone marrow cell composition.

In another embodiment, the present invention provides an isolated cell composition, wherein the isolated cell composition is a Schwann cell composition.

In another embodiment, the present invention provides an isolated cell composition, wherein the isolated cell composition is a pancreas islet cell composition.

In another embodiment, the present invention provides an isolated cell composition, wherein the isolated cell composition is an osteoblast cell composition.

In another embodiment, the present invention provides an isolated cell composition, wherein cells are at a concentration of about $3 \times 10^5$ to about $10^6$ cells/ml of plasma or enriched plasma.

In another embodiment, the present invention provides compositions, methods and uses for promoting wound or tissue sealing and/or tissue and/or bone regeneration in a wound of a human or a lower animal as described herein.

In another further embodiment, the present invention provides compositions, methods and uses for promoting wound or tissue sealing and/or tissue and/or bone regeneration in a wound of a mammal, preferably human. In another embodiment, the present invention provides compositions, methods and uses for inducing periodontal regeneration in a wound or a periodontal defect of a mammal with periodontal disease or other condition as described herein.

In another further embodiment, the present invention provides a method for inducing periodontal regeneration in a wound or a periodontal defect or cavity of a mammal with periodontal disease or other condition wherein the mammal is human.

In another further embodiment, the present invention provides a method for inducing periodontal regeneration in a wound or a periodontal defect or cavity according to the invention wherein the said therapeutically effective amount of the said wound or tissue healant composition is applied in a form of semi-solid gel or a growth matrix to the said wound or said periodontal defect or cavity such as described for example in Garg et al., 2000, Dental Implantology Update, 11(6), 41-44.

In another embodiment, the present invention provides a method for promoting skin tissue regeneration in a scar or wrinkle as described herein.

In another embodiment, the present invention provides a method for inducing myocardial regeneration according to the invention, wherein the said therapeutically effective amount of the said muscle cell composition according to the invention is injected in combination with a platelet concentrate (PRP) into the myocardium, typically into the left ventricule myocardium. Injection can be made as direct injection or multiple catheter injection. Myoblasts or satellite cells can be engineered ex vivo as described in the present description onto a de-epithelised and UV irradiated human biological amnion and biocomposite construct, as a monolayer in the present description. The amnion is then sutured to the ischaemic epicardium in order to repopulate the underlying tissue with stem cells, in order to improve the contractile power of the ventricular wall and myocytes.

In another embodiment, the present invention provides a method for inducing myocardial regeneration according to the invention, wherein the said therapeutically effective amount of the said muscle cell composition according to the invention is injected in combination with a platelet concentrate (PRP) into the myocardium, together with a therapeutically effective amount of fibroblast cell composition according to the invention in combination with a platelet concentrate (PRP). In another embodiment, the present invention provides a method for inducing myocardial regeneration according to the invention, wherein the said therapeutically effective amount of the said muscle cell composition according to the invention is applied in combination with a platelet concentrate (PRP) on the ventricular surface in the form of an amnion patch preferably incubated into a myoblast and satellite stem cell composition according to the invention.

In another embodiment, the present invention provides a method for inducing corneal regeneration according to the invention, wherein the said therapeutically effective amount of the said corneal cell composition according to the invention in combination with a platelet concentrate (PRP) is applied to the corneal tissue in the form of an amnion patch preferably spread on a dissolvable contact lens.

Said method of treating a wound, a tissue or a disease may include the use of any of the compositions described herein; it may also include the use of any composition made by any of the methods described herein.

The methods, the devices and the kit according to the invention present the advantages to provide a time-effective and relatively low-cost way of obtaining platelet concentrates in a single operation that is easy to implement and adapted to a point-of-care application. The methods of the invention present the advantage to not only lead to enriched preparations wherein the platelets are concentrated in such a high yield but also wherein the content in erythrocytes is low. The compositions of the invention present the advantage of having a high content in platelets, a low content in erythrocytes with completely maintained properties for its subsequent therapeutic use in-vivo. More specifically, the ability of the platelets to release the principal growth factors involved in tissue regeneration (PDGF, TGF-beta, IGF, VEGF and EGF) at levels for several days (or the 30 days life span of thrombocytes) is maintained. In addition, to the extent the compositions of the invention are made from autologous blood, the invention described herein reduces the disease transmission and immunoreaction risks associated with the use of the treatment materials made from biological materials obtained from one or more third parties. The invention therefore provides an improved biological wound healing and tissue regenerating material, preferably autologous, promoting tissue such as skin, cartilage and bone regeneration, especially cicatrisation and/or rejuvenation. The benefits of the invention comprise a simple and rapid method of preparation of improved wound healing and tissue regenerating materials adapted to point-of-care services and which proved to decrease the healing time, associated pain and medical costs. Further, the wound healing and tissue regenerating material decreases the graft rejection risks and improves graft success rates. Further, the improved wound healing and tissue regenerating materials lead to scars having a much better aesthetic final aspect and to the durable filling of scars and wrinkles.

Typically, cell extracts are obtained from a tissue biopsy wherein the biopsy is preferably performed the same day the mixture with the platelet concentrate is done. The size of the biopsies is adapted to the aimed therapeutic purpose and the types of cells used in the preparation of the cell composition according to the invention. Examples of biopsies are given in the Examples below for different types of tissues. In another aspect, the invention provides a tube comprising at least one filter separating the tube in two parts.

In another aspect, the invention provides a tube separated in two parts by at least and preferably one filter.

In one embodiment the tube is used for collecting and/or separating a fluid sample.

Preferably, the two parts differ in size and/or diameter.

In another aspect, the invention provides a tube for collecting and separating a fluid sample comprising:
 i) two distinct parts differing in size and diameter,
 ii) at least one filter separating the two parts, and
 iii) optionally an anticoagulant.

In a preferred embodiment of the invention, the tube consists of the features as illustrated in FIGS. 1 to 14.

In a preferred embodiment, the tube is made of Cyclic Olefin Polymer (COP) or Cyclic Olefin Copolymer (COC).

In one embodiment, the tube contains an anticoagulant, preferably buffered sodium citrate solution or an anhydrous sodium citrate.

In a preferred embodiment, the tube contains a buffered sodium citrate solution at 0.10 M or an anhydrous sodium citrate at 3.5 mg/mL.

In a preferred embodiment, the filter is fixed to the tube. Preferably, the filter is prolonged vertically in order to have an extended surface in contact with the tube (extended on the vertical axis of the tube). This has the advantage of increasing the stability of the filter, further preventing any movement of the filter. In a preferred embodiment, the tube comprises a filter made of two layers. Preferably, the 2 layers are superposed (one above the other; FIG. 4, FIGS. 10 to 14). Preferably, the outer layer is prolonged vertically in order to have an extended surface in contact with the tube (extended on the vertical axis of the tube FIGS. 2, 3, and 5A). Preferably, the inner layer is also prolonged in order to align with the outer layer. In one embodiment, the inner layer is not prolonged (only on the horizontal axis). In one embodiment, 2, 3, 4, 5 or more filters are comprised in the tube.

In a preferred embodiment, the first part of the tube located in the above or top portion of the tube is of greater volume than the second part located in the below or bottom portion of the tube. In a further preferred embodiment, the first part of the tube comprising the filter has a volume of about 9.5 cm3 and the second part of the tube has a volume of about 3.5 cm3 (FIG. 5A).

In a preferred embodiment, the volume of the first part of the tube located in the above portion of the tube comprising the filter represents about 70% of the total volume of the tube. In one embodiment, the volume of the first part of the tube located in the above portion of the tube comprising the filter represents about 51%, 55%, 60%, 65%, 68%, 70%, 73%, 75%, 80%, 90%, 95% or more of the total volume of the tube. In a further preferred embodiment, the volume of the second part of the tube located in the below portion of the tube represents about 30% of the total volume of the tube. In one embodiment, the volume of the second part of the tube located in the below portion of the tube represents about 49%, 45%, 40%, 35%, 32%, 30%, 27%, 25%, 20%, 15%, 10% or 5% A or less of the total volume of the tube.

In one preferred embodiment, the tube has a total volume of about 13 cm3 (FIG. 5A).

In a preferred embodiment, the second part of the tube located in the below portion of the tube has a smaller diameter than the first part of the tube located in the above portion of the tube. This has the advantage that the filter will stay in its position under centrifugation or any other mechanical stress.

Figure 3:
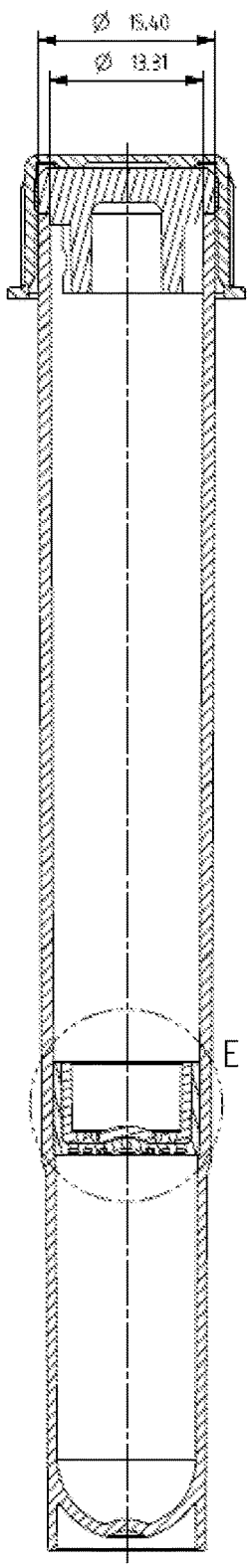

In a preferred embodiment, the external diameter of the first part of the tube located in the above portion of the tube is of about 15.5 mm or about 15.4 mm (FIG. 3). In a preferred embodiment, the internal diameter of the first part of the tube located in the above portion of the tube is of about 13.32 mm or 13.31 mm (FIG. 3).

In a preferred embodiment, the external diameter of the second part of the tube located in the below portion of the tube is of about 13.7 mm (FIG. 5A). In a preferred embodiment, the internal diameter of the second part of the tube located in the below portion of the tube is of about 11.6 mm.

In a preferred embodiment, a filter made of two layers separates the two parts of the tube. Preferably, the 2 layers are superposed (one above the other; FIG. 4, FIGS. 10 to 14).

Figure 9:
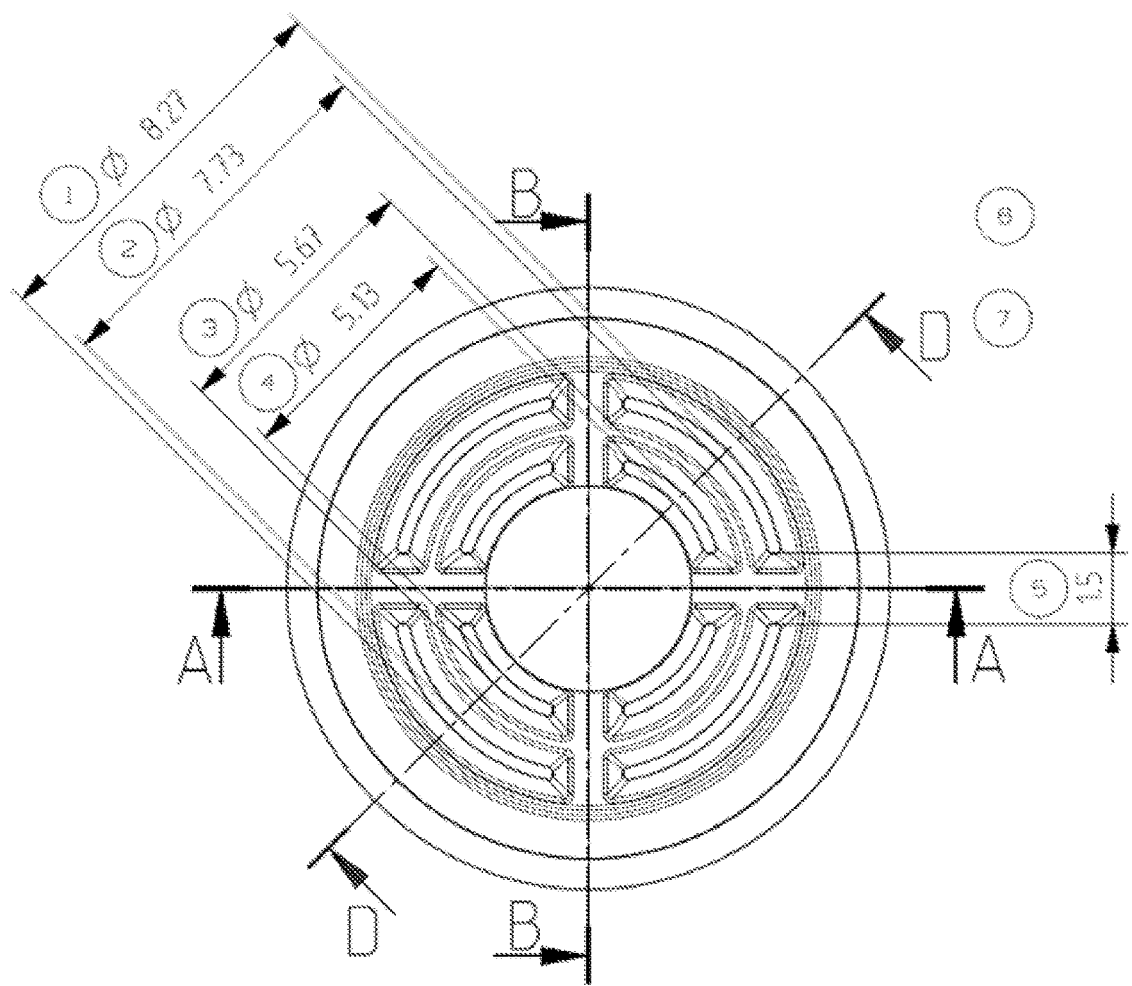
FIG. 9 represents an upper view of the filter of a tube according to the invention.
Figure 10:
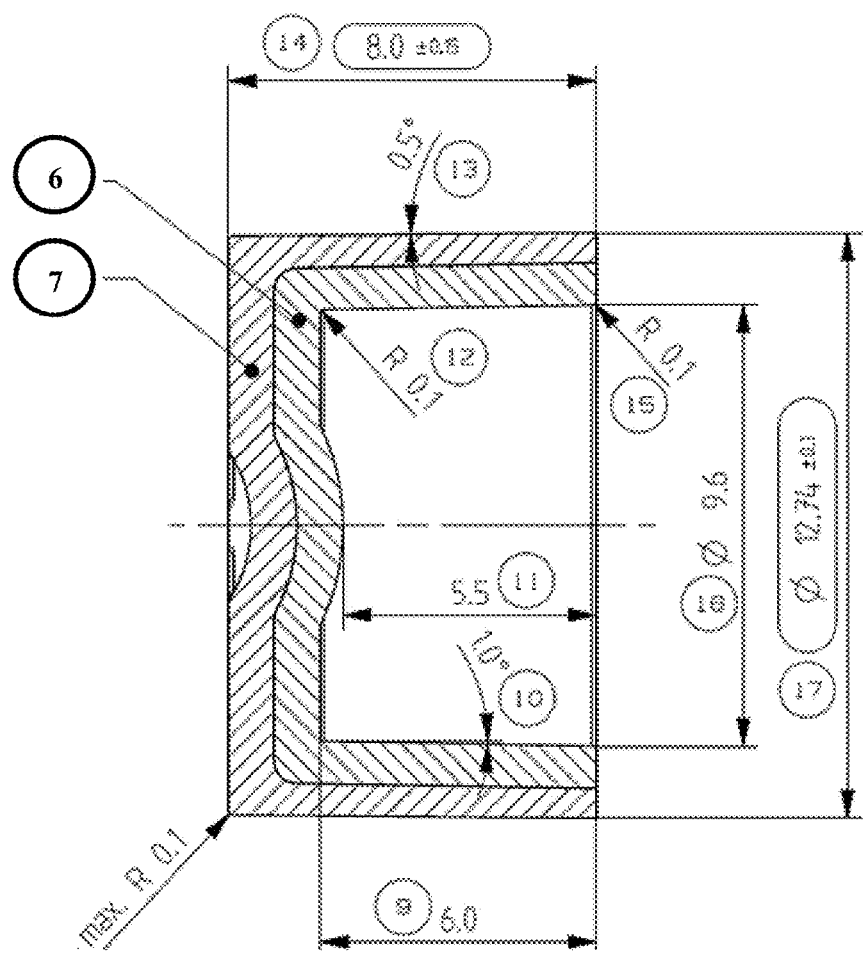
FIGS. 10 and 11 represent detailed views of the filter of a tube according to the invention.
Figure 11:
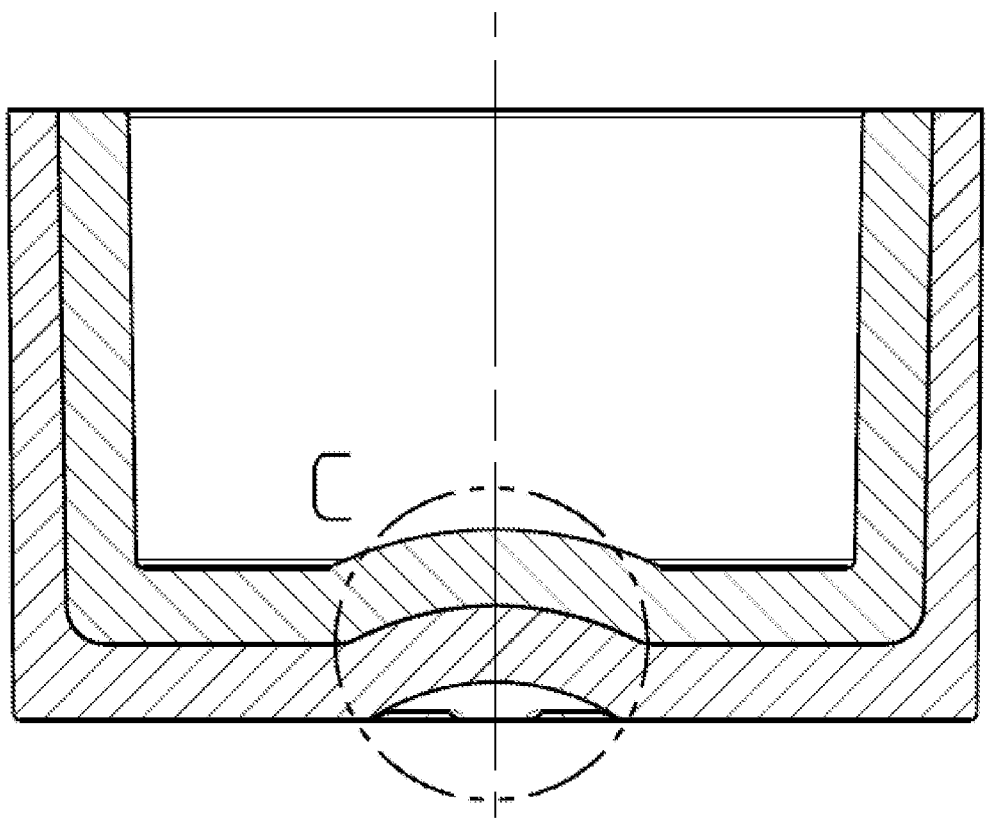
Figure 12:
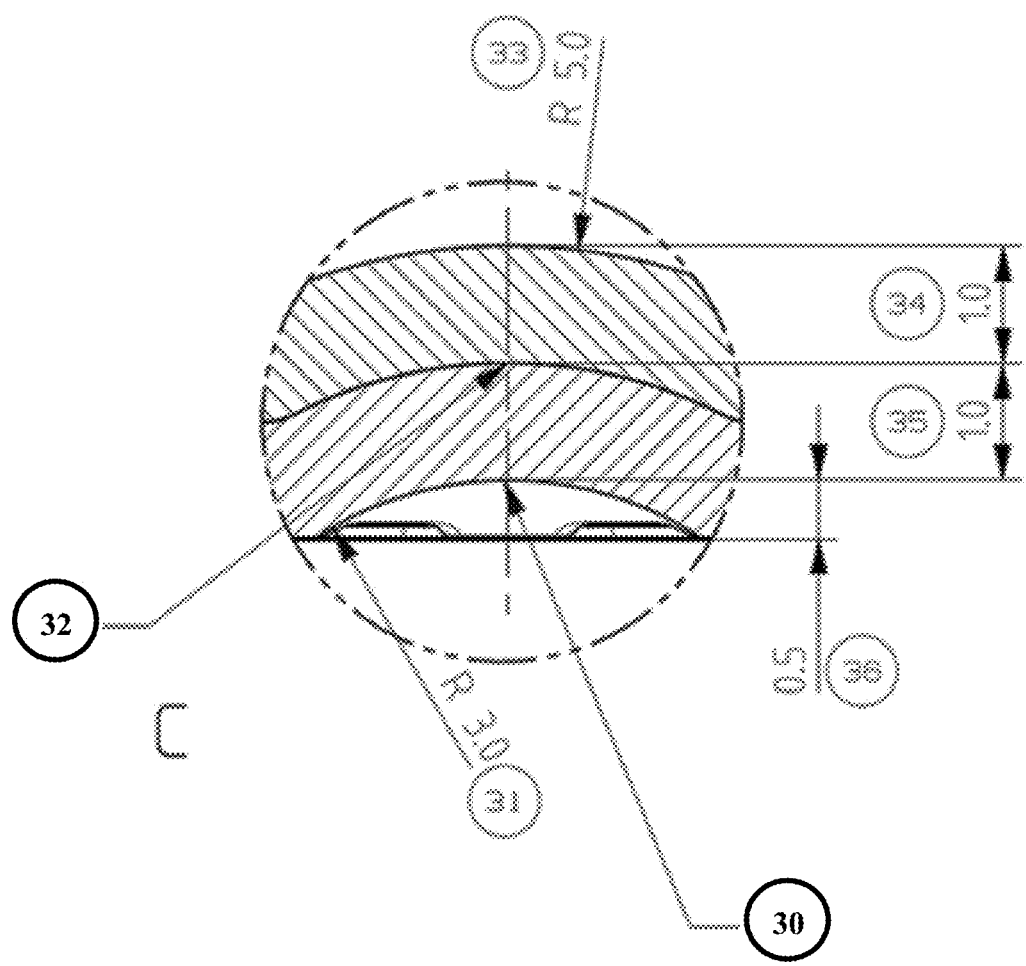
FIG. 12 represents a detailed view of the centric part of the filter of a tube according to the invention.
Figure 13:
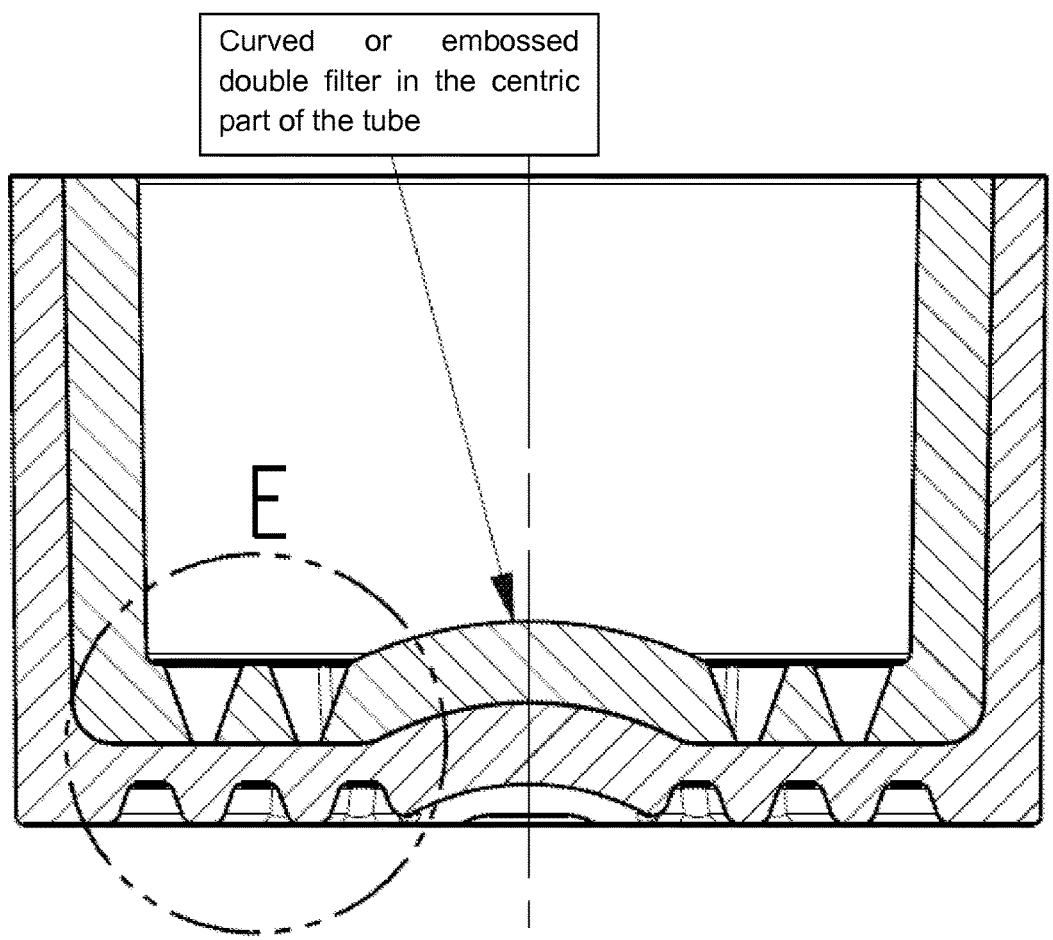
FIG. 13 is a detailed representation of the interior of the filter of a tube according to the invention. The filter comprises an internal layer with funnels and an external layer with trapezoid-like structures. Each funnel and trapezoid is integrated into the filter in an alternate manner (a first trapezoid is followed by a first funnel, followed by a second trapezoid, followed by a second funnel and ending by a third trapezoid).

A preferred filter is shown in FIG. 4 and FIGS. 7 to 14. Preferably, the filter comprises an internal and external layer (FIGS. 10, 11 and 13).

In a preferred embodiment, the filter is fixed to the tube. In another embodiment, the filter is not fixed to the tube.

Figure 4:
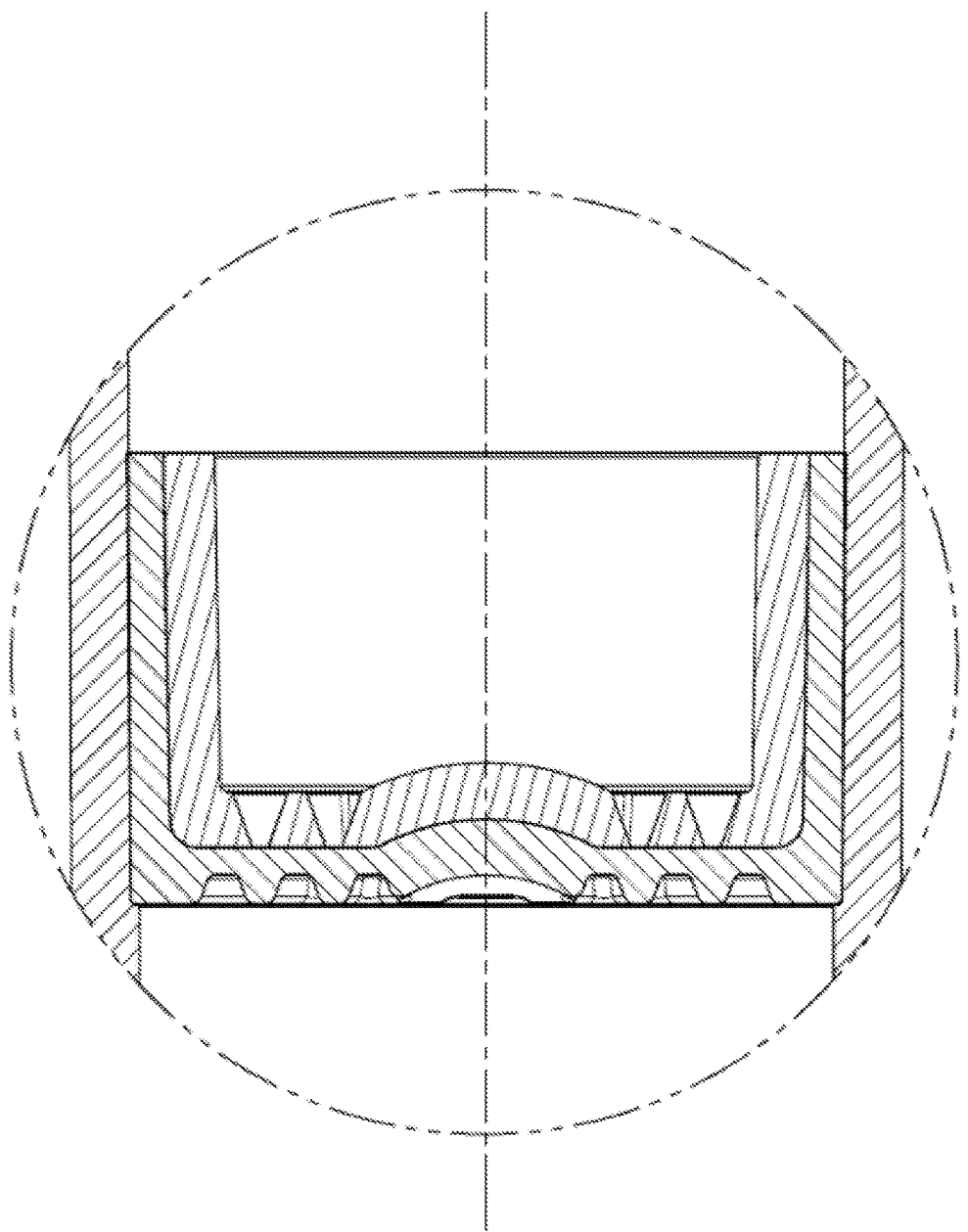
FIG. 4 is a schematic representation of the interior of the filter of a tube according to the invention. The filter comprises an internal layer with funnels and an external layer with trapezoid-like structures.
Figure 6:
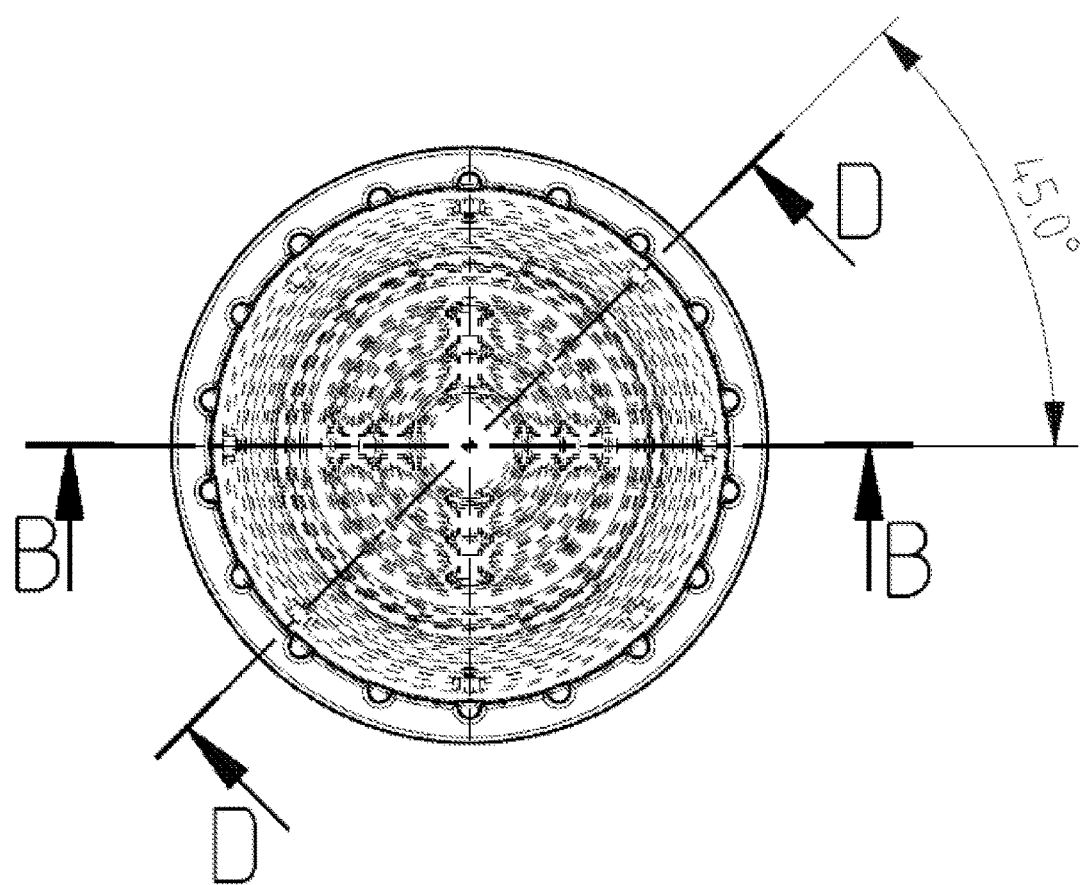
FIG. 6 is a schematic representation of the cap.
Figure 7A:
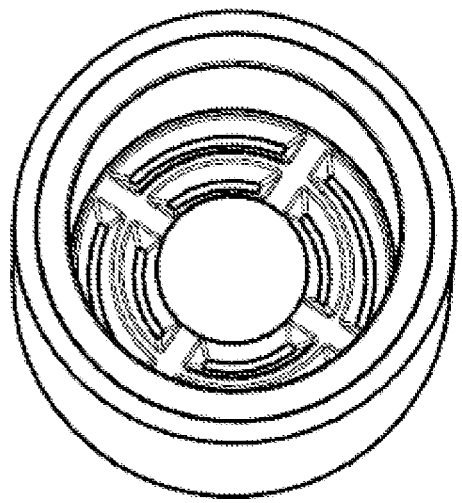
FIGS. 7A and 7B represent two distinct views of the filter of a tube according to the invention.
Figure 7B:
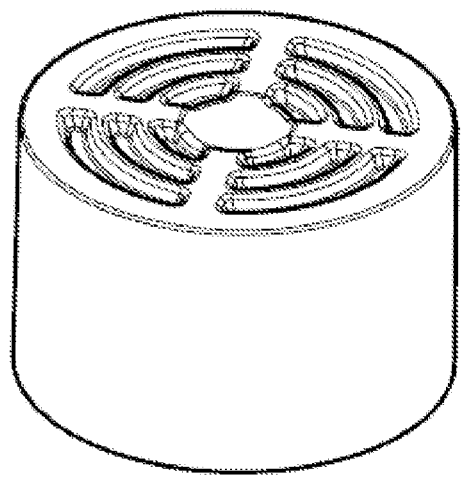
Figure 8:
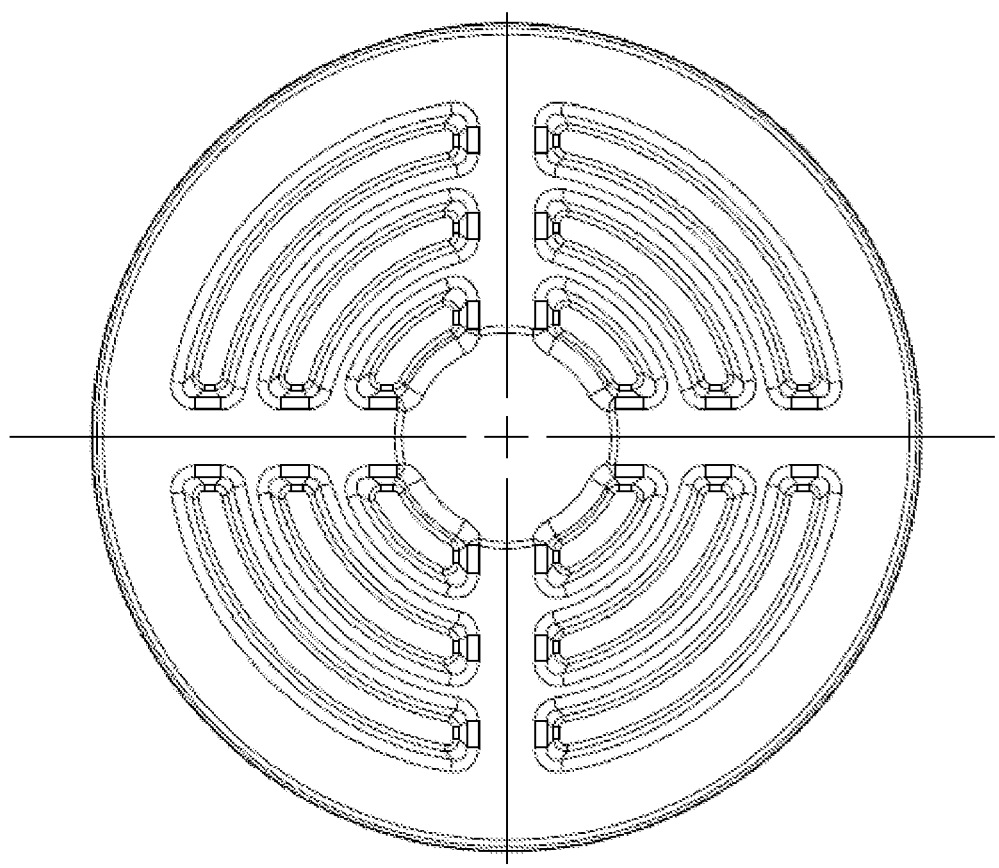
FIG. 8 represents an underneath view of the filter of a tube according to the invention.

In one embodiment, the filter comprises symmetrical series of ranges with openings disposed as shown in FIGS. 7A, 7B, 8 and 9. Preferably, the filter consists of 4 symmetrical series of ranges with 2 ranges per series, each range consisting of an opening. For the first range of openings located towards the center of the tube, the distance between the internal part of one opening and the internal part of another opening is about 5.13 mm (FIG. 4, item 4). For the first range of openings located towards the center of the tube, the distance between the external part of one opening and the external part of another opening is about 5.67 mm (FIG. 4, point 3). For the second range of openings located towards the border of the tube, the distance between the internal part of one opening and the internal part of another opening is about 7.73 mm (FIG. 4, item 2). For the second range of openings located towards the border of the tube, the distance between the external part of one opening and the external part of another opening is about 8.27 mm (FIG. 4, item 1). In one embodiment, the distance of each opening is about 0.53 or 0.54 mm (FIG. 9 and FIG. 14, item 21).

Figure 14:
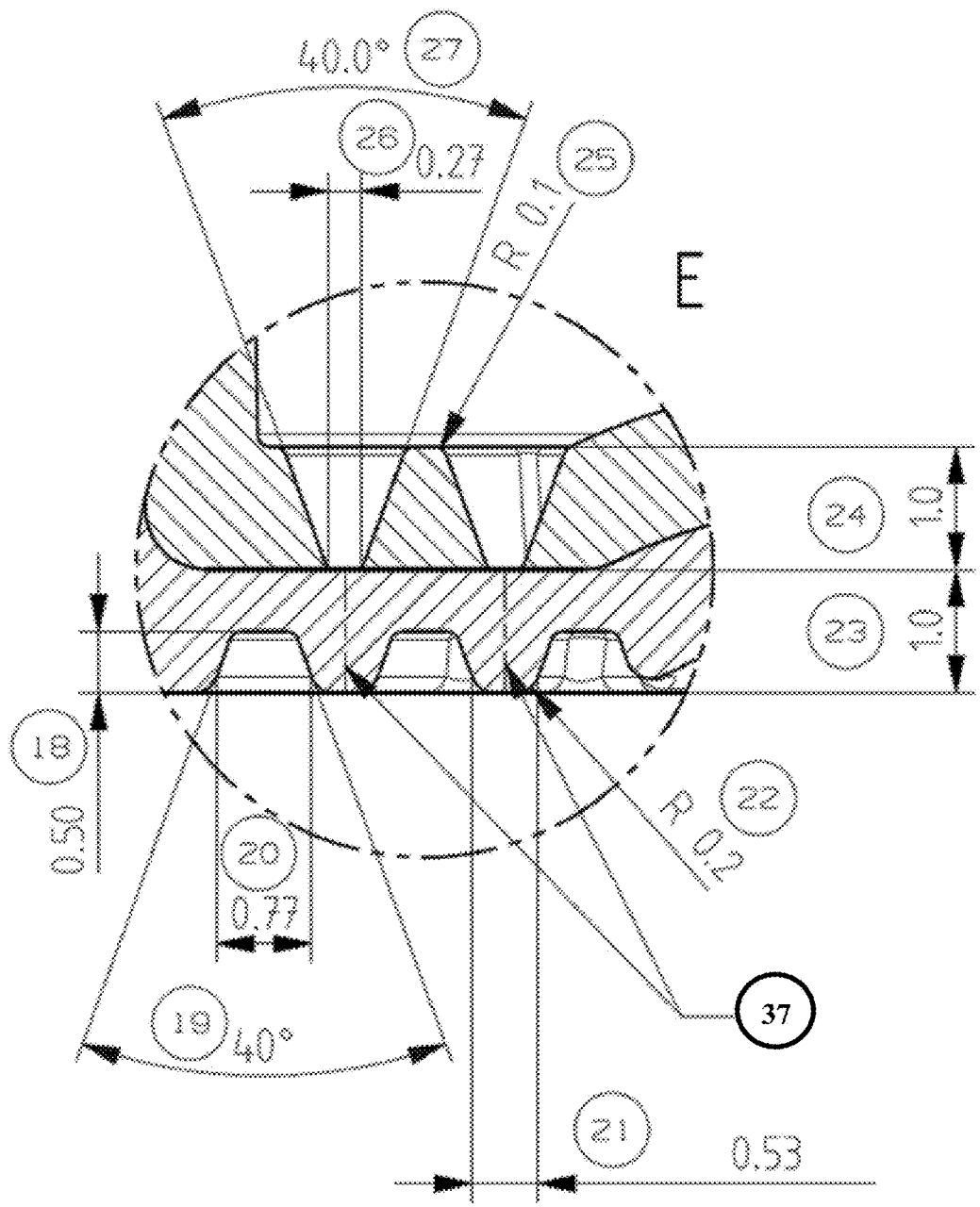
FIG. 14 is a detailed view of the filter comprising funnels and trapezoids of a tube according to the invention.

Preferably, the upper or internal layer consists of 4 symmetrical series of ranges with 2 ranges per series (FIGS. 9, 13 and 14), each range consisting of an appropriate number of funnels disposed regularly (FIGS. 13 and 14). Preferably, the gap or opening located at the bottom of each funnel is of a length of about 0.27 mm (FIG. 14, item 26). Preferably, the distance from one extremity to the other of the funnel is about 1 mm, corresponding to the thickness of the upper layer (FIG. 14, item 24). Preferably, the thickness of the upper layer is about 1 mm (FIG. 12, item 34 and FIG. 14, item 24). The number of funnels will depend on the size of the layer. Preferably, the funnel comprises a closed aperture at its base (item 26 of FIG. 14).

Preferably, the lower or external layer consists of 4 symmetrical series of ranges with 3 ranges per series (FIGS. 8, 13 and 14), each range consisting of an appropriate number of trapezoids disposed regularly (FIGS. 13 and 14). The number of trapezoids will depend on the size of the layer. Preferably, each trapezoid is separated by a distance of about 0.53 mm (FIG. 14). The base of each trapezoid is of a length of about 0.77 mm (FIG. 14). Preferably, the height of each trapezoid is about 0.5 mm (FIG. 14). Preferably, the thickness of the lower layer is about 1 mm (FIGS. 12 and 14).

Preferably, the ranges of the upper and lower layers always alternate. Preferably, a first range of trapezoids of the lower layer will be followed by a first range of funnels of the upper layer which will be followed by a second range of trapezoids of the lower layer followed by a second range of funnels of the upper layer which will be finally followed by a third range of trapezoids of the lower layer (FIGS. 4, 13 and 14).

Preferably, each funnel of the upper layer is located in such a manner that the prolongation of the center of the funnel will fall approximately between two trapezoids of the lower layer (FIGS. 4, 13 and 14). More preferably, each funnel of the upper layer is located in such a manner that the prolongation of the center of the funnel will fall exactly between two trapezoids of the lower layer (FIGS. 4, 13 and 14). Preferably, a trapezoid alternates continuously with a funnel.

When the tube of the present invention is centrifuged, the closed aperture at the base of the funnel (item 26 of FIG. 14) opens due to the centrifugal force allowing the passage of the Red Blood Cells that are directed between two trapezoids and finally to the lower section of the tube. Once centrifugation stops, the aperture of the funnels will close hindering the reflux of the Red Blood Cells to the upper portion of the tube. The trapezoids of the lower layer located beneath each funnel will facilitate the passage of the Red Blood Cells to the lower portion of the tube and help in preventing the reflux of the Red Blood Cells.

Preferably, the volume of the upper layer is about 0.26 cm3. Preferably, the volume of the lower layer is about 0.29 cm3.

Preferably, the upper layer is made of polypropylene (PP) (FIG. 10, item 6). Preferably, the lower layer is made of a thermoplastic elastomer (TPE) (FIG. 10, item 7). Other components may be used as described in the present invention or known by the skilled artisan.

Preferably, the center of the filter is curved (FIGS. 4, 10 to 13). This has the advantage of canalizing the whole blood towards the funnels. Preferably, the filter is curved in such a manner as to have a length of about 0.5 mm from the center of the tube to the base of the lower layer (FIG. 12, item 36). Items 30 and 32 in FIG. 12 are injection points.

Preferably, the height of the lower layer is about 8 mm (FIG. 2 and FIG. 10, item 14). Preferably, the outer diameter of the lower layer is about 12.74 mm (FIG. 10, item 17). Preferably, the inner diameter of the upper layer is about 9.6 mm (FIG. 10, item 16). Preferably, the height of the layer from the upper non-curved surface of the upper layer is about 6 mm (FIG. 10, item 9). Preferably, the height of the layer from the center of the curved upper surface of the upper layer is about 5.5 mm (FIG. 10, item 11).

In one embodiment of the invention, the tube comprises only a filter with funnels.

In another embodiment of the invention, the number of funnels and/or trapezoids can vary. In another embodiment of the invention, the number of ranges of funnels and/or trapezoids can vary. In another embodiment of the invention, the number of symmetrical series of ranges of funnels and/or trapezoids can vary. In another embodiment of the invention, the tube consists of 2 symmetrical series of ranges of funnels and/or trapezoids.

The present invention also encompasses a tube wherein the lengths of all components differ from those indicated herein. The present invention also encompasses a tube wherein the lengths of all components differ from those indicated herein with a length of about 0.1 mm, 0.2 mm, 0.3 mm, 0.5 mm, 1 mm, 1.5 mm, 2 mm, 5 mm, 8 mm, 10 mm, 15 mm, 20 mm, 50 mm, 75 mm, 1 cm, 2 cm, 5 cm, 10 cm or more.

In one embodiment, the filter is shaped or modeled with a laser (FIG. 14, item 37).

The tubes of the present invention have the advantage of separating with high efficacy Red Blood Cells from the plasma. Using the tubes of the present invention, the percentage of RBCs in the plasma is reduced by more than 99%, 98%, 95%, 93%, 90%, 85%, 80%, 75%, 70%, 65% or 60% compared with the percentage of RBCs present in whole blood.

COCs or COPs, apart from cost savings and being a stiff and strong medical material, have the advantage that its transparency is similar to glass in its natural form. Typical COC material will have a higher modulus than HDPE (High-density polyethylene (HDPE) or polyethylene high-density (PEND) is a polyethylene thermoplastic made from petroleum) and PP (Polypropylene or polypropene (PP) is a thermoplastic polymer). COC also has a high moisture barrier for a clear polymer along with a low absorption rate. In medical applications, COC is noted to be a high purity product with low extractables. COC is also a halogen-free product.

COC material has excellent optical clarity and a high barrier to water vapor. It molds fine features with great fidelity, withstands all common sterilization methods, and resists hydrolysis and a wide range of chemicals.

COC material also has good heat resistance, mechanical properties, hardness, dimensional stability, and electrical insulating properties. Because it is very low in extractables and has excellent in-vivo and in-vitro biocompatibility, it meets USP Class VI and ISO 10993 requirements and has received FDA Drug and Device Master File numbers.

In addition, COC, with its transparency, stiffness, low weight, heat and chemical resistance, biocompatibility, dimensional stability to moisture barrier (low moisture permeability), moldability, and lack of halogens, offers many benefits in use. It reduces breakage in devices and packaging compared to glass, extends medication shelf life, allows diagnostic readings at UV wavelengths, and enables smaller and faster diagnostic equipment. In addition, COC grades can also undergo sterilization by gamma radiation, steam and ethylene oxide and can thus be sterilized by all common methods.

Figure 15:
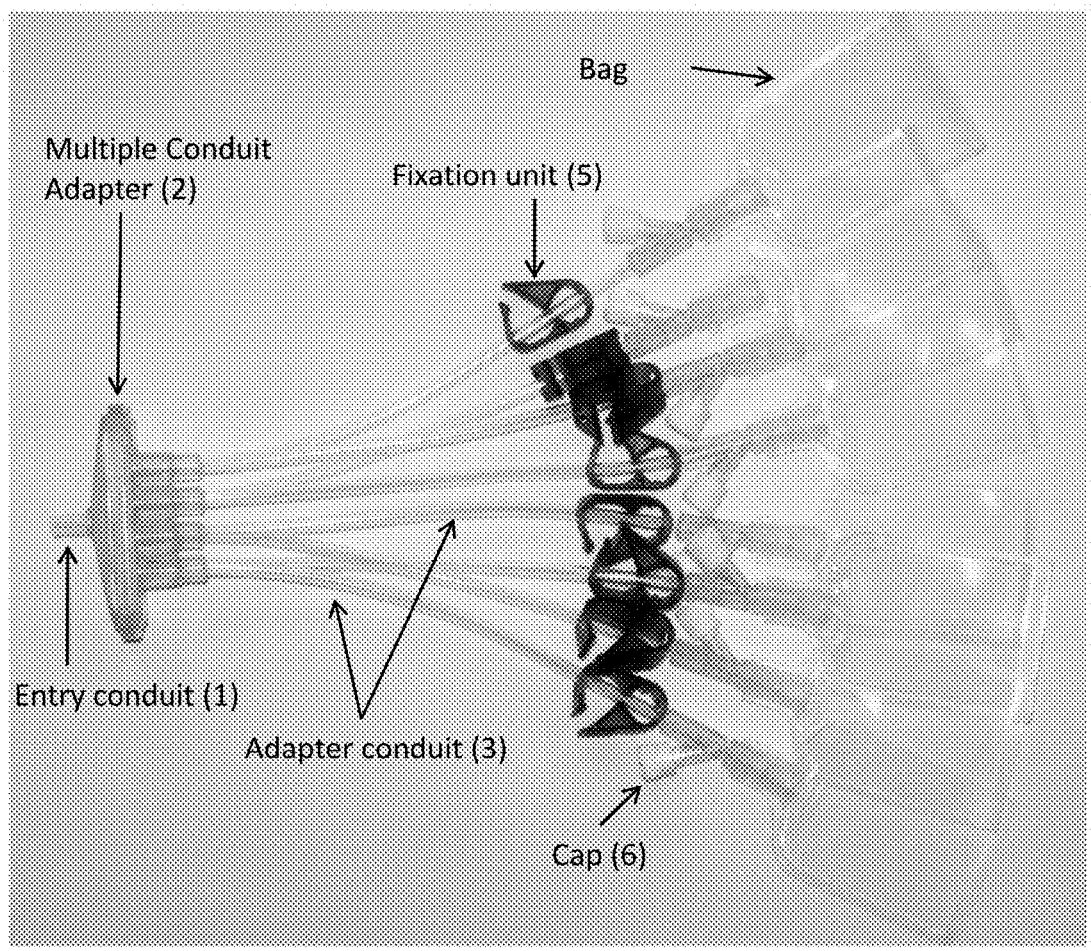
FIG. 15 is a view of the blood bag system or blood collection tubes device of the invention.

In another aspect, the invention provides a blood bag system or blood collection tubes device according to FIG. 15.

Blood collected and/or stored in a blood bag system or blood collection tubes device according to the invention may be used in any of the processes, compositions, products, and uses according to the present invention.

The blood collection tubes or bags may be evacuated and/or sealed. The blood collection tubes or bags may be filled with thixotropic gel and/or anticoagulant.

The blood bag system or blood collection tubes device of the invention consists in a multi-channel blood collector allowing delivery of plasma and cell components to multiple bags or tubes.

In another aspect, the invention provides a blood bag system or blood collection tubes device comprising a single entry conduit connected to a multiple conduit adapter with adapter conduits connected to at least two bags or tubes, wherein each adapter conduit of the multiple conduit adapter is connected to one single bag or tube.

In another aspect, the invention provides a blood bag system or blood collection tubes device comprising:
 a) a single entry conduit,
 b) a multiple conduit adapter with adapter conduits, and
 c) at least two bags or tubes,
wherein the single entry conduit is connected to the multiple conduit adapter and wherein each adapter conduit of the multiple conduit adapter is connected to one single bag or tube.

In one embodiment, the invention provides a blood bag system or blood collection tubes device according to the invention for pooling blood components.

Preferably, the blood bag system or blood collection tubes device comprises an entry conduit (1), a multiple conduit adapter (2), adapter conduits (3) and at least two bags or tubes (4) as illustrated in FIG. 15.

In one embodiment, the blood bag system or blood collection tubes device further comprises one or more fixation units (5) (FIG. 15). Preferably, one fixation unit is provided for each adapter conduit. In one embodiment, two or more fixation units are provided for each adapter conduit.

Preferably, each bag of the blood bag system or blood collection tubes device further comprises a cap. FIG. 15 illustrates a blood bag system or blood collection tubes device wherein each bag (4) comprises a cap (6). Preferably, the cap can be unlocked or unscrewed in order to connect a sterile syringe. The cap has the advantage of allowing easy aspiration of the content of the bag in sterile conditions. In one embodiment, a Luer-Lock syringe may be used. Alternatively, a needle may be used instead of a cap.

Preferably, the entry conduit and adapter conduits are flexible. Preferably, the entry conduit and adapter conduits are tubular.

In one embodiment, the blood bag system or blood collection tubes device comprises 2, 3, 4, 5, 6, 7, 8, 9, 10, 12, 14, 16, 18, 20 or more bags or tubes. Preferably, the blood bag system or blood collection tubes device comprises 8 bags or tubes.

Preferably, the invention provides disposable bags or tubes for single use.

In one embodiment, each bag may contain up to and about 1, 2, 3, 4, 5, 6, 7, 8, 9, 10, 11, 12, 14, 16, 18, 20, 25, 30 ml or more of blood. Preferably, each bag contains about 10 ml of blood. Preferably, the volume of each bag is adapted for single use. Preferably, the amount of blood collected in each bag is in a sufficient quantity for one single use.

Preferably, the blood bag system or blood collection tubes device provides a sealed flow communication. More preferably, the blood bag system or blood collection tubes device provides a sealed and sterile flow communication.

Preferably, each bag can be individually sealed once the bags or tubes are filled. This has the advantage of having individual, ready-to-use, single disposable bags or tubes.

Preferably, each bag is submitted to a vacuum step. Preferably, the blood bag system or blood collection tubes device is submitted to a vacuum step.

In one preferred embodiment, each bag is inserted in a second protection or envelope. This has the advantage of offering a double protection in conformity with ISO standards on packaging (ISO11607-1 and/or ISO11607-2).

Preferably, each bag is inserted in the second envelope after vacuum. Preferably, the second envelope is submitted to vacuum and sealed. Sterilization, vacuum steps and double protection offer bags or tubes that are very safe to use.

In one embodiment, fluid flow may be controlled by conventional valving means such as snap-off plugs, removable plugs, or slide clamps.

The blood bags or tubes system may be of conventional construction being made of a plastic material that is blood compatible, flexible, translucent, and sterilizable. The plastic may be a polyvinylchloride, polyester, polyolefin, polyurethane, and so forth and may include blends of the above materials. The entry conduit and/or adapter conduits may be made of a plastic material that is the same as or different from the plastic material of the blood bags or tubes.

In one embodiment, filtering means may be integrated to the blood bag system or blood collection tubes device of the invention. The filtering means may include a housing made of rigid polyvinylchloride or the like and tubing fitments. Filtering means may be filled with a filtration medium such as cotton wool or cellulose acetate or other synthetic fibers such as polyester, polyamides, and the like. The amount of filtration medium depends upon the amount of red cells to be filtered. Usually about 20-50 grams of filtration medium are employed per 200-250 ml of red cell concentrate.

In one embodiment, an additive solution is added to prolong the storage life of the red cells. This additive solution may be, for example, a conventional red cell storage solution such as that described in Ginzburg et al., Bibl. Haemotol., 1971, No. 3, Pt. 2, 217-220; Wood et al., Blood, Vol. 42, No. 1, 1973, 17-25; Beutler, "The Red Cell in Vitro", Grum and Stratton, New York, N.Y., 1974, p. 201; Lovric et al., Medical Journal of Australia, Vol. 2, 183-186, 1977; U.S. Pat. No. 4,267,269; in an amount of about 50-100 ml per 200-250 ml of red cell concentrate.

In one embodiment, the bags or tubes of the blood bag system or blood collection tubes device of the invention may contain an anticoagulant such as Adenine-Citrate-Dextrose (ACD), Citrate-Phosphate-Dextrose (CPD), Citrate Phosphate-277 millimoles Dextrose (CP2D), CPD plus adenine, or other conventional anticoagulant, with which the collected blood mixes. The collected blood may then be processed directly or stored usually at about 4°-6° C. At processing, the bag system may be centrifuged as is customary in the art causing the red cells in the blood to settle at the bottom of the bag. Blood plasma is expressed by conventional techniques which fresh plasma and a platelet concentrate.

The blood contained in the bags or tubes may be used in any aspects and/or embodiments of the present invention.

The blood bag system or blood collection tubes device is easily manufactured and produced with great utility in the field of medicine. By using this invention, blood collections are easily made, become safer and more efficient. Advantageously, the invention provides easier traceability. Advantageously, the invention provides a blood bag system or blood collection tubes device and/or kit and/or device comprising the blood bag system or blood collection tubes device that allows easy, rapid and safe collection, storage and delivery of any blood component. A further advantage is that the collection, storage and delivery of the blood component are performed under sterile conditions in conformity with ISO standards. A further advantage is that the blood bag system or blood collection tubes device and/or kit and/or device are particularly adapted for a use at the point of care.

Preferably, the collection, storage and delivery of the blood component is performed under sterile conditions.

In one embodiment, a valve is provided which may be disposable, using a material such as acrylic resin in its manufacture.

In another aspect, the invention provides a sterile kit and/or device comprising at least one blood bag system or blood collection tubes device according to the invention. All of the apparatus required to pool blood components is provided in a sterile kit, making the pooling of blood components safe and economical.

The blood provided by the blood bag system or blood collection tubes device and/or kit and/or device according to the invention may be used for the preparation of thrombin, platelet rich plasma, platelet concentrate, cell extract, cell composition, wound healing agent and/or tissue healing agent or haemostatic agent or biological glue whether according to any aspects and/or embodiments described herein.

The blood provided by the blood bag system or blood collection tubes device and/or kit and/or device according to the invention may be used for all the applications described herein. For example, the blood provided by the blood bag system or blood collection tubes device and/or kit according to the invention may be used in surgery, ambulatory conditions or on chronic wounds.

The blood provided by the blood bag system or blood collection tubes device and/or kit and/or device according to the invention may be used as a homologous or autologous component.

When used as a homologous component, the blood and/or blood components provided by the blood bag system or blood collection tubes device and/or kit and/or device according to the invention represents an advantageous efficient, simple and low-cost alternative to known systems. It represents when the collection of autologous blood is not possible.

Examples illustrating the invention will be described hereinafter in a more detailed manner and by reference to the embodiments represented in the Figures.

EXAMPLES

The following abbreviations refer respectively to the definitions below:

ATS (autologous thrombin serum); BU (Baxothrobin unit); DMEM (Dulbecco's minimum essential medium); DMSO (Dimethyl Sulfoxide); EC (Enriched clot); FCS (fetal calf serum); HT (healing time); IU (International Unit); PBS (Phosphate Buffered Saline); PET (polyethylene terephthalate); PRP (platelet-rich plasma); PPP (platelet-poor plasma); USP (United States Pharmacopoeia); cm (centimeter); dL (deciliter); g (gram); Gy (gray); J (Joule); L (liter); min (minute); mm (millimeter); M (molar); mL (milliliter); nm (nanometer); rpm (Rotation per minute); Vol. (volume).

General Procedures & Conditions

To determine the effectiveness of compositions of the invention in promoting wound healing and/or bone and/or tissue regeneration, the following experiments are performed. Whole human blood samples are collected in a separator tube according to the invention. A tube that may be used is for example an approximately 10 to 15 mL glass tube (16 mm diameter and 120 to 130 mm in length) containing 2 to 3 mL of polyester-based thixotropic gel as well as 1 mL of sodium citrate solution at 0.1 M and containing a usable vacuum of or about 8.0 mL to 10 mL. This tube constitutes a ready-to-use device for the preparation of a platelet concentrate composition of the invention.

Another example of tube that may be used is a tube of approximately 10 mL in PET (polyethylene terephthalate) containing 2 mL of a thixotropic gel comprised of a polymer mixture and a sodium citrate solution (about 0.1 M) and containing a usable vacuum of about 8 mL to 10 mL, constitutes a ready-to-use device for the preparation of a platelet concentrate according to the invention. Another example of tube that may be used is a tube according to the invention. These tubes are filled with 2 components, vacuum aspirated, sterilized by irradiation (such as prescribed by ISO 11137, UNI EN ISO 11737-2, UNI EN 552, UNI EN 556) and hermetically sealed by a traditional cap such as a mottled bromobutyl conventional rubber stopper for the glass tube and a chlorobutyle stopper having a polyethylene cover for the operator safety. Then, the tube is centrifuged at or about 1500 g up to or about 2000 g for about 3 to 10 min, i.e., of or about 2,500 rpm up to or about 3,000 rpm with a centrifuge with a swinging rotor, having a radius of 14 cm. In case of a centrifuge having a rotor with a fixed angle of about 45°, the centrifugation time should last from 5 to about 15 min. Alternatively, the tube is centrifuged according to the invention.

After centrifugation, the platelet concentrate is collected for use in therapeutic or cosmetic applications of the invention or for the preparation of further compositions containing the obtained platelet concentrate through the mixture with further agents such as cell extracts, preferably autologous (e.g., keratinocytes, fibroblasts, bone marrow cells, osteoblasts, chondrocytes, myoblasts, corneal cells, Schwann cells, fat cells, umbilical cord stem cells, tendon cells, pancreas islet cells, ligament and gingival cells, periosteal membrane cells) and/or bone substitutes and/or coagulation activators.

The plasma concentrate, PRP, compositions of the present invention can be admixed with either tricalcium phosphate (TCP), hyaluronic acid (HA), chitosan, cream, cream mask, cell extracts, fat cells, lubricin, cd-gelatin and/or botulinum toxin.

For the preparation of cell compositions, according to the invention, the cells are prepared according to the general protocol as follows:

a) Biopsy

A biopsy of the corresponding tissue is obtained under sterile conditions using standards methods adapted to the specific cell that will be collected. The cells can be purified by washing, centrifugation or sedimentation. The cells can be isolated by centrifugation, by enzymatic digestion (trypsin, collagenase or recombined trypsin). The cells are used extemporaneously or optionally after ex-vivo culture and cell proliferation as follow.

b) Ex-Vivo Culture and Cell Proliferation

Cells used for the preparation of cell compositions, such as keratinocytes, bone marrow cells, fibroblasts; periosteum or corneal cells, such as corneal limbal stem cells; melanocytes and Langerhans cells; fat cells; muscle cells such as myoblasts and satellite cells; osteoblasts; chondrocytes; umbilical cord cells; Schwann cells, mesenchymal stem cells (MSCs), preadipocytes, pre-endothelial cells, tendon or pancreatic cells are traditionally expanded in a cell carrier medium (e.g., DMEM or Ham's) on plates (e.g., Petri dishes or culture flask) coated with a platelet concentrate, preferably autologous, enriched with fibronectin. Advantageously, a cell carrier medium like DMEM or Ham's is not required with the use of a plasma concentrate or PRP of the present invention, at a concentration of about 5% to about 20%. In addition, advantageously, this makes the cell preparations 20% more effective. The cell preparations may eventually be enriched with fibronectin. The culture media may be enriched preferably with DMEM for example in the case of keratinocytes. For cells such as bone osteoblasts, chondrocytes and myoblasts, enzymatic digestion of the corresponding tissue in presence of for example collagenase or trypsin is necessary before plating. Incubation on the plates is performed at 37° C. under a gas flow of 95% oxygen or air and 5% carbon dioxide.

Typically, incubation times vary from 10 to 20 min. The cell expansion may eventually be enhanced (like for example in the case of myoblast, fibroblast and chondrocyte cells) by phototherapy (e.g., light exposure at 633 nm of about 10 min at 2 $J/cm^2$, once a week during the incubation phase).

The explants may be cultured in Petri dishes or culture flask using air-lifting technique (Molnar et al., 1996, Tissue & Cell, 28:547-556) and air interface method (Meller et al., 2002, Br. J. Opht., 86, 463-471) with half of the explant exposed to air. The culture medium is changed regularly during incubation, such as every 3 days. The expansion of the cells in a 2D mode as planar monolayers, is obtained for example for myoblast, fibroblast and chondrocyte cells. A 3D cell growing pattern can be obtained for example for corneal, myoblast, fibroblast, chondrocyte, adipocyte and keratinocyte cells, by adding diluted autologous platelet concentrate composition according to the invention at about 5 to about 40% volume of plasma or enriched plasma to the culture medium. Typically, the addition of diluted autologous platelet concentrate composition according to the invention may be performed two or three times during the incubation time. The 3D biological scaffold then obtained allows to enhance the extra-cellular matrix which is useful for autologous stem cell transfer.

After incubation, cells may be released from dishes with gentle trypsin digestion that lifts off the cells and allows them to be pelleted. Alternatively, the cells are made thermosensible and cells may be released by heat (may use a Petri Dish coated by a thermosensitive polymer).

c) Cell Quality and Safety Check

The cell viability in the so-obtained cell preparation is checked by microscopic cell count, flow-cytometer cell count together with immunochemistry on tissue markers by standard techniques. Cell viability is also tested via trypan-blue just after cell release by trypsin. Safety of the preparation is also checked through contamination check via microbiology assay to exclude contamination with viruses or bacteria and to avoid transfer of zoonotic infections. The use of Fetal Calf Serum (FCS) is avoided thus preventing transmission of Mad Cow Disease.

d) Administration of the Cell Preparation

The cell preparation obtained above is placed in autologous platelet concentrate composition according to the invention eventually as cell carrier vehicle for transport before delivery to the patient. Then, the cell preparation obtained above is injected or transplanted into the patient. The injection or transplantation mode has to be adapted to the type of cells contained in the cell preparation according to the invention and to the aimed therapeutic or aesthetic effect. More details are given in the Examples below on the method for the preparation and use of the cell compositions according to the invention more specifically, depending on the type of cells and aimed therapeutic or aesthetic effect.

Keratinocyte cell or fibroblast cell preparations according to the invention may be used readily after collection or after cell culture as described above. However, the cell preparations according to the invention may be prepared after cell culture as described above.

The cell preparations according to the invention present a better viability and stability (including integrity of cell properties preserved such as ability to synthesize proteins and deliver growth factors) than cells prepared in a medium without autologous platelet concentrate composition according to the invention. Further, cell proliferation so obtained is enhanced: cells grow faster (about 2 to 5 days quicker) and are denser compared to control mediums and serum starved media. The advantage of the process for the preparation of a cell composition according to the invention is that the same autologous medium is used as vector for cell culture, cell preservation, cell injection, vector for cell bio-stimulation and tissue regeneration.

Example 1

Therapeutic Use of the Autologous Platelet Concentrate of the Invention in Combination with an Autologous Thrombin Enriched Serum An autologous thrombin serum to be used as a thrombin enriched preparation is prepared according to the invention.

One of the original features of this process is that the separator tubes of the invention containing respectively the autologous thrombin serum preparation and the platelet concentrate preparation can be prepared simultaneously. The glass tube for the preparation of autologous thrombin serum (ATS) is centrifuged about 8 minutes to about 10 minutes. The plastic tube (COC or COP) or glass tube for the preparation of a plasma concentrate or PRP composition is centrifuged about 8 minutes to about 10 minutes. Hence, advantageously the ATS and PRP composition are ready for use at approximately the same time.

To allow the polymerization of fibrinogen into a fibrin mesh (which occurs during the coagulation process) to occur only at the moment of application of the platelet-rich preparation on the wound, the platelet concentrate composition and autologous thrombin serum (coagulation activator) are applied simultaneously at a vol. ratio of about 10:1, 10:3 to about 10:10 (concentrate to coagulation activator ratio) to the wound, depending on the application. The difference in proportion alters the rapidity of coagulation for the glue effect.

The simultaneous delivery of both preparations is achieved for example by a device comprising two syringes (e.g., 10-mL syringe for the platelet concentrate composition and a 1-mL or 3 mL syringe for the thrombin serum), that releases the preparations simultaneously so that they mix and polymerize upon contact with the wound.

Example 2

Cosmetic Use of the Autologous Platelet Concentrate of the Invention

Examples of cosmetic use of the autologous platelet concentrate of the present invention include:

Admixing the platelet concentrate according to the invention with a cream, preferably an emulsion, before application to a wound, after surgery or on healthy skin. During the absorption process, the platelet preparation is carried into the skin by the cream or emulsion in order to amplify the hydrating benefit and to biostimulate the regeneration or rejuvenation of the skin. Injection in the dermal layer may be made with the technique of mesotherapy by repeated injections by hand or a device without needle. Injection may be made subcutaneously in the wrinkle for volume correction. Injection of the platelet concentrate combined at a ratio of 10:1 or 10:3 with the autologous thrombin serum for filler effect and/or consistent volume correction may be made in the wrinkle, forehead, jowls, molar region, cheeks, chin, neck and/or chest. When appropriate, injection of plasma concentrate combined to a freshly aspirated fat tissue at a ratio of about 10:10 may be made subcutaneously for important volume correction of the face. When appropriate, injection of plasma concentrate combined to a freshly aspirated fat tissue at a ratio of about 10:3 or about 10:2 may be made subcutaneously for important volume correction of the breast or contouring.

Using a hydrogel like the Albugel (EP 1 543 846) preparation of 100% Albumin or any other hydrogel resulting from the reticulation of Albumin and other chemical compound like polyethylene glycol or any other ingredient, using a paper based highly hydrophilic carrier to leave in contact with the skin until the platelet rich plasma is absorbed.

The present invention encompasses the following mesotherapy injection methods:
In the papillary dermis,
Subcutaneous in the reticular dermis, or
In a deep level above the periosteum.

The 3 levels of injection also called "Medical face lifting" may be performed with plasma alone, plasma plus adipose tissue and/or plasma plus tricalcium phosphate.

Example 3

Autologous Muscle Cell Association Preparation

Examples of autologous cell association according to the invention can be prepared by using the process according to the invention wherein skeletal muscle cells (muscle progenitor cells or satellite stem cells) are provided under step (d) or (e).

a) Myoblast Progenitor Stem Cells

Skeletal muscle biopsy is obtained from the Vastus lateralis and measures 7×3 cm. Muscle is primed the day before biopsy, with intra-muscular injection at proposed biopsy site (10 by 15 cm skin area on lateral aspect of thigh overlying the vastus lateralis muscle and just above the knee joint, on either side) with Decadon and Marcaine (long acting Lignocaine). Muscle is diced and enzymatically digested with combination of collagenase, pronase and trypsin (Worthington). Muscle explants are plated in Petri dishes coated with an autologous platelet concentrate composition according to the invention, and incubated in 95% oxygen and 5% carbon dioxide at 37° C. for 3 to 4 weeks. Desmin or CD-56 expression is used as myoblast marker to identify myoblasts from fibroblasts. Myoblast progenitor cell proliferation in 3D is shown on FIG. 3. Cell proliferation can be enhanced by photo-light exposure at 633 nm of 2 J/square centimeter for 10 min during culture. The day of transplantation (e.g., after 3 to 4 weeks of incubation), the skeletal muscle cells may be released by trypsin or any method as described herein and placed in the autologous platelet concentrate composition according to the invention. Injections into the myocardium can be made as direct injection or multiple catheter injections into the left ventricle myocardium. The myoblast cell preparation according to the invention is useful for cardiac disorders such as heart regeneration, treatment of heart failure, chronic cardiac failure, ischemic and non-ischemic cardiac failure and non-ischemic cardiomyopathy. Ejection fraction can be improved by 9% for cardiac recipients of skeletal myoblasts.

The above cell preparation may also be useful for the treatment of urinary incontinence (myoblast cell extracts prepared as described above and injected into the bladder neck), reflux oesophagitis or gastro-oesophageal reflux disorder (myoblast cell extracts prepared as described above injected into the lower oesophageal sphincter) and anal incontinence (myoblast cell extracts prepared as described above and injected in para-anal area).

Alternatively, a combined preparation of fibroblast and myoblast may be carried out (fibroblasts are present in the muscle biopsy and sprout from the perimysium alongside the myotubes and satellite stem cells). In case of the treatment of cardiac disorders, a mix of fibroblast cell preparation and myoblast cell preparation (obtained as indicated above) is inserted into the myocardium in a ratio fibroblast/myoblast of about 30:70.

For bladder neck incontinence treatment, a separate culture of fibroblasts is made at the same time as the myoblasts as described above and the fibroblast cell preparation is injected para-urethrally and myoblast cell preparation is injected into the rhabdosphincter, under ultrasound control.

b) Satellite Stem Cells

Myoblasts and satellite stem cells are cultured ex vivo in presence of autologous platelet concentrate composition according to the invention. Cell proliferation priming is observed after 7 days of primary culture.

Cells are then harvested after incubation of about 3-4 weeks and placed in tissue culture medium (DMEM plus 5-20% vol. autologous platelet concentrate composition according to the invention) containing a human de-epitheliased amnion patch measuring 4×4 cm and the autologous platelet concentrate composition according to the invention. Alternatively, a patch of autologous activated fibrin polymer may be used. The autologous activated fibrin polymer is prepared by centrifugating the plasma with calcium gluconate at a ratio of about 10:3 or about 10:10. The preparation is then subjected to UV irradiation for 10 min. During incubation (typically about 2 to about 3 weeks), the cells spread over the amnion construct and form a monolayer. Viability and monolayer progress is assessed by twice weekly biopsy of patch edge and histological assessment for thickness of monolayer.

The day of transplantation (e.g., after about 3 to 4 weeks of incubation), the ventricular surface is spread with the autologous platelet concentrate composition according to the invention and then the patch obtained above is placed with cells down side onto a raw surface of the ischemic ventricle in order to allow the stem cells on the patch to populate the ischemic segment after ventricular injection. Cell retention is maintained by the amnion that is inert and induces no immunological reaction.

The satellite stem cell preparation according to the invention is useful for heart regeneration and treatment of heart failure as tissue engineering preparation for cardiomyoplasty.

Example 4

Autologous Fibroblast Cell Association Preparation

An example of autologous fibroblast cell association according to the invention can be prepared by using the process according to the invention wherein dermal fibroblast cells are provided under step (d) or (e).

Dermal fibroblasts are isolated and expanded according to the following procedure: One month before biopsy, the prime donor skin area (behind an ear of anterior axillary fold, e.g., non solar aged area) is treated with vitamin A cream to activate the dermal fibroblasts. A skin biopsy of 10×6 mm full thickness is performed and dissected under microscope to remove all epithelium. The de-epithelialized biopsy (dermis) is then cut into 3×3 mm blocks as explants. The papillary dermis is then placed upwards and cultured using air-lifting technique (Molnar et al., 1996, above) and air interface (Metier et al., 2002, above) with half of the explant exposed to air. The explants are plated (e.g., 6 explants per well) in DMEM and cultured at 37° C. at 95% oxygen and 5% CO2 for about 3-5 up to about 9 days in Petri dishes or culture flask. The medium is changed every 3 days. The fibroblasts expansion in 2D mode as planar monolayers, as static growth is observed during incubation. At days 7 to 9 after the start of incubation, a change in proliferation and phenotype pattern to 3D is obtained by adding diluted 5-20% autologous platelet concentrate composition according to the invention to the culture medium: cells are primed with the autologous platelet concentrate composition (0.2 ml per well) just to cover base. Cells grow then as a 3D fibrin gel matrix. Cells then differentiate to form biological scaffold or network in fibrin gel. Cell number is measured by daily counting under a grid and to assess apoptosis: use inverted microscope (Olympus®).

After 3 to 6 weeks of incubation, the cells are harvested from the fibrin gel. Cell viability is assayed with classical Trypan blue method and with bacteriological evaluation, including virus contamination. The expanded fibroblast cell extract obtained above is placed in a syringe in presence of autologous platelet concentrate composition according to the invention and the preparation is injected into face wrinkles, more specifically under the wrinkles. Injections must be performed over the whole face to cover forehead, jowls, molar region, cheeks, chin and neck. Cell expansion may be increased by photo light exposure of cell culture at 633 nm. The fibroblast cell preparation according to the invention is useful for facial rejuvenation, amelioration of facial wrinkles and rhytids, treatment of skins damaged by radiation (radiodermatitis or sun damaged skin), aged skins or burned skins and/or in the amelioration of facial wrinkles, rhytids, acne (especially after dermabrasion treatment), burns, rubella or small pox scars, vitiligo, lipoatrophy or lypodystrophy, such as AIDS-related lypodystrophy; Kaposi's sarcoma, skin keloids or Dupuytren's palmar fibromatosis and/or in skin rejuvenation treatments.

Example 5

Autologous Adipose Tissue & Fat Cell Association Preparation

Adipose tissue is aspirated preferably in the lower abdomen area, purified by PBS washing, centrifuged, with sedimentation in order to isolate the fat tissue from the triglyceride and debris. In the meantime, blood is collected and centrifuged for the preparation of a plasma concentrate or PRP composition according to the invention. The combination of the fat tissue and PRP composition is performed in the syringe used for the fat aspiration once the triglycerides have diminished, by using a sterile transfer device for aspiration of PRP composition. The ratio of plasma concentrate and fat tissue is 10:10 for the face and 10:3 for the breast and contouring.

Preferably, the injection is done extemporaneously, in a minimal period of preparation time of both concentrated cells, and for a minimum time of cell manipulation ex-vivo.

Examples of autologous cell association according to the invention can be prepared by using the process according to the invention wherein for example adipose stem cells or mesenchymal stem cells (MSCs) are provided under step (d) or (e). MSCs may by isolated by collagenase (preadipocytes, pre-endothelial cells) and put in suspension with PRP and the preparation injected including subcutaneously, intra-articular, or for orthopedic surgery. The preparation may be combined with a soak acellular matrix to be applied directly on a wound, or may be cultivated in laboratory before application. Adult adipose stem cells are isolated by standard culture method in 5-20% vol. of an autologous platelet concentrate composition according to the invention. The preparation is then injected with an applicator into patients suffering from tissue deficiencies, such as post traumatic deficiencies or age-related deficiencies for patients being around about 40 years-old. The fat cell preparation according to the invention is useful for the treatment of lipoatrophy such as in HIV/AIDS patients and others with congenital hemiatrophy of the face.

Example 6

Autologous Chondrocyte Cell Association Preparation

Examples of autologous cell association according to the invention can be prepared by using the process according to the invention wherein chondrocyte cells are provided under step (d) or (e).

Cartilage is isolated from the donor's knee (biopsy size 10×5 mm) and diced. The cartilage chondrocyte cells are cultured for 4-6 weeks in medium enriched with a diluted 5-20% autologous platelet concentrate composition according to the invention. Cartilage cells are then released by enzymatic digestion (collagenase and pronase). The cell preparation is then incorporated surgically into the patient with deep chondral defects and damage.

The chondrocyte cell preparation according to the invention is useful for the treatment of deep cartilage damage and erosion or arthroscopy.

Another example of the use of a chondrocyte cell preparation according to the invention is the use in rhinoplasty without surgery by a single injection procedure: A patient suffering from congenital cartilage nose atrophy.

The day before injection, a biopsy of the cartilage of the ear 0.4*0.4 cm is performed and placed in a sterile recipient filled with DMEM and antibiotic. The biopsy is treated with enzymatic digestion including trypsin and collagenase. The released chondrocytes are then re-suspended in the autologous platelet concentrate composition according to the invention. The patient receives first a local anesthesia, and nose disinfection. Then, the above chondrocyte preparation is injected on the cartilage surface and/or periosteum membrane of the site requiring augmentation of volume or lift. In a second phase, autologous platelet concentrate composition according to the invention is injected into the superficial part of the nose skin, in order to biostimulate regeneration and the rejuvenation of the skin. After one hour, the injection is achieved and the patient could return home. An exceptional recovery of viable cells is observed: the amount of chondrocyte cells and plasma cells recovered and injected was about $10^9$ cells. The chondrocyte cell preparation according to the invention is therefore useful for the treatment of nasal cartilage defects, without surgical procedure, but only by injection.

Example 7

Autologous Umbilical Cord Stem Cell Association Preparation

An example of autologous cell association according to the invention can be prepared by using the process according to the invention wherein umbilical cord stem cells are provided under step (d) or (e). Umbilical cord stem cells are isolated and then cryo-preserved and used to treat blood disorders.

The umbilical cord stem cell preparation according to the invention is useful for the treatment of haematological diseases (like Thalassaemia).

The process of injection is resuspension of stem cells in the plasma concentrate followed by reinjection.

Example 8

Autologous Tendon Cell Association Preparation

An example of autologous cell association according to the invention can be prepared by using the process according to the invention wherein tendon cells are provided under step (d) or (e).

Tendon fibroblast cells are isolated according to standard procedures in 5-20% vol. of autologous platelet concentrate composition according to the invention. The tendon fibroblast cells are cultured for about 1 to about 3 weeks in culture medium enriched with an autologous platelet concentrate composition according to the invention. Before injection, the cells are resuspended in freshly processed plasma concentrate. The cell preparation is then injected into the patient at the injury site (e.g., torn tendon, arthritic area). The injection can be guided by echography, for localisation of the damaged site, and better graft of the implanted solution.

The injection of the tendon fibroblast cell preparation may also be performed next to rotator cuff in shoulder: first the rotator cuff tear is repaired arthroscopically, then the tendon fibroblast cell preparation is injected via a long catheter onto the sutured area. This improves the healing of the tendon fibroblast at the edge of the rotator cuff, prevents haematoma in confined space under the acromion, and prevents frozen shoulder by speeding up healing and enhancing rehabilitation and joint movement. The tendon cell preparation according to the invention is useful for the treatment of torn tendons, arthritis in joint caused by traumas or by aging, rotator cuff in shoulder.

Example 9

Autologous Ligament and Gingival Cell Association Preparation

An example of autologous cell association according to the invention can be prepared by using the process according to the invention wherein periosteal membrane and gingival cells are provided under step (d) or (e).

Under general and local anesthesia, periosteum (approximately 10×10 mm) is aseptically harvested from the buccal side of the mandibular body in four healthy female beagle dogs. The harvested periosteum is cut into 3×3 mm pieces. The tissues are placed directly on a 6-well plate and cultured (for about 3 to about ??? weeks) in a humidified atmosphere of 5% $CO2$ and 95% air at 37° C. in a culture medium enriched with a 5-20% autologous platelet concentrate composition according to the invention. The periosteal membrane and gingival cells are isolated by enzymatic digestion and cultured by static technique.

Typically, 6 weeks of culture is sufficient to obtain appropriate periosteal membrane thickness for grafting.

The autologous platelet concentrate composition and the cell preparation are injected after resuspension into the patient at the injury site.

Example 10

Autologous Corneal Cell Association Preparation

Preparation on a petri dish with a thermo sensitive coating membrane, for the collection of cells without enzymatic solution like collagenase or trypsin. Examples of autologous cell association according to the invention can be prepared by using the process according to the invention wherein corneal cells are provided under step (d) or (e).

A biopsy is taken from the epicanthis on the edge of the cornea and the corneal limbal stem cells were expanded for autologous transplantation in the same person after 4 weeks of culture in Petri dishes or flasks coated with an autologous platelet concentrate composition according to the invention.

The corneal cultured stem cells (of limbal origin) may be ex vivo engineered onto the surface of de-epithelialised human amnion in a monolayer, after seeding the construct with a suspension of cultured and viable corneal keratinocytes according to the invention. About 500,000 cells are used for the seeding and the cells are allowed to cover the surface of the construct after further incubation of about another 3 weeks. The engineering with cells occurs after about three weeks of primary cell culture, and re-seeding may be necessary. The resulting biological cell-biocomposite construct consists of collagen, amnion fibers and corneal keratinocytes, consisting of membrane and monolayer of cells. The corneal cell preparation according to the invention can be spread onto a dissolvable contact lens that is applied to the damaged cornea. The contact lens disappears and the cells close the corneal defect. The corneal cell preparation according to the invention can be administered topically in eye drops in patients suffering from dry eye symptoms. Alternatively, the above amnion can be used on its own on the scarred cornea or the construct and the cell preparation according to the invention can be attached to the inside of a biological or artificial contact lens and then applied to the cornea and covered with an eye pad.

Alternatively, corneal cells are resuspended in freshly processed plasma concentrate before application.

The corneal cell preparation according to the invention is useful in alleviating the pain of dry eye, for the treatment of Stevens-Johnson Syndrome and corneal blindness due to acid and corrosive alkali burns in industry, corneal ulcers such as recalcitrant neurotrophic, herpetic and immunologically induced corneal ulceration.

Example 11

Autologous Bone Marrow Cell Association Preparation

An example of autologous cell association according to the invention can be prepared by using the process according to the invention wherein bone marrow cells are provided under step (d) or (e).

Hip bone marrow is aspirated, harvested and centrifuged in a ready-to-use device for the preparation of a bone marrow concentrate in order to separate red blood cells.

The bone marrow cell preparation is used alone or then admixed to the platelet concentrate according to the invention or centrifuged again with calcium gluconate to form a suturable membrane and applied or injected with an applicator to the injured site of the patients. The bone marrow cell preparation according to the invention is useful for the treatment of bone defect or cartilage defect. The bone marrow cell preparation may be used alone or in combination with a plasma concentrate according to the invention. A cartilage membrane may be used as well with calcium gluconate.

Example 12

Autologous Schwann Cell Association Preparation

An example of autologous cell association according to the invention can be prepared by using the process according to the invention wherein Schwann cells are provided under step (d) or (e).

Under local anaesthesia, a biopsy is performed on either the N. Saphenous or N. Suralis in the lower extremity. The nerve biopsy is cut into small blocks and primary cultures are induced in Petri dishes enriched with an autologous platelet concentrate composition according to the invention.

Monolayers are expanded in 3D and the cells are eventually harvested by trypsin digestion and resuspended in a freshly harvested platelet concentrate in a syringe for local infiltration of the surgically exposed and damaged spinal cord. The cultivated cells have been shown to contain myelin. The Schwann cell preparation according to the invention is useful for the treatment of peripheral nerve damage, nerve suture and spinal cord injury.

Example 13

Autologous Human Islet Cell Preparation

An example of autologous cell association according to the invention can be prepared by using the process according to the invention wherein pancreas islet cells are provided under step (d) or (e).

Pancreas islets are harvested by open biopsy and separated by conventional enzymatic digestion and Ficol or Hypaqe separation (Page et al., 2007, Diba. Vas. Dis. Res., 7-12) then resuspended in a medium enriched with an autologous platelet concentrate composition according to the invention.

The pancreas islet cell preparation is then injected via the portal vein into the liver.

The pancreas islet cell preparation according to the invention is useful for the treatment of type I diabetes or insulin-dependent diabetes and for the reversal of hyperglycaemia of diabetes mellitus.

Example 14

Autologous Human Osteoblast Cell Preparation

An example of autologous cell association according to the invention can be prepared by using the process according to the invention wherein osteoblast cells are provided under step (d) or (e).

Cortical punch bone biopsy is derived from the iliac crest or equivalent site (maxilla) under local anaesthesia. The bone biopsy is placed aseptically in DMEM medium at 4° C., or equivalent transport medium by those experienced in the art of bone and osteoblast culture ex vivo. The bone biopsy is then diced and digested in diluted 10% type-1 collagenase (Sigma or Boehringer) at 37° C. for 15 min under laminar flow hood. Alternatively, trypsin digestion (Worthington) may be used. Enzymatic digestion is terminated with three washes with an autologous platelet concentrate composition according to the invention, at 10% in DMEM at 4° C. The preparation is centrifuged, pelleted and resuspended. The bone fragments are plated on Petri dishes or flasks as explants with air-lifting technology in an autologous platelet concentrate composition according to the invention. The preparation is cultured at 37° C. with antibiotics, gentimicin and amphotericin-B under a gas flow of 95% air and 5% CO2. The culture medium is changed three times per week, each time spiking DMEM medium with 10-20% vol. of an autologous platelet concentrate composition according to the invention. The cell viability and morphology are evaluated three times a week to assess cell crawling, apoptosis and 3D dimensional monolayer progression. The formation of microfilament and differentiation is assessed by inverted microscopy (Olympus®). Absence of bacterial and viral contamination is checked. Osteoblasts can be engineered in a freshly harvested autologous fibrin polymer membrane prepared by centrifugation of platelet concentrate with calcium gluconate at a ratio of about 10:3 or about 10:10. The fibrin polymer is suturing. Osteoblasts can be engineered onto human amnion to create cell biocomposite scaffold and cell monolayer carrier/construct after membrane seeding with 100,000 cells as obtained above and allowing monolayer membrane expansion over 3-4 weeks allowing unique construction of osteoblast-amnion-membrane construct for use and transfer to cover a bone defect or grafted area following non-union of fracture in any site. Osteoblasts can alternatively be mixed to a fresh bone marrow concentrate and platelet concentrate before injection/application, and further combined with autologous thrombin serum when there is a need of a soft gel.

The osteoblast cell preparation according to the invention is useful for the treatment of bone defects, bone grafts or bone disorders.

I claim:

1. A composition comprising hyaluronic acid and at least one anticoagulant and at least one thixotropic gel, wherein said hyaluronic acid is layered beneath said thixotropic gel and/or wherein said thixotropic gel is layered beneath said anticoagulant.

2. The composition according to claim 1, wherein said composition comprises hyaluronic acid, a thixotropic gel and an anticoagulant, wherein said hyaluronic acid is layered beneath said thixotropic gel and wherein said thixotropic gel is layered beneath said anticoagulant.

3. A centrifugation tube comprising a composition according to claim 2.

4. An article of manufacture comprising the centrifugation tube of claim 3.

5. The centrifugation tube according to claim 3, wherein said centrifugation tube is:

a) a glass separator tube containing a polyester-based thixotropic gel, a buffered sodium citrate solution at 0.10 M and hyaluronic acid;

b) a polyethylene terephthalate separator tube containing a highly thixotropic gel formed by a polymer mixture, an anhydrous sodium citrate at 3.5 mg/m and hyaluronic acid, c) a Cyclic Olefin Copolymer (COC) or Cyclic Olefin Polymer (COP) separator tube containing a polyester-based thixotropic gel, a buffered sodium citrate solution at 0.10 M and hyaluronic acid; or d) a Cyclic Olefin Copolymer (COC) or Cyclic Olefin Polymer (COP) filter separator tube containing hyaluronic acid and a buffered sodium citrate solution at 0.10 M or an anhydrous sodium citrate at 3.5 mg/mL.

6. The composition according to claim 1, wherein said composition further comprises:

a) enriched plasma and/or whole blood and/or bone marrow, and/or b) a coagulation activator or thrombin serum, and/or c) at least one cell extract, cell composition, tricalcium phosphate, bone substitute, chitosan, hyaluronic acid, cream, cream mask, fat cells, fat tissue, bone marrow concentrate, lubricin, cd-gelatin, botulinum toxin, calcium gluconate and/or stem cells, wherein said cell extract is selected from an extract of: keratinocytes, bone marrow cells, osteoblasts, chondrocytes, fibroblasts, periosteum or corneal cells, melanocytes, Langerhans cells, fat cells, muscle cells, umbilical cord cells, mesenchymal stem cells (MSCs), preadipocytes, adipocytes, stem cells, periosteal cells, gingival cells, pre-endothelial cells, Schwann cells, ligament cells, tendon cells or pancreas islet cells.

7. The composition according to claim 6, wherein the composition comprises:

a) plasma;

b) platelets at a concentration of at least $300 \times 10^9$ cells/L;

c) white blood cells at a concentration of at least $7 \times 10^9$ cells/L;

d) fibrinogen at a concentration of at least 3 mg/L;

e) optionally a coagulation activator or thrombin serum;

f) optionally at least one cell extract, cell composition, tricalcium phosphate (TCP), a bone substitute, chitosan, hyaluronic acid, cream, cream mask, fat cells, fat tissue, bone marrow concentrate, lubricin, cd-gelatin, botulinum toxin, calcium gluconate and/or stem cells, wherein said cell extract is selected from an extract of: keratinocytes, bone marrow cells, osteoblasts, chondrocytes, fibroblasts, periosteum or corneal cells, melanocytes, Langerhans cells, fat cells, muscle cells, umbilical cord cells, mesenchymal stem cells (MSCs), preadipocytes, adipocytes, stem cells, periosteal cells, gingival cells, pre-endothelial cells, Schwann cells, ligament cells, tendon cells or pancreas islet cells.

8. The composition according to claim 7, wherein the muscle cells are selected from myoblasts and satellite cells.

9. The composition according to claim 6, wherein the thrombin serum, enriched plasma, cell composition, stem cells, fat cells, fat tissue, hone marrow concentrate and/or cell extract is autologous.

10. A method of treating a subject comprising administering a composition according to claim 6 to a wound, damaged tissue, damaged bone, a periodontal defect or cavity or the skin of a subject.

11. The composition according to claim 6, wherein the muscle cells are selected from myoblasts and satellite cells.

12. The composition according to claim 1, wherein said anticoagulant is selected from anyhirudin, benzylsulfonyl-d-Arg-Pro-4-amidinobenzylamide (BAPA), heparin, sodium citrate, citrate, acid citrate dextrose (ACD), citrate-theophylline-adenosine-dipyridamole (CTAD), potassium-ethylenediaminetetraacetic acid (EDTA) or a combination thereof.

13. A container comprising a composition according to claim 1.

14. The container according to claim 13, wherein said container is a centrifugation tube.

15. The centrifugation tube according to claim 14, wherein the centrifugation tube comprises the layer of hyaluronic acid, the layer of the thixotropic gel and the layer of anticoagulant, wherein the layers of hyaluronic acid, thixotropic gel and anticoagulant migrate across each other upon centrifugation of the centrifugation tube.

16. The container according to claim 13, wherein said hyaluronic acid is at the bottom of said container and comprises about 1 ml to about 2 ml of hyaluronic acid.

17. The container according to claim 13, comprising about 1 ml to about 2 ml of hyaluronic acid, about 2 g of thixotropic gel and about 1 ml of sodium citrate at 0.109M.

18. The container according to claim 13, wherein said container:

i) has an inlet for introducing whole blood; and/or ii) is held in a vacuum intended to aspirate a whole blood sample; and/or iii) is sterile; and/or iv) has a usable vacuum of or about 8 to about 10 mL; and/or v) is suitable for undergoing centrifugation; and/or vi) is sealed; and/or vii) is manipulated entirely in closed circuit.

19. An article of manufacture comprising the container of claim 13.

20. The article of manufacture according to claim 19, wherein:

a) said article of manufacture is a medical device or kit;

b) said anticoagulant is sodium citrate; and c) said container is a tube.

21. An article of manufacture comprising a composition according to claim 1 within a container.

22. The article of manufacture according to claim 21, wherein said anticoagulant is sodium citrate and said container is a tube wherein said container comprises hyaluronic acid at the bottom of said tube followed by said thixotropic gel which is followed by said anticoagulant.

23. The article of manufacture according to claim 21, said composition within the container further comprising whole blood.

24. The article of manufacture according to claim 21, said composition within the container comprising hyaluronic acid and enriched plasma.

25. The article of manufacture according to claim 21, wherein:

a) said article of manufacture is a medical device or kit;

b) said anticoagulant is sodium citrate; and c) said container is a tube.

* * * * *